(12) United States Patent
Wiebe, III et al.

(10) Patent No.: US 11,602,361 B2
(45) Date of Patent: *Mar. 14, 2023

(54) PATIENT SPECIFIC IMPLANT TECHNOLOGY

(71) Applicant: Smith & Nephew, Inc., Memphis, TN (US)

(72) Inventors: James Bennett Wiebe, III, Coldwater, MS (US); Ryan Lloyd Landon, Olive Branch, MS (US); Brian William McKinnon, Arlington, TN (US); Randy C. Winebarger, Southaven, MS (US); Ruxandra Cristiana Marinescu Tanasoca, Memphis, TN (US); Roger Ryan Dees, Jr., Drummonds, TN (US); William L. Bowers, Jr., Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 351 days.

This patent is subject to a terminal disclaimer.

(21) Appl. No.: 16/826,654

(22) Filed: Mar. 23, 2020

(65) Prior Publication Data
US 2020/0237385 A1 Jul. 30, 2020

Related U.S. Application Data

(63) Continuation of application No. 14/423,268, filed as application No. PCT/US2013/057822 on Sep. 3, 2013, now Pat. No. 10,603,056.
(Continued)

(51) Int. Cl.
A61B 17/17 (2006.01)
G06F 16/22 (2019.01)
(Continued)

(52) U.S. Cl.
CPC .......... *A61B 17/1764* (2013.01); *A61B 17/70* (2013.01); *A61B 17/8897* (2013.01);
(Continued)

(58) Field of Classification Search
CPC ......... G06T 7/0012; G06T 2207/30008; G06F 16/22; G06F 30/00; A61B 17/1764;
(Continued)

(56) References Cited

U.S. PATENT DOCUMENTS 4,721,104 A 1/1988 Kaufman et al.
5,258,032 A 11/1993 Bertin
(Continued)

FOREIGN PATENT DOCUMENTS

WO 2006091494 A1 8/2006
WO 2007109467 A1 9/2007

OTHER PUBLICATIONS

Extended European Search Report issued in European Application No. 13833657.3 dated Dec. 1, 2016.
(Continued)

*Primary Examiner* — Katrina R Fujita
(74) *Attorney, Agent, or Firm* — KDB Firm PLLC

(57) ABSTRACT

Patient specific implant technology, in which an outline representation of a portion of an outer surface of a periphery of a bone volume is determined and the outline representation is used in operations related to implant matching. In addition, an instrument may be made to match a perimeter shape of a Patient Specific Knee Implant with features for locating holes in a distal femur such that posts or lugs in a femoral implant locate the femoral implant centered medial-laterally within an acceptable degree of precision to prevent overhang of either the side of the femoral implant over the perimeter of the distal femur bone resections. Further, a two-dimensional outline representation may be segmented
(Continued)

into segments that correspond to resection cuts used in fitting an implant on a portion of a bone and operations related to implant matching may be performed based on the segments.

21 Claims, 49 Drawing Sheets

Related U.S. Application Data

(60) Provisional application No. 61/771,409, filed on Mar. 1, 2013, provisional application No. 61/696,083, filed on Aug. 31, 2012.

(51) Int. Cl.
| | | |
|---|---|---|
| A61B 17/70 | (2006.01) | |
| A61B 17/88 | (2006.01) | |
| G06F 30/00 | (2020.01) | |
| G06T 7/00 | (2017.01) | |
| A61B 34/10 | (2016.01) | |

(52) U.S. Cl.
CPC .............. *A61B 34/10* (2016.02); *G06F 16/22* (2019.01); *G06F 30/00* (2020.01); *G06T 7/0012* (2013.01); *A61B 2034/105* (2016.02); *A61B 2034/108* (2016.02); *G06T 2207/30008* (2013.01)

(58) Field of Classification Search
CPC ..... A61B 17/70; A61B 17/8897; A61B 34/10; A61B 2034/105; A61B 2034/108
See application file for complete search history.

(56) References Cited

U.S. PATENT DOCUMENTS

| | | | |
|---|---|---|---|
| 6,080,196 | A | 6/2000 | Bertin |
| 6,488,687 | B1 | 12/2002 | Masini |
| 6,916,324 | B2 | 7/2005 | Sanford et al. |
| 7,104,997 | B2 | 9/2006 | Lionberger et al. |
| 8,409,210 | B2 | 4/2013 | Bhatnagar et al. |
| 8,551,179 | B2 | 10/2013 | Jones et al. |
| 8,682,052 | B2* | 3/2014 | Fitz ....................... A61F 2/3872 382/128 |
| 2006/0173463 | A1 | 8/2006 | Dees, Jr. |
| 2006/0265078 | A1 | 11/2006 | McMinn |
| 2007/0118243 | A1 | 5/2007 | Schroeder et al. |
| 2007/0233266 | A1 | 10/2007 | Williams, III et al. |
| 2007/0255288 | A1 | 11/2007 | Mahfouz et al. |
| 2007/0276501 | A1 | 11/2007 | Betz et al. |
| 2008/0262812 | A1 | 10/2008 | Arata et al. |
| 2008/0319448 | A1 | 12/2008 | Lavallee et al. |
| 2009/0087276 | A1 | 4/2009 | Rose |
| 2009/0088762 | A1 | 4/2009 | Koenemann |
| 2009/0089034 | A1* | 4/2009 | Penney ............. A61B 17/1757 703/11 |
| 2009/0198340 | A1 | 8/2009 | Cloutier et al. |
| 2009/0264894 | A1 | 10/2009 | Wasielewski |
| 2009/0265011 | A1 | 10/2009 | Mandell |
| 2009/0265013 | A1 | 10/2009 | Mandell |
| 2009/0312805 | A1 | 12/2009 | Lang et al. |
| 2010/0049195 | A1 | 2/2010 | Park et al. |
| 2010/0305575 | A1 | 12/2010 | Wilkinson et al. |
| 2011/0029093 | A1 | 2/2011 | Bojarski et al. |
| 2011/0066247 | A1 | 3/2011 | Ries et al. |
| 2011/0066248 | A1 | 3/2011 | Ries et al. |
| 2011/0087332 | A1 | 4/2011 | Bojarski et al. |
| 2011/0092977 | A1 | 4/2011 | Salehi et al. |
| 2011/0093108 | A1* | 4/2011 | Ashby ................. A61F 2/30942 703/2 |
| 2011/0257653 | A1 | 10/2011 | Hughes et al. |
| 2011/0295378 | A1 | 12/2011 | Bojarski et al. |
| 2011/0305379 | A1* | 12/2011 | Mahfouz .............. A61F 2/3859 345/419 |
| 2012/0041446 | A1* | 2/2012 | Wong .................. A61F 2/30756 606/86 R |
| 2012/0078263 | A1 | 3/2012 | Parisi et al. |
| 2012/0150243 | A9 | 6/2012 | Crawford et al. |
| 2012/0209394 | A1 | 8/2012 | Bojarski et al. |
| 2012/0259335 | A1 | 10/2012 | Scifert et al. |
| 2012/0310246 | A1 | 12/2012 | Belcher et al. |
| 2012/0316563 | A1 | 12/2012 | Metzger et al. |
| 2013/0006370 | A1 | 1/2013 | Wogoman et al. |
| 2013/0203031 | A1 | 8/2013 | Mckinnon et al. |
| 2013/0211411 | A1 | 8/2013 | Tuke et al. |
| 2013/0211531 | A1 | 8/2013 | Steines et al. |
| 2014/0018813 | A1 | 1/2014 | Mckinnon et al. |
| 2014/0228860 | A1* | 8/2014 | Steines ................. A61B 34/10 606/130 |
| 2014/0257309 | A1 | 9/2014 | Aram et al. |
| 2015/0032113 | A1 | 1/2015 | Anderson |
| 2015/0173781 | A1 | 6/2015 | Metzger et al. |
| 2015/0190143 | A1 | 7/2015 | Tarabichi et al. |
| 2015/0190145 | A1 | 7/2015 | Aram et al. |
| 2017/0000569 | A1* | 1/2017 | Mahfouz ............. A61F 2/30942 |
| 2017/0000614 | A1* | 1/2017 | Mahfouz ............. A61B 8/4245 |

OTHER PUBLICATIONS

International Search Report/Written Opinion in PCT/US2013/057822 dated Dec. 30, 2013, 10 pages.
Japan Decision of Rejection for Japanese Application No. 2015-530137 dated Mar. 5, 2018 (with machine translation).
Japan Notice of Reasons for Rejection for Japanese Application No. 2015-530137 dated Jul. 3, 2017 (with machine translation).

\* cited by examiner

3700

3800

4300

4500

4600

4700

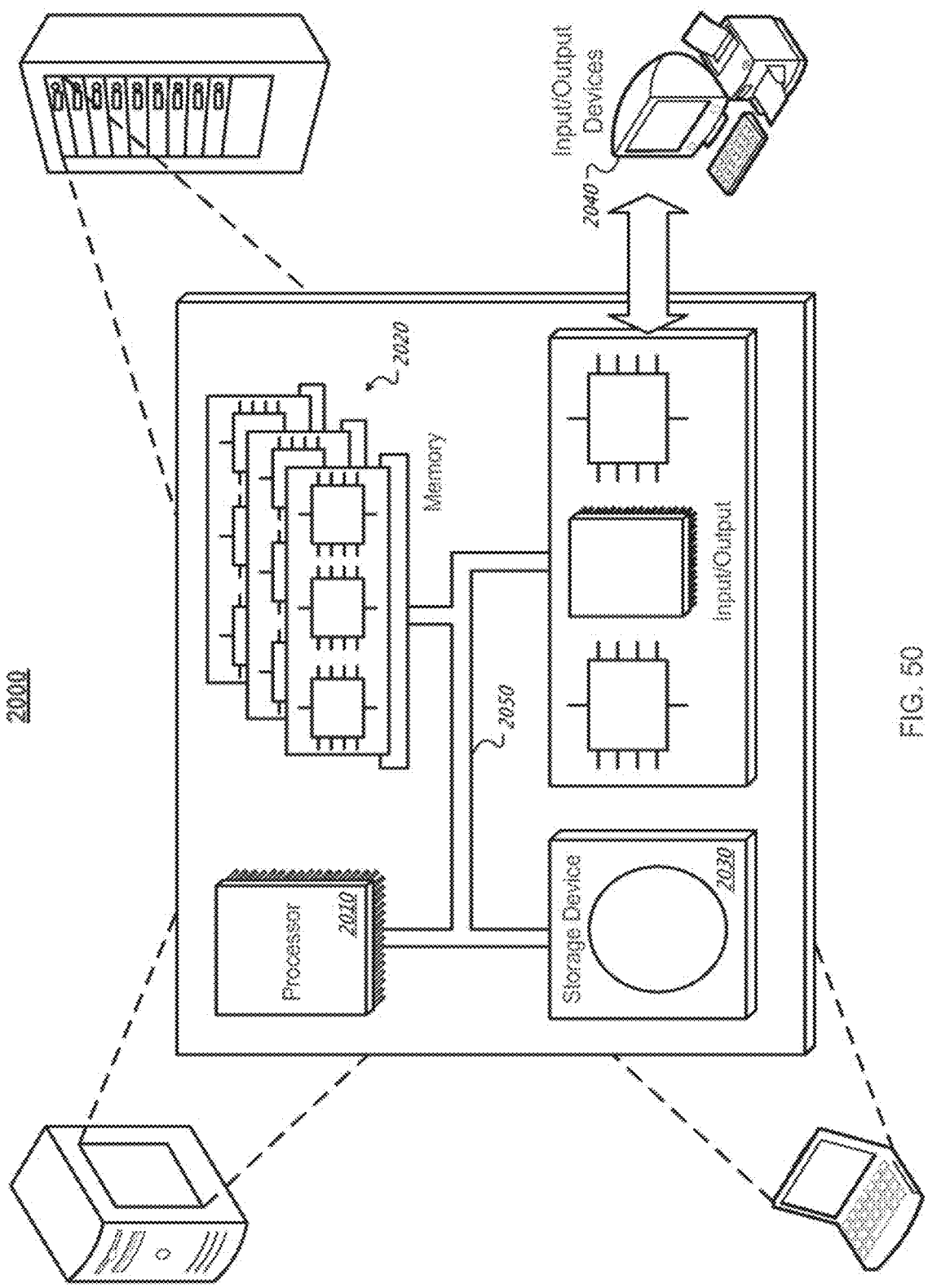

PATIENT SPECIFIC IMPLANT TECHNOLOGY

CROSS-REFERENCE TO RELATED APPLICATIONS

This application is a continuation of U.S. patent application Ser. No. 14/423,268, titled "Patient Specific Implant Technology," filed Feb. 23, 2015, which is a U.S. national stage filing under 35 U.S.C. § 371 of International PCT Application No. PCT/US2013/057822, filed Sep. 3, 2013, which claims the benefit of U.S. Patent Application No. 61/771,409, filed on Mar. 1, 2013, and U.S. Patent Application No. 61/696,083, filed on Aug. 31, 2012. The disclosure of these prior applications are incorporated by reference in their entirety.

FIELD

This disclosure relates to patient specific implant technology.

BACKGROUND

Implant (e.g., knee) systems have been sized based on medical imaging, cadaver dissection, and lessons learned from prior implant designs. In typical implant surgery (e.g., Total Knee Arthroplasty (TKA)), bones are cut to fit implant dimensions. In TKA, femur bones are cut to fit implants with an anterior cut, a distal chamfer cut, a distal cut, a posterior chamfer cut, and a posterior cut. In a resurfacing case, the bone cuts may be contoured to follow the original articular surface curvature or shape to some degree compared to the planar cuts in conventional TKA. Because a limited scope of implant sizes are available in implant (e.g., knee) systems, compromises are made in placing implants, such as allowing more resected bone to extend beyond the implant perimeter or for the implant to overhang beyond the resected bone. The mismatches between implant and bone may negatively impact patient outcomes, potentially resulting in additional blood loss, soft tissue risk, and post-operative pain.

SUMMARY

In one aspect, a system includes at least one processor and at least one computer-readable medium coupled to the at least one processor having stored thereon instructions which, when executed by the at least one processor, causes the at least one processor to perform operations. The operations include accessing a three-dimensional model of at least a portion of a bone, defining a three-dimensional solution volume based on resection cuts used in fitting an implant on the portion of the bone, and intersecting the three-dimensional model of the portion of the bone with the three-dimensional solution volume to produce a resultant bone volume represented in three dimensions. The operations also include determining an outline representation of at least a portion of an outer surface of a periphery of the resultant bone volume and using the outline representation in one or more operations related to implant matching.

Implementations may include one or more of the following features. For example, the operations may include accessing one or more images of the portion of the bone and generating the three-dimensional model of the portion of the bone based on the one or more images of the portion of the bone. The operations also may include defining a three-dimensional tolerance volume based on one or more tolerances for one or more variations related to an implant procedure for placing the implant on the portion of the bone and intersecting the three-dimensional model of the portion of the bone with the three-dimensional tolerance volume to produce the resultant bone volume represented in three dimensions. The operations further may include defining the three-dimensional tolerance volume based on at least one of a tolerance related to variations in surgical technique in performing the implant procedure, a tolerance related to variations in medical instrumentation used in performing the implant procedure, a tolerance related to variations in manufacturing the implant used in the implant procedure, a tolerance related to variations in anatomy of similar bones across patients, a tolerance related to variations in medical imaging used in generating the three-dimensional model of the portion of the bone, and a tolerance related to variations in file conversion used in generating the three-dimensional model of the portion of the bone In some implementations, the operations may include identifying the one or more tolerances for the one or more variations related to the implant procedure, determining one or more measurements that account for the one or more tolerances identified, and determining locations of resection cuts used in fitting the implant on the portion of the bone. In these implementations, the operations may include defining the three-dimensional tolerance volume based on the locations of the resection cuts and the one or more measurements that account for the one or more tolerances identified.

In addition, the operations may include aligning the three-dimensional solution volume on a portion of the three-dimensional model of the portion of the bone using techniques designed to optimize placement of an articular surface of the implant when placed on the portion of the bone. The operations may include evaluating the resultant bone volume with respect to one or more rules related to placing the implant on the portion of the bone.

In some examples, the operations may include determining whether the resultant bone volume is sufficient for fitting the implant in a manner that provides sufficient contact with the implant and an acceptable position of an articular surface of the implant. In these examples, the operations may include maintaining the resultant bone volume without adjustment based on a determination that the resultant bone volume is sufficient for fitting the implant in a manner that provides sufficient contact with the implant and an acceptable position of an articular surface of the implant. The determination of whether the resultant bone volume is sufficient for fitting the implant may be a determination of whether the implant optimally fills the space left by the resected bone (e.g., fills the space within a threshold degree of closeness).

In some implementations, the operations may include adjusting the resultant bone volume based on the evaluation of the resultant bone volume with respect to one or more rules related to placing the implant on the portion of the bone and determining an outline representation of at least a portion of an outer surface of a periphery of the resultant bone volume after adjustment. In these implementations, the operations may include defining an acceptable zone based on a periphery of the implant, intersecting the resultant bone volume with the acceptable zone to produce an acceptable bone volume, and adjusting the resultant bone volume based on the acceptable bone volume. Further, in these implementations, defining an implant tolerance zone based on sizing of the implant and one or more tolerances for one or more variations related to an implant procedure for placing the implant on the portion of the bone, intersecting the resultant bone volume with the implant tolerance zone to produce an overlap bone volume, and adjusting the resultant bone volume based on the overlap bone volume.

In some examples, the operations may include defining an acceptable zone based on a periphery of the implant and intersecting the resultant bone volume with the acceptable zone to produce an acceptable bone volume. In these examples, the operations may include defining an implant tolerance zone based on sizing of the implant and one or more tolerances for one or more variations related to an implant procedure for placing the implant on the portion of the bone and intersecting the resultant bone volume with the implant tolerance zone to produce an overlap bone volume. Further, in these examples, the operations may include combining the acceptable bone volume with the overlap bone volume to produce a composite bone volume and using the composite bone volume to generate an adjusted bone volume that defines inner and outer tolerance in three dimensions.

Also, the operations may include creating a bone surface ribbon from the outer surface of the periphery of the resultant bone volume and using the bone surface ribbon in one or more operations related to implant matching. The operations may include fitting a curve to the bone surface ribbon and using the curve fitted to the bone surface ribbon in one or more operations related to implant matching. The operations further may include designing a custom implant based on the outline representation.

In some implementations, the operations may include storing the outline representation in a database with sample outline representations determined for other bone portions that correspond to the portion of the bone, analyzing characteristics of the outline representations stored in the database, and, based on the analysis, clustering the outline representations stored in the database into multiple groups that each includes outline representations having similar characteristics. In these implementations, the operations may include defining an implant design for each of the multiple groups and, for each implant design, storing the implant design in association with one or more parameters that enable matching of the implant design with patient bone data.

In some examples, the operations may include determining one or more parameters of the outline representation, comparing the one or more parameters of the outline representation to parameters associated with available implant designs, and, based on comparison results, determining that the one or more parameters of the outline representation match an available implant design within a threshold degree. In these examples, the operations may include outputting the available implant design as matching the outline representation based on the determination that the one or more parameters of the outline representation match the available implant design within the threshold degree.

In some implementations, the operations may include determining one or more parameters of the outline representation, comparing the one or more parameters of the outline representation to parameters associated with available implant designs, and, based on comparison results, determining that the one or more parameters of the outline representation do not match an available implant design within a threshold degree. In these implementations, the operations may include, based on the determination that the one or more parameters of the outline representation do not match an available implant design within the threshold degree, determining that a custom implant is needed and outputting a message that indicates a custom implant is needed.

In another aspect, a method includes accessing a three-dimensional model of at least a portion of a bone, defining a three-dimensional solution volume based on resection cuts used in fitting an implant on the portion of the bone, and intersecting the three-dimensional model of the portion of the bone with the three-dimensional solution volume to produce a resultant bone volume represented in three dimensions. The method also includes determining, by at least one processor, an outline representation of at least a portion of an outer surface of a periphery of the resultant bone volume and using the outline representation in one or more operations related to implant matching.

In yet another aspect, at least one computer-readable storage medium is encoded with executable instructions that, when executed by at least one processor, cause the at least one processor to perform operations. The operations include accessing a three-dimensional model of at least a portion of a bone, defining a three-dimensional solution volume based on resection cuts used in fitting an implant on the portion of the bone, and intersecting the three-dimensional model of the portion of the bone with the three-dimensional solution volume to produce a resultant bone volume represented in three dimensions. The operations also include determining an outline representation of at least a portion of an outer surface of a periphery of the resultant bone volume and using the outline representation in one or more operations related to implant matching.

In another aspect, an instrument for locating a medial-lateral position of an implant includes a distal cut surface portion, an anterior chamfer portion connected to the distal cut surface portion, and an anterior flange portion connected to the anterior chamfer portion. The instrument also includes a posterior chamfer portion connected to the distal cut surface portion, at least one paddle connected to the posterior chamfer portion, and at least one locating hole in the distal cut surface portion. The distal cut surface portion has a lateral perimeter and a medial perimeter, and the lateral and medial perimeters each have a patient specific shape.

Implementations may include one or more of the following features. For example, the instrument may include a notch. The notch may be a posterior stabilizing box geometry. The posterior chamfer portion may include a posterior lateral chamfer and a posterior medial chamfer. The at least one paddle may include a posterior medial condyle and a posterior lateral condyle.

In addition, the instrument may include a patient specific implant with a perimeter, where at least the medial and lateral perimeters match a portion of the shape of the patient specific implant perimeter. The instrument also may include at least one pin hole. The least one pin hole may be circular.

Further, the least one locating hole may be circular. The least one locating hole may be selected from a group consisting of holes, slots, overlapping holes, or combination slots that allow for variance in the medial-lateral and anterior-posterior directions. The instrument may include a stiffener. The instrument may include articular surfaces.

In yet another aspect, an instrument for locating a medial-lateral position of an implant on a distal portion of a femur that has an overall width includes a distal cut surface portion having a maximum width, an anterior chamfer portion connected to the distal cut surface portion, and an anterior flange portion connected to the anterior chamfer portion. The instrument also includes a posterior chamfer portion connected to the distal cut surface potion, at least one paddle connected to the posterior chamfer portion, and at least one locating hole in the distal cut surface portion. The distal cut surface portion is centered relative to the overall width of the distal portion of the femur.

In a further aspect, a method for locating an implant includes preparing a distal end of a femur, locating a maximum distal width of the distal end, and placing an instrument on the prepared femur. The instrument includes a distal cut surface portion, an anterior chamfer portion connected to the distal cut surface portion, and an anterior flange portion connected to the anterior chamfer portion. The instrument also includes a posterior chamfer portion connected to the distal cut surface portion and at least one paddle connected to the posterior chamfer portion. The method also includes moving the instrument in a medial-lateral direction to obtain equal perimeter offsets, pinning the instrument, and creating at least one lug hole in the distal end of the femur using the instrument.

Implementations may include one or more of the following features. For example, the step of creating at least one lug may use a drill, a reamer or a punch. In addition, the method may include the steps of removing the instrument and implanting a knee prosthesis.

In another aspect, a method for manufacturing an instrument may include obtaining image data, generating a ribbon using the image data, and generating a spline using the ribbon. The method also includes generating offset distances for at least one lug location and importing the spline into an instrument CAD model. The method further includes placing the offset distances in the instrument CAD model and outputting the instrument CAD model to an electronic format suitable for rapid manufacturing/additive manufacturing production equipment, such as a SLA file.

The details of one or more implementations are set forth in the accompanying drawings and the description, below. Other potential features of the disclosure will be apparent from the description and drawings, and from the claims.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIGS. 2 and 50 are diagrams of example systems.

DETAILED DESCRIPTION OF THE EMBODIMENTS

The following description of the preferred embodiment(s) is merely exemplary in nature and is in no way intended to limit the invention, its application, or uses.

Techniques are described for defining a set of implant sizes (e.g., knee implant sizes) that more accurately and completely fit bone resections made during a surgical procedure (e.g., TKA). In defining the set of implant sizes, variability in bone resections (e.g., surgeon and instrumentation variation) and manufacturing variation (e.g., manufacturing tolerances) may be taken into account.

In some implementations, a broader range of implant sizes may be generated by varying the perimeter of the implant to more closely match a broader population of patients. In cases where the broader range of sizes does not fit well enough, a "custom" implant may be made using the same techniques used to make the discrete sizes in the broader size offering. In addition, in some examples, instrument sizes may be designed to more accurately and completely fit bone resections made during a surgical procedure (e.g., TKA). In these examples, the instrument sizes may be designed using techniques similar to those discussed throughout the application for implant sizes. The instrument sizes may be designed in addition to implant sizes or as an alternative to implant sizes.

In some examples, medical imaging (e.g., magnetic resonance imaging (MRI), computed tomography (CT), X-ray, Ultra-sound, etc.) is used to create a three-dimensional (3D) model of the patient's bone using various Computer Aided Design (CAD) processes. In these examples, using analytical techniques (e.g. statistical shape analysis, 3D coordinate analysis, matrix mathematical analysis, etc.) and summing process, anatomical, and surgical variations (e.g., tolerances or errors from a variety of sources), a 3D volume is modeled to intersect with the patient bone model, and a solution volume is created that sums these tolerances into a composite tolerance solution space. Further, in these examples, a bone surface ribbon is created from the solution volume and a BSpline is overlaid on the bone surface ribbon. The BSpline defines one new 3D solution curve that may be extruded to or from the instrument model template (e.g., additive and/or subtractive processes) to create a new instrument perimeter size. To further refine the solution, similarly shaped perimeters may be grouped together in subsets or clusters of cases from which a final single solution size may be statistically derived.

Figure 1:
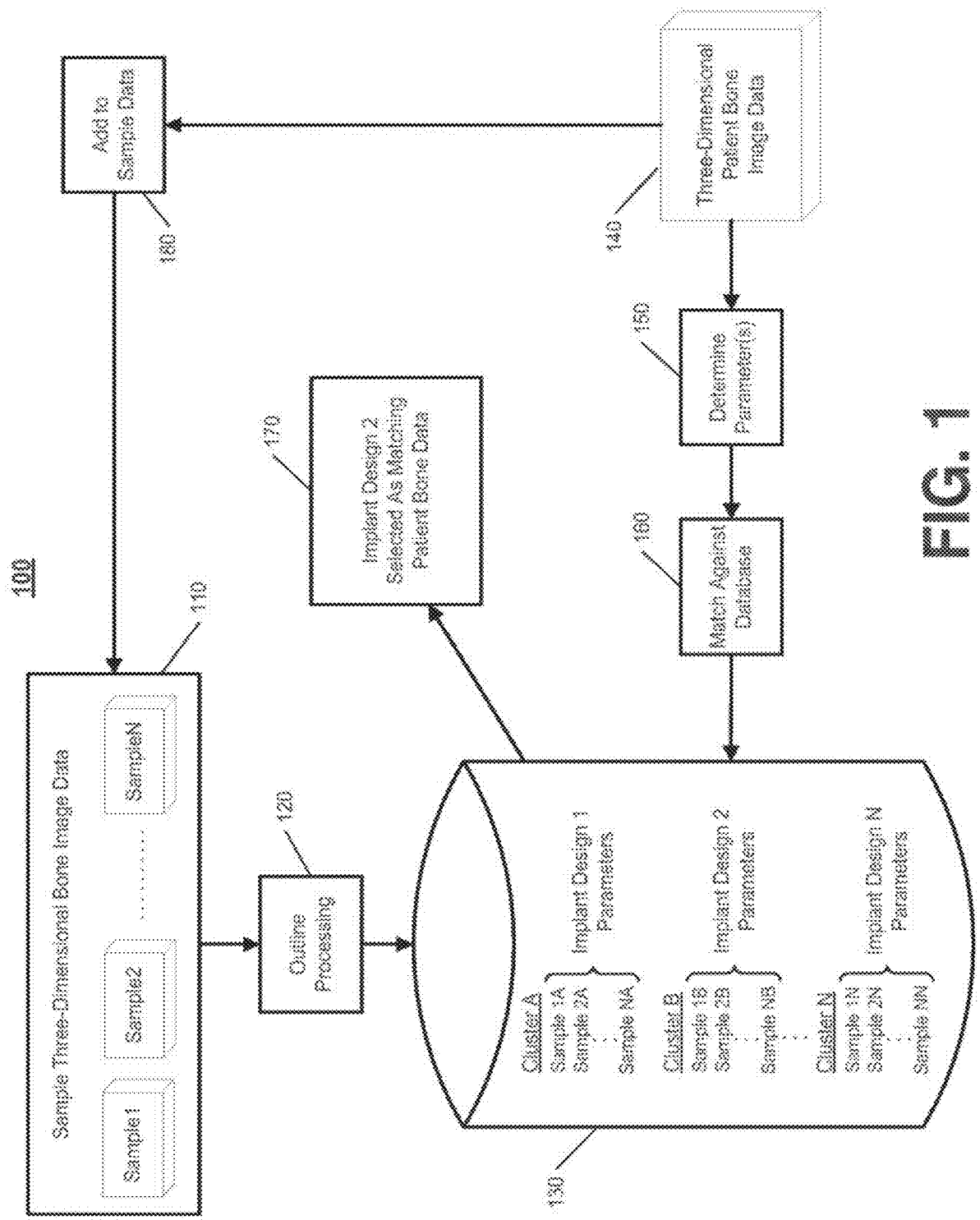
FIG. 1 is a diagram of an example approach for performing patient specific implant matching.

FIG. 1 illustrates an example approach 100 for performing patient specific implant matching. In the example approach 100, a system maintains a data repository 110 of sample three-dimensional bone image data. The data repository 110 may include many samples of three-dimensional bone image data taken from patients that have undergone or considered an implant procedure and/or from cadavers as part of a cadaver study. The three-dimensional bone image data may include images of at least a portion of a bone that include three-dimensional data or three-dimensional bone models generated based on three-dimensional image data or other measurements of the portion of the bone. Each sample of three-dimensional bone image data included in the data repository 110 corresponds to the same type of bone.

The system performs outline processing 120 on the samples of three-dimensional bone image data stored in the repository 110. For example, the system accesses a sample of three-dimensional bone image data and determines an outline representation of an outer surface of a periphery of the bone represented in the sample. In this example, the system may use the techniques described below with respect to FIGS. 3-15 to determine the outline representation.

After performing outline processing 120 on the samples of three-dimensional bone image data stored in the repository 110, the system stores outline representations of the samples in a database 130 used for a library of implant designs. Once a significant number of outline representations have been stored in the database 130, the system clusters the outline representations into groups having similar characteristics. Although three groups of outline representations are shown in FIG. 1 for brevity, many more groups of outline representations may result from clustering the outline representations stored in the database 130. The system may use the techniques described below with respect to FIG. 16 to cluster the outline representations.

After clustering the outline representations into multiple groups, the system defines an implant design for each group of outline representations and stores parameters that identify the implant design that corresponds to the group and that enable the implant design to be matched against patient bone data. The parameters may define size and shape characteristics of a range of outline representations that match a size and shape of the implant design. The system may use the techniques described below with respect to FIG. 16 to define implant designs for each group and store parameters associated with the defined implant designs.

In some examples, the database 130 defines a library of implant designs that provides a match within a threshold degree for a relatively large percentage of the population (e.g., seventy percent, eighty percent, ninety percent, etc.). In these examples, the high degree of coverage may be obtained by considering a large number of samples in the data repository 110 and clustering the outline representations into many different groups within the database 130. In determining the degree of coverage, a patient may be deemed as covered by library of implant designs based on an implant design in the library being within a threshold match to the patient in terms of a type of fit, such as millimeter gap from perimeter, percentage of surface area covered, or discrepancies at key landmarks. The system may be controlled to balance the degree of coverage offered by the library of implant designs with the cost of manufacturing standard implants for each of the groups within the database. For instance, the system may define an implant design for a particular group of outline representations only when the number of outline representations within the group reaches a threshold number that justifies definition of a new implant design. Over time, the degree of coverage offered by the library of implant designs may continue to expand as more and more bone data is collected and analyzed. As the library of implant designs expands, the library of implant designs may offer patient specific implant matching solutions to more and more patients.

The system may use the library of implant designs stored in the database 130 to select an implant design for a patient. For example, the system accesses three-dimensional bone data 140 for a patient, determines one or more parameters 150 of the three-dimensional bone data 140, and matches 160 the one or more parameters against the database 130. In this example, the system may determine an outline representation of the three-dimensional bone data 140 and use the outline representation of the three-dimensional bone data 140 to match against the database 130. The system may use the techniques described below with respect to FIG. 17 to determine 150 one or more parameters of the three-dimensional bone data 140 and match 160 the one or more parameters against the database 130.

The one or more parameters of the three-dimensional bone data 140 may include any aspect of the three-dimensional bone data 140 that relates to fit of an implant to the bone. For example, the one or more parameters may include sensitivity to cut location, slope, and likeliness for overhang. In this example, the system matches the sensitivity to cut location, slope, and/or likeliness for overhang against the database 130.

When the system determines that the one or more parameters of the three-dimensional bone data 140 matches an implant design stored in the library, the system outputs a message 170 indicating that a match has been found. In the example shown in FIG. 1, the message 170 indicates that the second implant design has been selected as matching the patient bone data. In this regard, because the system selects an implant design that matches the patient bone data within a threshold degree, the system provides a patient specific implant (or near patient specific implant) using a standard implant design without having to generate a custom implant. Because the system does not have to generate a custom implant, the cost and time related to obtaining a patient specific implant (or near patient specific implant) may be reduced.

In some implementations, the system defines custom implants using the same techniques described above. In these implementations, the system may pull modeling features to create the custom implant solution.

In addition to selecting an implant design for the patient, the system also adds 180 the three-dimensional bone data 140 to the data repository 110. Accordingly, the system is able to continue to collect additional sample data, which the system may use to redefine the implant designs included in the library stored in the database 130. As additional data is collected (e.g., when a threshold number of new samples has been collected), the system repeats the clustering and implant design definition operations discussed above. In this regard, the system is able to routinely update the library of implant designs to add new implant designs to cover new groups of patients and/or modify existing designs to better cover a group of patients or cover a larger group of patients. With these updates, the library of implant designs may expand and provide better coverage of the general population.

Figure 2:
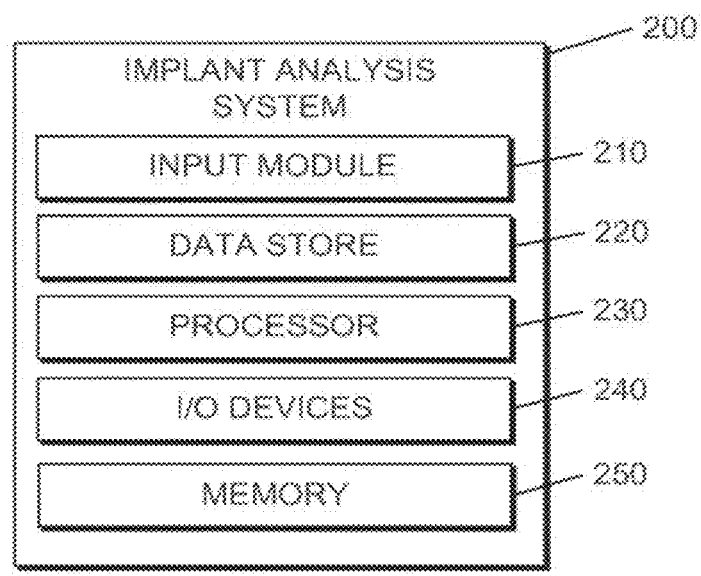

FIG. 2 illustrates an example implant analysis system 200, which may be used as the system referenced above with respect to FIG. 1. The system 200 includes an input module 210, a data store 220, one or more processors 230, one or more I/O (Input/Output) devices 240, and memory 250. The input module 220 may be used to input any type of information used in implant matching and processing. For example, the input module 210 may be used to receive bone data and parameters related to implant matching. In some implementations, data from the input module 210 is stored in the data store 220. The data included in the data store 220 may include, for example, any type of implant related data (e.g., bone images, three-dimensional models of bones, parameters related to implant designs, outline representations of a bone volume, etc.).

In some examples, the data store 220 may be a relational database that logically organizes data into a series of database tables. Each database table in the data store 220 may arrange data in a series of columns (where each column represents an attribute of the data stored in the database) and rows (where each row represents attribute values). In some implementations, the data store 220 may be an object-oriented database that logically or physically organizes data into a series of objects. Each object may be associated with a series of attribute values. In some examples, the data store 220 may be a type of database management system that is not necessarily a relational or object-oriented database. For example, a series of XML (Extensible Mark-up Language) files or documents may be used, where each XML file or document includes attributes and attribute values. Data included in the data store 220 may be identified by a unique identifier such that data related to a particular process may be retrieved from the data store 220.

The processor 230 may be a processor suitable for the execution of a computer program such as a general or special purpose microprocessor, and any one or more processors of any kind of digital computer. In some implementations, the system 200 includes more than one processor 230. The processor 230 may receive instructions and data from the memory 250. The memory 250 may store instructions and data corresponding to any or all of the components of the system 200. The memory 250 may include read-only memory, random-access memory, or both.

The I/O devices 240 are configured to provide input to and output from the system 200. For example, the I/O devices 240 may include a mouse, a keyboard, a stylus, or any other device that allows the input of data. The I/O devices 240 may also include a display, a printer, a 3D Printer, such as an SLS 3D printing machine that prints metal parts from a CAD file, or any other device that outputs data.

Figure 3:
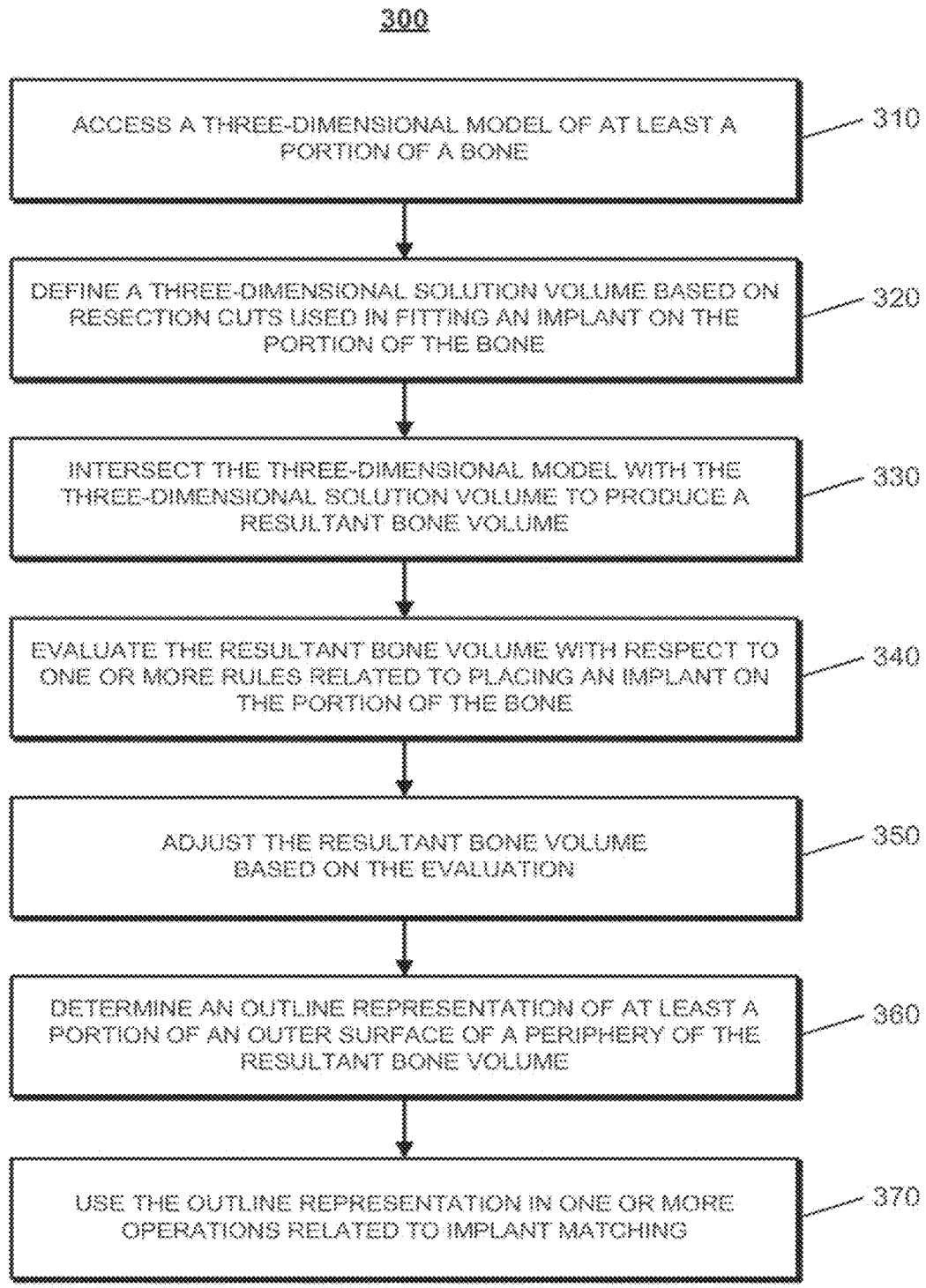
FIGS. 3, 4, 7, 16, 17, 29, 33, and 34 are flowcharts of example processes.

FIG. 3 illustrates a process 300 used in implant matching. The operations of the process 300 are described generally as being performed by the system 200. In some implementations, operations of the process 300 may be performed by one or more processors included in one or more electronic devices.

The system 200 accesses a three-dimensional model of at least a portion of a bone (310). For example, the system 200 may access a three-dimensional model of an entire bone or a portion of a bone that was generated based on medical measuring of a bone of a patient. In this example, the system 200 may receive the three-dimensional model from another system that generates the three-dimensional model by processing medical measurements taken of the bone or the portion of the bone. The medical measurements may be determined based on medical imaging of the bone or other physical measuring of the bone using medical instrumentation.

In some examples, the system 200 generates the three-dimensional model of an entire bone or a portion of a bone based on medical measuring of the bone of the patient. In these examples, the system 200 may access one or more images of the portion of the bone and generate the three-dimensional model of the portion of the bone based on the one or more images of the portion of the bone. The one or more images of the portion of the bone may be captured using MRI, CT, X-ray, Ultra-sound, or other medical imaging technology. The system 200 may access the one or more images of the portion of the bone from another system or may capture the one or more images of the portion of the bone through control of an imaging device.

In some implementations, the system 200 may access MRI images that depict multiple slices of the portion of the bone. In these implementations, the system 200 may digitally create a mask of the MRI slices and stitch the MRI slices together to create a solid model. Further, in these implementations, the system 200 may remove errors and smooth the data representing the solid model of the portion of the bone. In smoothing the data, the system 200 may select a minimum tool radius to eliminate all smaller internal radii along the surface, including divots and wrinkles. The system 200 may use the smoothed version of the solid model of the portion of the bone as the three-dimensional model of the portion of the bone. The application of a minimum tool radius to the shape of a three-dimensional model, curve, other spline forms, or inflexion points at intersections of these geometric forms may be applied to the bone model or later to the implant model.

In implementations in which the techniques described throughout this disclosure are used in knee implants (e.g., TKA), the system 200 accesses a three-dimensional model of at least a portion of a femur and/or a tibia. For instance, the system 200 may access a three-dimensional model of an entire femur or tibia, or may access a three-dimensional model of a portion of the femur or tibia located at the knee joint (e.g., the portion of the femur or tibia that receives an implant during TKA). In addition, the techniques described throughout this disclosure may be applied to other types of implant procedures (e.g., hip replacement, shoulder replacement, etc.). For other types of implant procedures, the system 200 may access a three-dimensional model of a portion of the bone that receives the implant, such as a portion of the bone located at a joint associated with the implant procedure. In some implementations, a more comprehensive anatomical system also may be used that includes, for example, the entire leg, pelvis, and spine. In these implementations, by analyzing the entire system, the alignment of femur and tibia bone resections simulated by the system 200 may be altered to account for motion of the knee joint taking into account input(s) from the entire anatomical system.

The system 200 defines a three-dimensional solution volume based on resection cuts used in fitting an implant on the portion of the bone (320). For example, the system 200 identifies a location of a plane of each resection cut needed to place an implant on the portion of the bone and defines a model that represents the locations of the resection cuts relative to one another. In this example, the model that represents the locations of the resection cuts relative to one another may define each plane representing a resection cut as having a width component and a height component.

In some implementations, to identify the location of the plane of each resection cut needed to place the implant on the portion of the bone and define the model that represents the locations of the resection cuts relative to one another, the system 200 determines one or more size measurements of the portion of the bone and selects, from a library of standard implants, a standard implant appropriate for the one or more size measurements of the portion of the bone. In these implementations, the system 200 accesses size and shape measurements for the standard implant selected and uses the accessed size and shape measurements to identify the location of the plane of each resection cut needed to place the implant on the portion of the bone and define the model that represents the locations of the resection cuts relative to one another. For instance, the system 200 defines the model to correspond to surfaces of the standard implant that contact the portion of the bone after the implant has been placed on the portion of the bone.

To create the three-dimensional solution volume, the system 200 may add a thickness around each of the resection cuts to define a three-dimensional model in which each plane representing a resection cut has a width component, a height component, and a thickness component. The shape of the volume represents at least a portion of the set of all possible bone resections. In this regard, the volume may be oblong or trapezoidal. The volume also may be tube-shaped, spherical, or bone-shaped or relatively prismoidal, as in a traditional saw blade resection. The three-dimensional model may define a three-dimensional geometric shape that encompasses an area where resection cuts are made to fit the implant on the portion of the bone. In adding the thickness around each of the resection cuts, the system 200 may add the thickness uniformly on each side of the resection cut or may add the thickness disproportionately on sides of the resection cuts. The system 200 may consider the curvature of the bone and implant restrictions to set the thickness added to each resection cut and a distribution of the selected thickness on sides of each resection cut. In considering the curvature of the bone, the system 200 may use the curvature of the bone as part of the clustering and/or to partly drive the slope of the final implant design.

In some implementations, the system 200 may apply draft angle around the perimeter of the implant to match or more closely match adjacent bone slope. In these implementations, the system 200 attempts to match the draft angle of an implant perimeter trim sheet in a 3D CAD model to adjacent bone/cartilage slope. For instance, the system 200 stores data indicating draft angle for particular clusters of bones and then uses the stored draft angle data to match draft angle for the particular clusters of bones. Draft angle matching may be applicable to a variety of applications including knee femoral, tibial, and possibly patellar implants, other joints (e.g., hip, ankle, shoulder, elbow, wrist, etc.), spine, plates (e.g., trauma, cranial, etc.), and prosthetic implant devices for the purpose of skeletal reconstruction (e.g., cosmetic facial reconstruction following an injury). A draft angle may be used in such a way to avoid overhanging sharp edge features that could adversely affect adjacent soft tissues. Applying the composite tolerance volume approach described throughout this disclosure may ensure the sharp edge overhang risk is mitigated. Benefits of using a draft angle in this way may include reducing unintended ligament strain by more closely matching the geometry of native bone in the joint or in other areas of the patient's anatomy as in a cranial plate or a cosmetic facial reconstruction implant. In areas where soft tissues wrap around the edge of an implant, more closely matching the native shape of the bone, and minimizing raised implant perimeter height and corner radii (CAD model "blends"), may further reduce risk of irritation, abrasion, or strain in adjacent soft tissue structures.

In some implementations, the system 200 may use patient specific draft angles, or draft angles determined from analysis, e.g. clustering analysis, of previous knee cases in the database. The system 200 may use a "standard library of implants" with many more sizes than previous knee implant systems with improved draft angles around the perimeter of the resection cuts. In these implementations, the system 200 may fit future patients with implants that more closely match resected bone volumes to implant volumes. This may benefit patients by more closely matching soft tissue (ligament) balance in the knee joint and preserving or improving Range Of Motion (ROM) in the knee joint. In addition to adding draft angles to the perimeter, the system 200 also may increase the blend radii between the implant articular surfaces and the draft angle perimeter surfaces. Increasing the blend radii also may aid in more closely matching bone resection volume to implant volume.

In some examples, the system 200 may apply thickness (e.g., two millimeters) along an entire portion of each resection cut. In these examples, the system 200 may define each resection cut as a rectangular box and arrange the rectangular boxes at appropriate positions adjacent one another to define a three-dimensional box cut as the three-dimensional solution volume.

Figure 5:
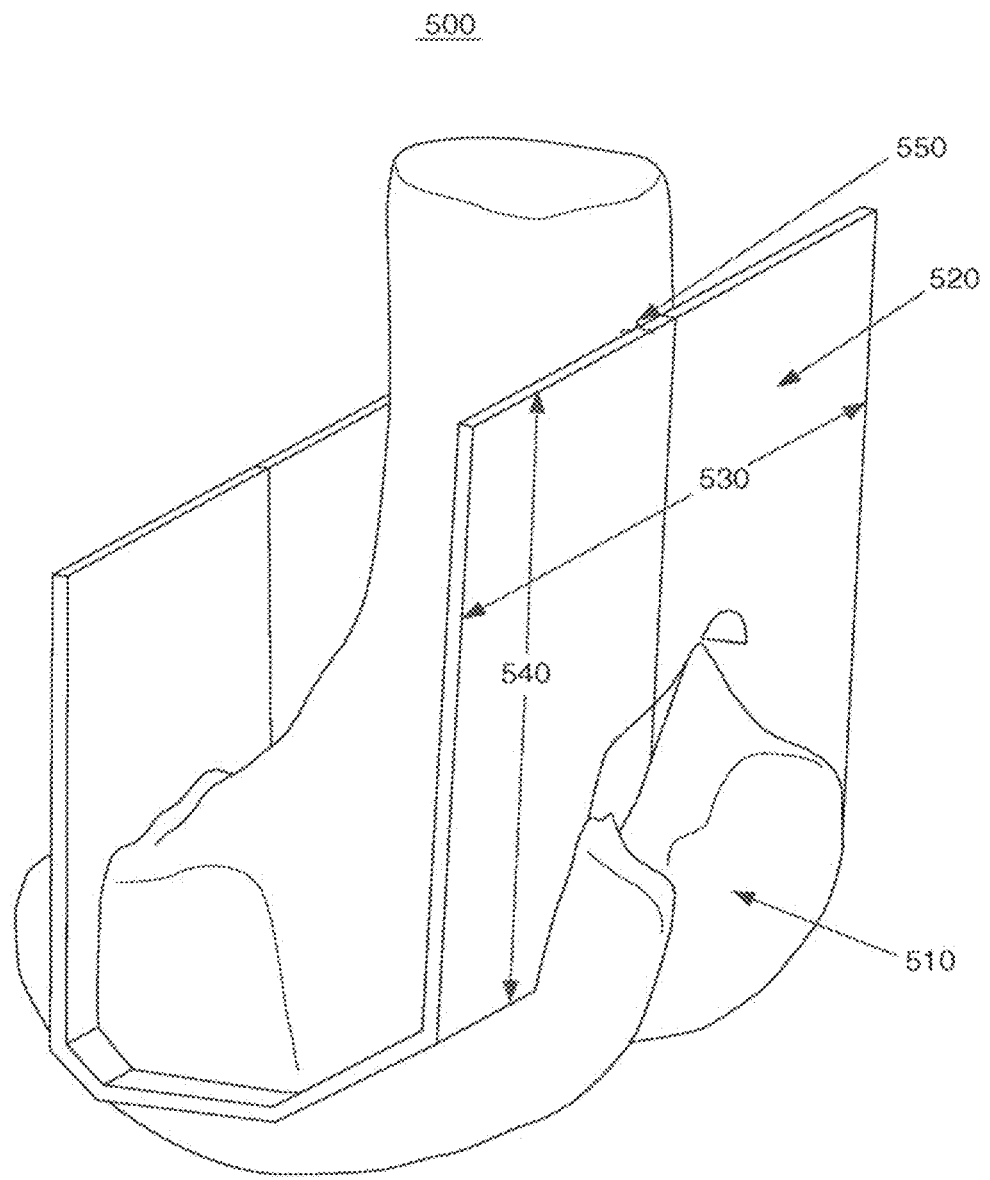
FIGS. 5, 6, 8-15, 18, 28, and 35-49 are diagrams of example interfaces.

For example, FIG. 5 illustrates an example interface 500 that shows a three-dimensional solution volume 520 that has a thickness of two millimeters. As shown, the three-dimensional solution volume 520 represents a three-dimensional box cut, which includes a rectangular box defined at each resection cut made to a distal end of a femur in TKA. For instance, the three-dimensional solution volume 520 has a first rectangular box defined at an anterior cut, a second rectangular box defined at a distal chamfer cut, a third rectangular box defined at a distal cut, a fourth rectangular box defined at a posterior chamfer cut, and a fifth rectangular box defined at a posterior cut. The first, second, third, fourth, and fifth rectangular boxes are arranged at appropriate positions adjacent one another to define a three-dimensional box cut as the three-dimensional solution volume 520. The three-dimensional solution volume 520 may be one component of a composite solution volume, which includes a bone model volume, a contact area volume (e.g., from implant system designs), a manufacturing tolerance volume, an inspection tolerance volume, a surgeon variation volume, and other volumes that represent other variability factors.

Each of the rectangular boxes that define the three-dimensional solution volume 520 has a width component, a height component, and a thickness component. For instance, as shown in FIG. 5, the first rectangular box defined at the anterior cut has a width component 530, a height component 540, and a thickness component 550. The width component 530 and the height component 540 are defined based on a plane of the anterior cut and the thickness component 550 is defined by adding thickness around the plane of the anterior cut.

In addition, the system 200 may apply different thicknesses to different resection cuts such that the system 200 defines the three-dimensional box cut with rectangular boxes having different thickness components. Further, the system 200 may apply different thicknesses along a particular resection cut. In this regard, the particular resection cut is represented by a three-dimensional shape other than a rectangular box. The system 200 may determine the thickness to apply along each portion of each resection cut based on the curvature of the bone and implant restrictions. The system 200 also may, additionally or alternatively, determine the thickness to apply along each portion of each resection cut based on tolerances related to a procedure for fitting the implant on the portion of the bone, as discussed in more detail below.

In implementations in which the techniques described throughout this disclosure are used in knee implants (e.g., TKA), the system 200 may define a model that includes a plane for each of an anterior cut, a distal chamfer cut, a distal cut, a posterior chamfer cut, and a posterior cut needed to fit an implant on a distal end of a femur. For each of the anterior cut, the distal chamfer cut, the distal cut, the posterior chamfer cut, and the posterior cut, the system 200 may add a thickness component proportionately on each side to define a rectangular box cut that includes a rectangular box for each of the anterior cut, the distal chamfer cut, the distal cut, the posterior chamfer cut, and the posterior cut.

In some implementations, the system 200 may use additional cuts as the implant system requires. For instance, another knee system may require several anterior chamfer planes. The system 200 also may consider additional patient specific matching in the cruciate gap of the femur, and the anatomical features on the tibia and patella for a TKA.

In addition, the system 200 may consider corresponding anatomical features in other joints, spine, or other skeletal structures. The system 200 may apply the techniques described throughout this disclosure to other extremities and surgical systems, such as IM nails, trauma plates/screws, cranial plates, cosmetic surgical prostheses, etc. The system 200 may apply the techniques described throughout this disclosure to any surgical procedure where the system 200 can identify the geometry of an anatomical structure and apply it to a medical product design to give a patient specific solution.

Further, the "cuts" referred to in this disclosure may actually be planes defined by the implant. For example, a surgeon may cut the bone large (resulting in smaller bone cut shape) and then impact a nominally sized implant onto the bone—compacting the surface down. In this example, the implant periphery might be made to fit the press-fit resection. However, the implant interfaces with all of the crushed bone and might ideally be made to match the bone shape at its final impacted location. Thus, the "cuts" referred to in this disclosure represent the planes of the implant, rather than the actual cuts made during the surgical procedure.

In some examples, the system 200 defines a three-dimensional tolerance volume based on one or more tolerances for one or more variations related to an implant procedure for placing the implant on the portion of the bone. In these examples, the system 200 may select the thickness to add to each resection cut based on the one or more tolerances for the one or more variations related to an implant procedure for placing the implant on the portion of the bone. The system 200 may select the thickness to cover a range of variations that may occur during an implant procedure due to surgeon error, manufacturing tolerances in manufacturing the implant, variations in medical instrumentation, and variations in modeling the portion of the bone in determining a placement of the implant.

In addition, bone curvature may represent bone variation and may influence a particular tolerance. For example, tolerance on the side of the bone where it is relatively steep would be more sensitive than a tolerance applied to a relatively flat bony feature.

Figure 4:
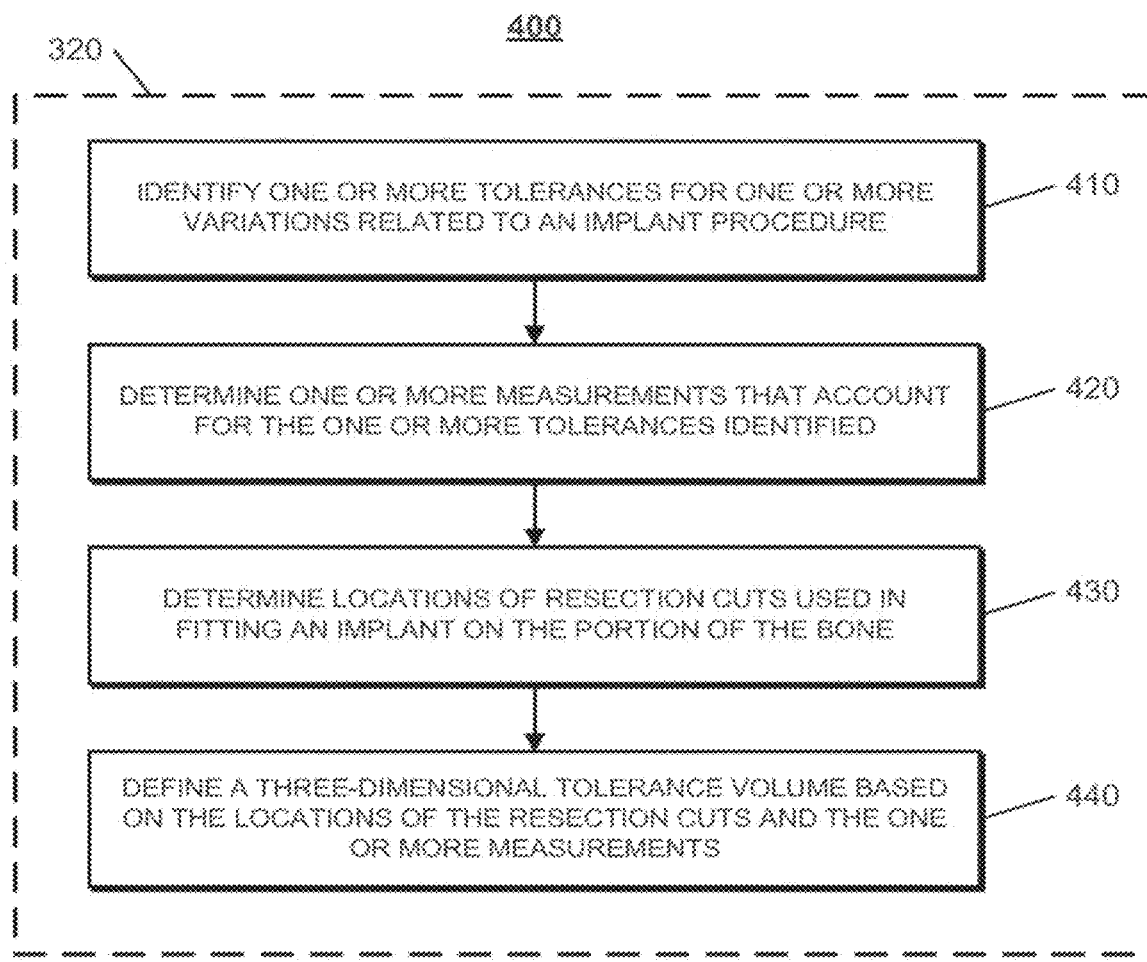

FIG. 4 illustrates a process 400 for defining a three-dimensional tolerance volume. The process 400 may be used in defining a three-dimensional solution volume based on resection cuts used in fitting an implant on the portion of the bone referenced above with respect to reference numeral 320. The operations of the process 400 are described generally as being performed by the system 200. In some implementations, operations of the process 400 may be performed by one or more processors included in one or more electronic devices.

The system 200 identifies one or more tolerances for one or more variations related to an implant procedure for placing the implant on the portion of the bone (410). For example, the system 200 may identify tolerances for any combination of variations, such as surgical variations and manufacturing variations, which control how accurately an implant procedure can be performed. In this example, the system 200 may determine a first tolerance related to variations in surgical technique in performing the implant procedure (e.g., tolerances in an ability of a surgeon to make perfect incisions and cuts), a second tolerance related to variations in medical instrumentation used in performing the implant procedure (e.g., tolerances in instrument manufacturing and wear), a third tolerance related to variations in manufacturing the implant used in the implant procedure (e.g., manufacturing tolerances in how well an implant is made), a fourth tolerance related to variations in anatomy of similar bones across patients, a fifth tolerance related to variations in medical imaging used in generating the three-dimensional model of the portion of the bone (e.g., variation due to limitations on resolution of an imaging device), and a sixth tolerance related to variations in file conversion used in generating the three-dimensional model of the portion of the bone (e.g., variations that may be introduced when an original image file is converted into another format). The system 200 may use any combination of one or more of the first tolerance, the second tolerance, the third tolerance, the fourth tolerance, the fifth tolerance, and the sixth tolerance in defining the three-dimensional tolerance volume. Also, the fifth tolerance related to variations in medical imaging may include two components of medical imaging variation: (1) database source data (e.g., imaging used to design the implant) and (2) new patient data (e.g., imaging of the patient receiving the patient specific implant).

In some implementations, the system 200 may determine the tolerances of variations based on general historical data related to implant procedures tracked over time. In these implementations, the system 200 may generally account for manufacturing tolerances, surgeon error, imaging tolerances, and file conversion tolerances without analyzing the specific implant device or instrument used in the implant procedure, the surgeon performing the implant procedure, the imaging technology used to image the bone, or the specific file conversions needed in modeling the bone. Accordingly, in these implementations, the system 200 may account for tolerances related to variations associated with an implant procedure by applying the same adjustments to each patient being evaluated. In addition, the system 200 may determine the selection of how these objectives or rules are implemented based on ethnicity and other demographic or lifestyle metrics.

In other implementations, the system 200 may account for tolerances related to variations associated with an implant procedure by tailoring adjustments to a specific implant procedure being evaluated. In these implementations, the system 200 may consider a tolerance of a specific surgeon performing the implant procedure, a tolerance that accounts for manufacturing variation and wear of the medical instruments to be used in the implant procedure, and a tolerance that accounts for variation in the medical imaging and image processing operations performed in planning the implant procedure. By accounting for the tolerances specific to the implant procedure, the system 200 may provide a more accurate adjustment for the potential variations associated with the implant procedure. The system 200 may determine the specific tolerances by receiving user input describing the tolerances or by receiving user input describing characteristics of the implant procedure (e.g., surgeon name, equipment being used, imaging device being used, file conversion being performed in planning, instrument and implant materials, material wear rates, manufacturing processes, inspection processes, etc.) and using the inputted characteristics of the implant procedure to determine the tolerances specific to the implant procedure.

The system 200 determines one or more measurements that account for the one or more tolerances identified (420). The system 200 may take a view of a total continuum of tolerances related to the implant procedure and account for all of them in determining one or more measurements to use in generating the three-dimensional tolerance volume. In doing so, the system 200 may weigh the different tolerance values based on a degree of accuracy known for each tolerance value and a degree of possible variation known for each tolerance value. In addition, the system 200 may consider a single tolerance value (or a subset of tolerance values) in determining one or more measurements to use in generating the three-dimensional tolerance volume. The single tolerance value (or the subset of tolerance values) may be selected based on a degree of variation associated with the tolerance value. For instance, tolerance related to surgeon error may be selected because a relatively high degree of variation may result from surgeon error, as compared to other tolerances related to the implant procedure.

The system 200 may determine one or more measurements that account for the one or more tolerances identified by determining a thickness to add to each resection cut in defining the tolerance volume. In determining a thickness to add to each resection cut in defining the tolerance volume, the system 200 may determine a thickness that accounts for the tolerance of each potential variation considered. For example, the system 200 may determine a thickness of 0.2 mm to account for medical imaging based on an MRI imaging device having a tolerance of one pixel with a pixel size of 0.2 mm. In another example, the system 200 may determine a thickness of 1.0 mm (e.g., +/−1.0 mm) to account for surgeon error based on a review of post-surgical data and/or surgeon comments indicating that surgeons are, on average, accurate to within 1.0 mm for resection cuts. After determining a thickness that accounts for the tolerance of each potential variation considered, the system 200 may sum all of the thicknesses to account for the worst case scenario in defining the tolerance volume. Alternatively, the system 200 may combine the thicknesses in a manner that accounts for the probability of each variation occurring and to what degree. For instance, the system 200 may calculate a root mean square of the thicknesses and use the result as the thickness added to the resection cuts in the tolerance volume. The system 200 also may consider a distribution of errors related to the implant procedure and determine a measurement that accounts for a particular variation based on Monte Carlo analysis of sample errors for the particular variation collected over time. In addition, the probability of each variation could relate to the likelihood of any of the inputs described, including clusters of bones. As the system 200 makes compromises between the resulting ribbons, the system 200 chooses a compromise that is most likely to match known and unknown bone shapes. For example, the system 200 may overlap ribbons and probability distributions assigned to those ribbons. In this example, the overlap between the ribbons would consequently be overlap between probability distributions as well. The combined probabilities (e.g., summed) gives the system 200 a target that is better for the group even if it sub-optimal for individual group members.

The system 200 determines locations of resection cuts used in fitting the implant on the portion of the bone (430). For example, the system 200 determines a location of a plane of each resection cut needed to place the implant on the portion of the bone. In this example, the system 200 may determine the location of the resection cuts based on a shape of the portion of the bone and/or a shape of typical resection cuts needed to fit an implant on the portion of the bone. The system 200 may use size and shape measurements of a standard implant to determine locations of resection cuts, as discussed above with respect to reference numeral 320.

The system 200 defines the three-dimensional tolerance volume based on the locations of the resection cuts and the one or more measurements that account for the one or more tolerances identified (440). For example, the system 200 may define a model of the resection cuts based on the locations of the resection cuts. In this example, the system 200 then may use the one or more measurements to add a thickness around each of the resection cuts in the model of the resection cuts to define a three-dimensional model of the resection cuts in which each resection cut has a width component, a height component, and a thickness component. In this regard, the three-dimensional model may define a three-dimensional geometric shape that encompasses an area where resection cuts may occur in consideration of the tolerances of the variations related to the implant procedure. In adding the thickness around each of the resection cuts, the system 200 may add the thickness uniformly on each side of the resection cut (e.g., assume a perfect cut and expand the three-dimensional tolerance volume equal distances on each side of the perfect cut). In addition, the system 200 may add the thickness disproportionately on sides of the resection cuts. The system 200 may consider the curvature of the bone and implant restrictions in addition to the tolerances to set the thickness added to each resection cut and a distribution of the selected thickness on sides of each resection cut.

In some examples, in accounting for tolerances, the system 200 may apply the same thickness (e.g., two millimeters) along an entire portion of each resection cut. In these examples, the system 200 may define each resection cut as a rectangular box and arrange the rectangular boxes at appropriate positions adjacent one another to define a three-dimensional box cut as the three-dimensional model of the resection cuts.

In addition, the system 200 may apply different thicknesses to different resection cuts such that the system 200 defines the three-dimensional box cut with rectangular boxes having different thickness components. For example, the tolerance related to surgeon error may be lower for a first of the resection cuts as compared to a second of the resection cuts. In this example, the system 200 may use a first thickness for the first of the resection cuts that is smaller than a second thickness used for the second of the resection cuts.

Further, the system 200 may apply different thicknesses along a particular resection cut. In this regard, the particular resection cut is represented by a three-dimensional shape other than a rectangular box. The system 200 may use different thicknesses along a particular resection cut if the tolerance for variations differs along the resection cut. For instance, the tolerance for surgeon error may gradually increase from a start of the particular resection cut to an end of the particular resection cut. In this instance, the system 200 may gradually increase a thickness used along the particular resection cut in defining the three-dimensional tolerance volume such that the portion of the three-dimensional tolerance volume corresponding to the particular resection cut has a cone shape.

The system 200 may determine the thickness to apply along each portion of each resection cut based on the curvature of the bone, implant restrictions, and the one or more measurements that account for the one or more tolerances identified. In this regard, the system 200 may adjust the one or more measurements that account for the one or more tolerances identified because the one or more measurements would result in issues with the curvature of the bone and/or violate restrictions on how the implant needs to be fit to the bone.

Referring again to FIG. 3, the system 200 intersects the three-dimensional model of the portion of the bone with the three-dimensional solution volume to produce a resultant bone volume represented in three dimensions (330). For instance, the system 200 may compare the three-dimensional solution volume to the three-dimensional model of the portion of the bone and determine an appropriate placement of the three-dimensional solution volume that aligns with locations where resection cuts would be made in placing an implant on the portion of the bone.

In aligning the three-dimensional solution volume, the system 200 may align the three-dimensional solution volume on a portion of the three-dimensional model of the portion of the bone using techniques designed to optimize placement of an articular surface of the implant when placed on the portion of the bone. Any type of technique for aligning the three-dimensional solution volume in a manner that optimizes placement of an articular surface of the implant may be used. For example, the system 200 may consider six degrees of freedom (e.g., three location distances and three rotations) in aligning the three-dimensional solution volume and may consider various aspects of the anatomy of the patient in selecting the alignment. In this example, the system 200 may consider a size and shape of the portion of the bone, a biomechanical axis relevant to the implant procedure, and appropriate motions (or ranges of motion) for a joint associated with the portion of the bone. In considering the size and shape of the portion of the bone, the system 200 may consider the size and shape of the piece of bone being analyzed within the solution volume and/or consider the size and shape categorically. For instance, the system 200 may consider the resultant shape of sub-sampling a bone and/or may consider pristine bone shapes or geometric primitive(s).

In implementations in which the techniques described throughout this disclosure are used in knee implants (e.g., TKA), the system 200 may consider the varus-valgus angles, the flexion-extension angles, the rotation positions, and any other parameters relevant to placement of an implant on the portion of the bone that results in optimized use of the knee after the implant procedure. In implementations in which the techniques described throughout this disclosure are used in other types of implants (e.g., spherically shaped hip joint bones, flat shoulder components, or saddle-shaped ankle joints), the system 200 may consider characteristics relevant to placing the other types of implants.

As shown in FIG. 5, the example interface 500 shows a three-dimensional model of a portion of a bone 510 intersected with the three-dimensional solution volume 520. As shown, the three-dimensional solution volume 520 intersects the three-dimensional model of a portion of a bone 510 at positions where resection cuts would be made in fitting an implant on the portion of the bone. In this example, the three-dimensional model of the portion of the bone 510 models a distal end of a femur and the three-dimensional solution volume 520 corresponds to resection cuts needed to place a femoral component of a knee implant on the distal end of the femur modeled by the three-dimensional model 510.

After aligning the three-dimensional solution volume on the three-dimensional model of the portion of the bone, the system 200 may extract the portion of the three-dimensional model of the portion of the bone that intersects with the three-dimensional solution volume. For instance, the system 200 may remove portions of the three-dimensional model of the portion of the bone that are outside of the three-dimensional solution volume, thereby leaving the portion of the three-dimensional model of the portion of the bone that intersects with the three-dimensional solution volume. The system 200 may use the portion of the three-dimensional model of the portion of the bone that intersects with the three-dimensional solution volume as the resultant bone volume, which is represented in three dimensions.

Figure 6:
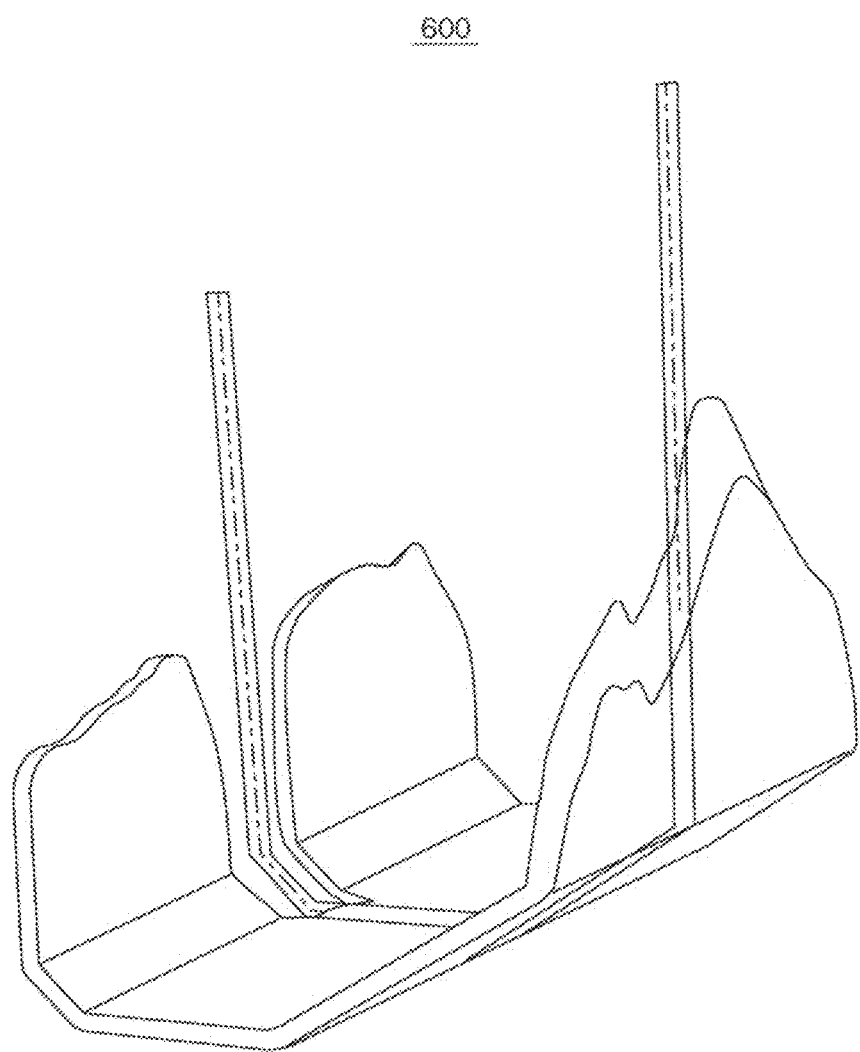

FIG. 6 illustrates an example interface 600 that shows a resultant bone volume represented in three dimensions. The resultant bone volume shown in the interface 600 is a result of intersecting the three-dimensional solution volume 520 with the three-dimensional model of the portion of the bone 510, as shown in FIG. 5. The resultant bone volume shown in the interface 600 models a shape (e.g., an anterior flange profile, profiles of the chamfer cuts, a distal cut profile, and a posterior cut profile) of what an outer surface of the bone would like after resection cuts are made to the bone due to the tolerances.

Referring again to FIG. 3, the system 200 evaluates the resultant bone volume with respect to one or more rules related to placing the implant on the portion of the bone (340) and adjusts the resultant bone volume based on the evaluation of the resultant bone volume with respect to one or more rules related to placing the implant on the portion of the bone (350). For example, the system 200 may access rules that define how the implant should be placed on the bone to conform to preferred medical practices, what the shape of the implant should be to conform to preferred medical practices, and restrictions placed on the implant size due to manufacturing constraints. In this example, the system 200 evaluates the resultant bone volume against the accessed rules and determines whether an implant fitted to portions of the resultant bone volume would violate one or more of the accessed rules. Based on a determination that an implant fitted to portions of the resultant bone volume complies with all of the accessed rules, the system 200 maintains the resultant bone volume without adjustment.

Based on a determination that an implant fitted to portions of the resultant bone volume would violate one or more of the accessed rules, the system 200 determines whether the portions of the resultant bone volume can be adjusted in a manner that complies with the accessed rules. Based on a determination that the portions of the resultant bone volume can be adjusted in a manner that complies with the accessed rules, the system 200 adjusts the resultant bone volume (e.g., reshapes or removes portions of the resultant bone volume) in a manner that complies with the accessed rules. Based on a determination that the portions of the resultant bone volume cannot be adjusted in a manner that complies with the accessed rules, the system 200 provides an alert that indicates that the resultant bone volume violates one or more of the accessed rules and cannot be adjusted to comply with the accessed rules.

In some implementations, the rules related to placing the implant on the portion of the bone define an amount of contact needed to secure the implant to the bone in accordance with preferred medical practices. In these implementations, the system 200 may access a minimum contact rule that specifies a minimum contact area needed to stably secure the implant on the portion of the bone. The system 200 compares the minimum contact area defined by the minimum contact rule with the resultant bone volume and, based on the comparison, determines whether all portions of the resultant bone volume meet the minimum contact area. Based on a determination that all portions of the resultant bone volume meet the minimum contact area, the system 200 maintains the resultant bone volume without adjustment. However, based on a determination that portions of the resultant bone volume do not meet the minimum contact area, the system 200 adjusts the resultant bone volume by removing or reshaping the portions of the resultant bone volume that do not meet the minimum contact area.

In addition, the rules related to placing the implant on the portion of the bone may define an acceptable position of an articular surface of the implant in accordance with preferred medical practices. For example, the system 200 may access a rule that specifies a position and/or shape of an articular surface of the implant that is needed for an acceptable surgical result. In this example, the system 200 compares the position and/or shape of the articular surface of the implant defined by the rule with the resultant bone volume and, based on the comparison, determines whether all portions of the resultant bone volume allow the implant to meet the position and/or shape of the articular surface of the implant defined by the rule. Based on a determination that all portions of the resultant bone volume meet the position and/or shape of the articular surface of the implant defined by the rule, the system 200 maintains the resultant bone volume without adjustment. However, based on a determination that portions of the resultant bone volume do not meet the position and/or shape of the articular surface of the implant defined by the rule, the system 200 adjusts the resultant bone volume by removing or reshaping the portions of the resultant bone volume that do not meet the position and/or shape of the articular surface of the implant defined by the rule. Adjusting the resultant bone volume to achieve an acceptable position and/or shape of an articular surface of the implant may be important because, although a better fit to the bone may be achieved, the bone may have problems that are being corrected through the implant procedure and the benefits of having an improved articular surface may outweigh the benefits of having a better fit to the bone.

In implementations in which the techniques described throughout this disclosure are used in knee implants (e.g., TKA), the system 200 may access a rule that specifies a position and/or shape of a cruciate gap of the implant that is needed for an acceptable surgical result. In this example, the system 200 compares the position and/or shape of the cruciate gap of the implant defined by the rule with the resultant bone volume and, based on the comparison, determines whether all portions of the resultant bone volume allow the implant to meet the position and/or shape of the cruciate gap of the implant defined by the rule. Based on a determination that all portions of the resultant bone volume meet the position and/or shape of the cruciate gap of the implant defined by the rule, the system 200 maintains the resultant bone volume without adjustment. However, based on a determination that portions of the resultant bone volume do not meet the position and/or shape of the cruciate gap of the implant defined by the rule, the system 200 adjusts the resultant bone volume by removing or reshaping the portions of the resultant bone volume that do not meet the position and/or shape of the cruciate gap of the implant defined by the rule. Adjusting the resultant bone volume to preserve the condylar width of the implant may be important to maintain acceptable articulation with respect to the patellar component and to allow for enhanced ease of the implant procedure by the surgeon. Adjusting the resultant bone volume to preserve the cruciate gap of the implant also may be useful.

In some examples, the rules related to placing the implant on the portion of the bone may define limitations on a risk of overhang allowed for the implant. For instance, the system 200 may access a rule that specifies how close the implant may be to an edge of the bone. The rule may have varying distances for different portions of the bone based on the probability and severity of a risk of overhang at the particular portion of the bone (e.g., the rule may define more conservative distances in locations near tissue where the risk of overhang is greater). The system 200 compares the distances defined by the rule with the resultant bone volume and, based on the comparison, determines whether all portions of the resultant bone volume allow the implant to meet the distances defined by the rule. Based on a determination that all portions of the resultant bone volume meet the distances defined by the rule, the system 200 maintains the resultant bone volume without adjustment. However, based on a determination that portions of the resultant bone volume do not meet the distances defined by the rule, the system 200 adjusts the resultant bone volume by removing or reshaping the portions of the resultant bone volume that do not meet the distances defined by the rule. Adjusting the resultant bone volume to limit the risk of overhang may be important because overhang may result in patient discomfort after the implant procedure and may outweigh the benefits of having a better fit to the bone.

In some implementations, the rules related to placing the implant on the portion of the bone may define limitations on a thickness of the implant. For example, the system 200 may access a rule that specifies a minimum thickness of the implant. In this example, the system 200 compares the thicknesses of an implant matched to the resultant bone volume to the minimum thickness and, based on the comparison, determines whether all portions of the resultant bone volume allow the implant to meet the minimum thickness defined by the rule. Based on a determination that all portions of the resultant bone volume meet the minimum thickness defined by the rule, the system 200 maintains the resultant bone volume without adjustment. However, based on a determination that portions of the resultant bone volume do not meet the minimum thickness defined by the rule, the system 200 adjusts the resultant bone volume by removing or reshaping the portions of the resultant bone volume that do not meet the minimum thickness defined by the rule. The system 200 also may change the position of the final implant on the bone so that a different portion of the bone is sampled (e.g., resampling). Adjusting the resultant bone volume to meet the minimum thickness may be important because the negatives of having a thin portion of the implant (e.g., a potentially sharp edge, decreased strength, etc.) may outweigh the benefits of having a better fit to the bone. Also, if matching bone volume affects articulation, e.g. kinematics of femur/tibia/patella motion, the system 200 may preserve some areas as "safe zones" to preserve stability of the knee joint. For example, the system 200 may preserve the trochlear groove on the femoral implant for patella tracking.

Further, the rules related to placing the implant on the portion of the bone may define limitations on a shape of an edge of the implant. For example, the system 200 may access a rule that specifies an acceptable contour of the implant. In this example, the system 200 compares the contour of an implant matched to the resultant bone volume to the acceptable contour and, based on the comparison, determines whether all portions of the resultant bone volume allow the implant to meet the acceptable contour defined by the rule. Based on a determination that all portions of the resultant bone volume meet the acceptable contour defined by the rule, the system 200 maintains the resultant bone volume without adjustment. However, based on a determination that portions of the resultant bone volume do not meet the acceptable contour defined by the rule, the system 200 adjusts the resultant bone volume by removing or reshaping the portions of the resultant bone volume that do not meet the acceptable contour defined by the rule. Adjusting the resultant bone volume to meet the acceptable contour may be important because the negatives of having a sharp part of the implant may outweigh the benefits of having a better fit to the bone.

Figure 7:
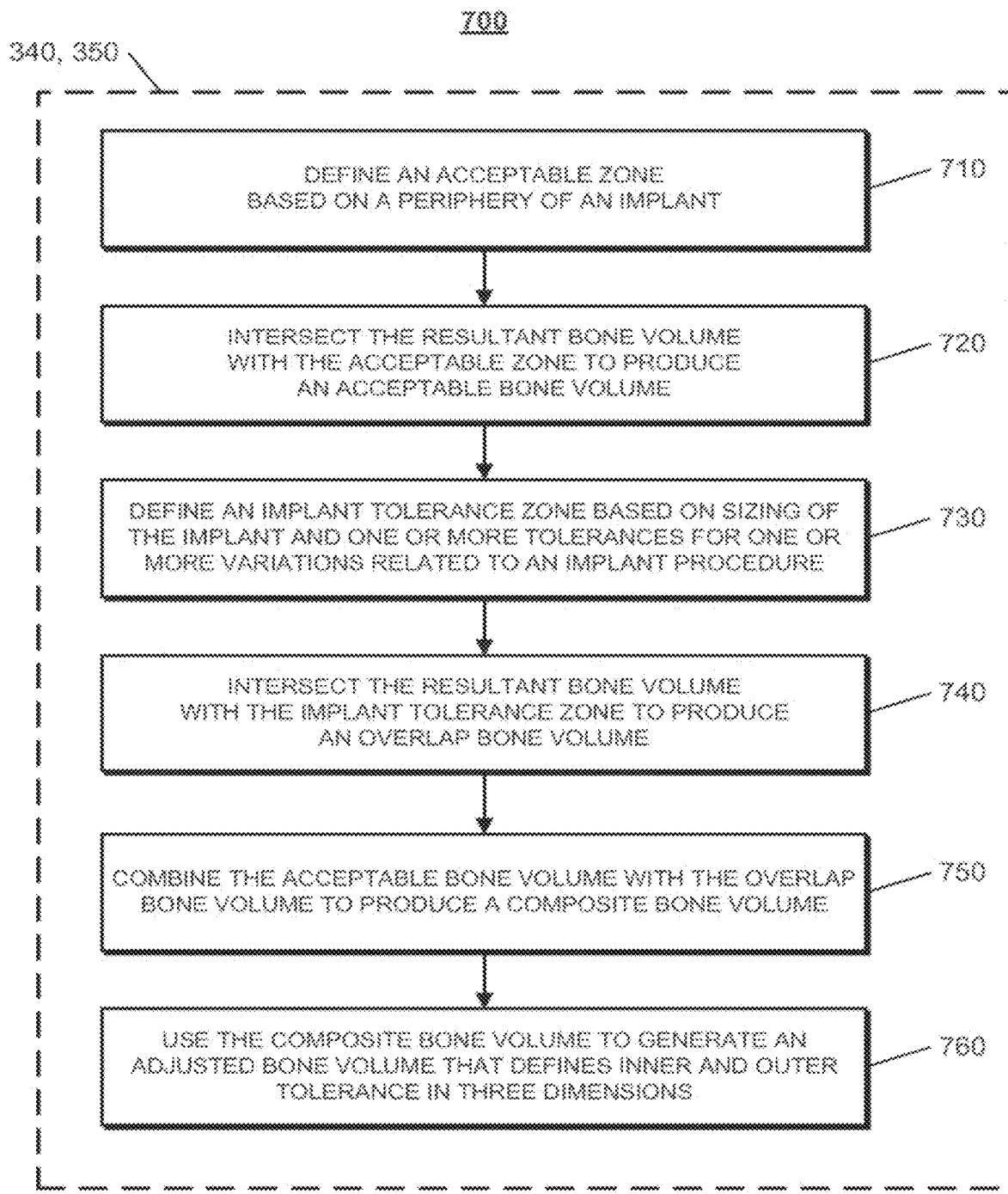

FIG. 7 illustrates a process 700 for generating an adjusted bone volume. The process 700 may be used in evaluating the resultant bone volume with respect to one or more rules related to placing the implant on the portion of the bone and adjusting the resultant bone volume based on the evaluation referenced above with respect to reference numerals 340 and 350. The operations of the process 700 are described generally as being performed by the system 200. In some implementations, operations of the process 700 may be performed by one or more processors included in one or more electronic devices.

The system 200 defines an acceptable zone based on a periphery of the implant (710). For instance, the system 200 uses the implant periphery to define a minimum acceptable zone, which may be smaller or larger than existing implants. The minimum acceptable zone may define a contact area of the implant needed to achieve an acceptable surgical result that conforms with preferred medical practices. The contact area may refer to the contact area between the femoral implant and the femur. The system 200 may define the minimum acceptable zone as a contact area volume that may be matched to the resultant bone volume. The contact area volume may define an area that accommodates a minimum size of articular surfaces of the implant.

The system 200 intersects the resultant bone volume with the acceptable zone to produce an acceptable bone volume (720). For instance, the system 200 may compare the resultant bone volume to the acceptable zone and, based on the comparison, align the acceptable zone on the resultant bone volume. The system 200 may align the acceptable zone on the resultant bone volume by matching one or more surfaces of the acceptable zone with one or more surfaces of the resultant bone volume.

Figure 8:
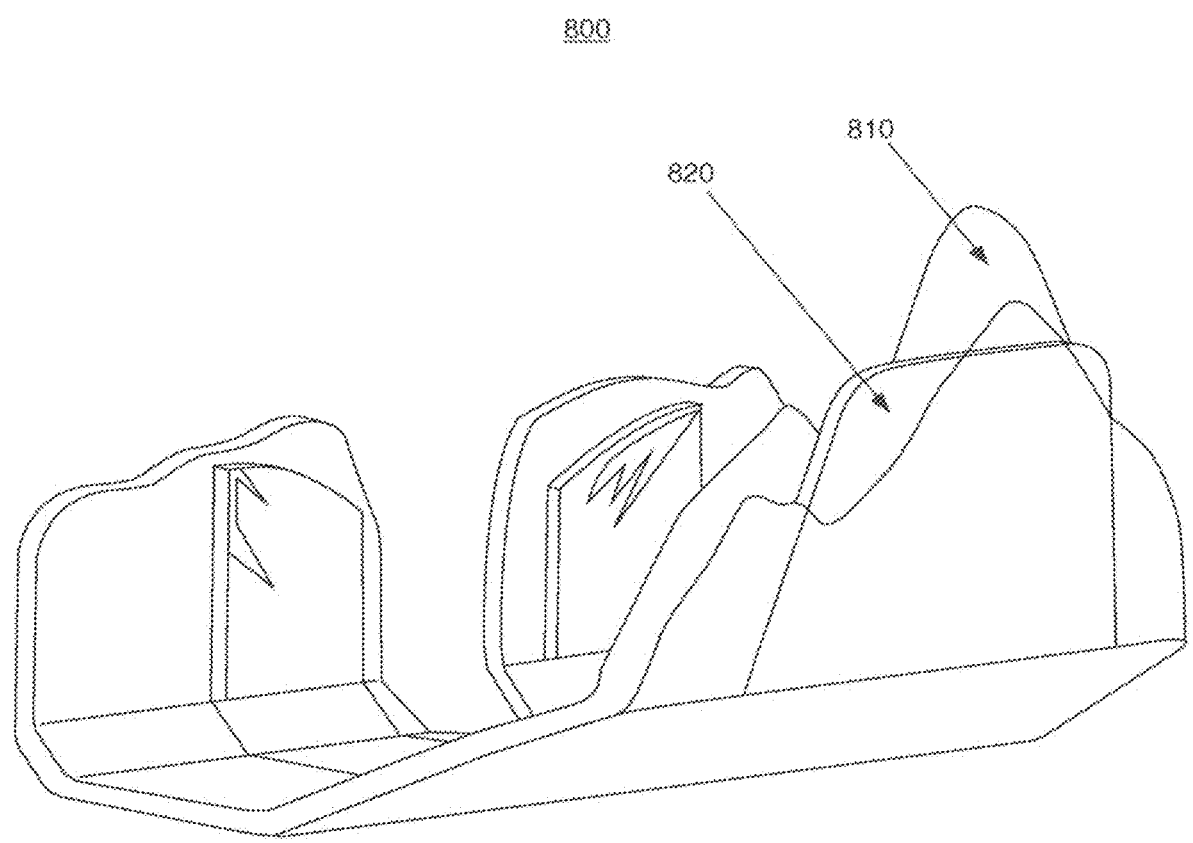

FIG. 8 illustrates an example interface 800 that shows a three-dimensional resultant bone volume 810 and a three-dimensional acceptable zone 820. As shown, the three-dimensional acceptable zone 820 intersects the three-dimensional resultant bone volume 810 with surfaces of the acceptable zone 820 aligned with surfaces of the resultant bone volume 810. The acceptable zone 820 corresponds to a minimum size to provide the necessary articular surfaces on the implant. Accordingly, the periphery of the acceptable zone 820 is added to the resultant bone volume 810 where the periphery of the acceptable zone 820 extends beyond the resultant bone volume 810. In some examples, the three-dimensional acceptable zone 820 may be a contact area safe zone. In these examples, the contact area is mapped to where the tibia and patella contact the femoral implant. In this regard, the system 200 protects this safe zone so the kinematics and durability of an implant system are not changed.

Referring again to FIG. 7, the system 200 defines an implant tolerance zone based on sizing of the implant and one or more tolerances for one or more variations related to an implant procedure for placing the implant on the portion of the bone (730). For example, the system 200 accesses size and shape data for a standard implant and defines the implant tolerance zone based on the size and shape data for the standard implant. In this example, the system 200 may extend the implant tolerance zone out from surfaces of the implant that contact the bone. The system 200 may define the implant tolerance zone using techniques similar to those described above for defining the three-dimensional tolerance volume (see, e.g., FIG. 4 and the corresponding description). The system 200 may define the implant tolerance zone to have the same volume as the three-dimensional tolerance volume described above.

Figure 9:
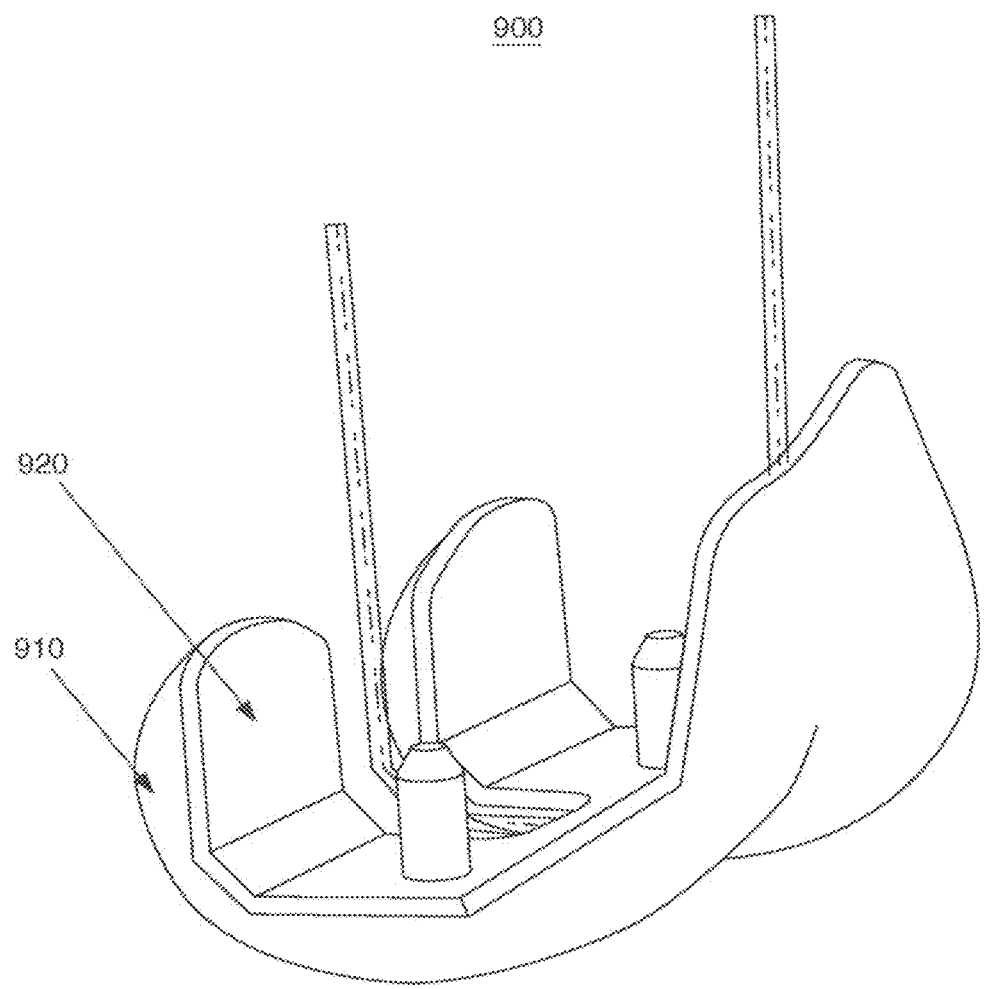

FIG. 9 illustrates an example interface 900 that shows a three-dimensional representation of an implant 910, which may correspond to the largest limits placed on the implant size due to manufacturing constraints, and a three-dimensional implant tolerance zone 920. As shown, the three-dimensional implant tolerance zone 920 extends out from surfaces of the implant 910 that contact the bone and represents a tolerance defined with respect to a size of the three-dimensional representation of the implant 910. The system 200 may define the three-dimensional implant tolerance zone 920 using the same or similar techniques to those described above with respect to defining the three-dimensional tolerance zone in FIG. 4.

Referring again to FIG. 7, the system 200 intersects the resultant bone volume with the implant tolerance zone to produce an overlap bone volume (740). For instance, the system 200 may compare the resultant bone volume to the implant tolerance zone and, based on the comparison, align the implant tolerance zone on the resultant bone volume. The system 200 may align the implant tolerance zone on the resultant bone volume by matching one or more surfaces of the implant tolerance zone with one or more surfaces of the resultant bone volume.

Figure 10:
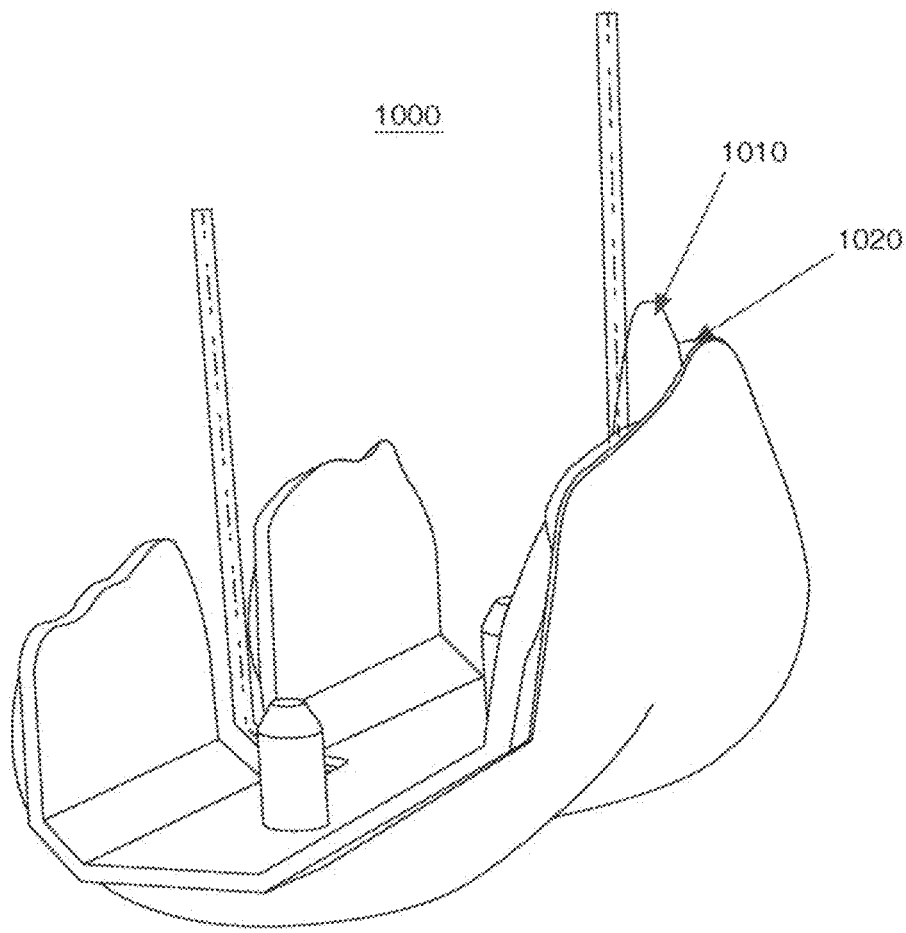

FIG. 10 illustrates an example interface 1000 that shows a three-dimensional resultant bone volume 1010 and a three-dimensional implant tolerance zone 1020. As shown, the three-dimensional implant tolerance zone 1020 intersects the three-dimensional resultant bone volume 1010 with surfaces of the implant tolerance zone 1020 aligned with surfaces of the resultant bone volume 1010. The implant tolerance zone 1020 defines limits on the three-dimensional resultant bone volume 1010. The system 200 may limit the resultant bone volume 1010 to a size that is within the implant tolerance zone 1020 to define a three-dimensional representation of an overlap bone volume. In the example shown in FIG. 10, the three-dimensional overlap bone volume represents an intersection of the resultant bone volume described above with respect to FIG. 6 with the implant tolerance zone 920 described above with respect to FIG. 9.

Referring again to FIG. 7, the system 200 combines the acceptable bone volume of FIG. 8 with the overlap bone volume of FIG. 10 to produce a composite bone volume (750). For instance, the system 200 may compare the acceptable bone volume to the overlap bone volume and, based on the comparison, align the acceptable bone volume on the overlap bone volume to produce the composite bone volume. The system 200 may align the acceptable bone volume on the overlap bone volume by matching one or more surfaces of the acceptable bone volume with one or more surfaces of the overlap bone volume.

Figure 11:
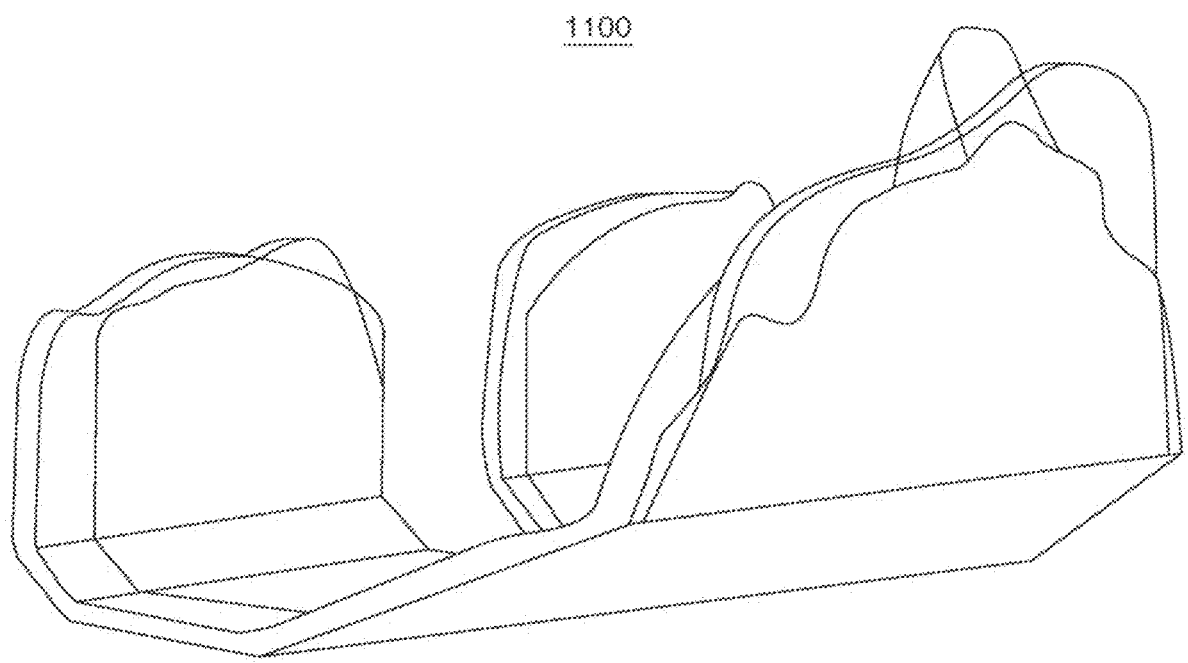

FIG. 11 illustrates an example interface 1100 that shows a three-dimensional representation of a composite bone volume in which an acceptable bone volume has been aligned on an overlap bone volume. In the example shown in FIG. 11, the composite bone volume has been defined based on a combination of the three-dimensional acceptable bone volume described above with respect to FIG. 8 with the overlap bone volume described above with respect to FIG. 10.

Referring again to FIG. 7, the system 200 uses the composite bone volume to generate an adjusted bone volume that defines inner and outer tolerance in three dimensions (760). For instance, the system 200 removes and/or reshapes portions of the composite bone volume that do not meet the acceptable zone and the implant tolerance zone. The system 200 may use the composite bone volume to define inner and outer acceptable three-dimensional tolerance for a particular region (e.g., the anterior flange of a distal end of a femur) or to define inner and outer acceptable three-dimensional tolerance for the entire implant and all associated faces/edges. Where needed, the system 200 may create an interpolation of the tolerance zone, which adds to the bone volume. The system 200 may produce an adjusted bone volume that results from removing and/or reshaping portions of the composite bone volume that do not meet the acceptable zone and the implant tolerance zone.

Figure 12:
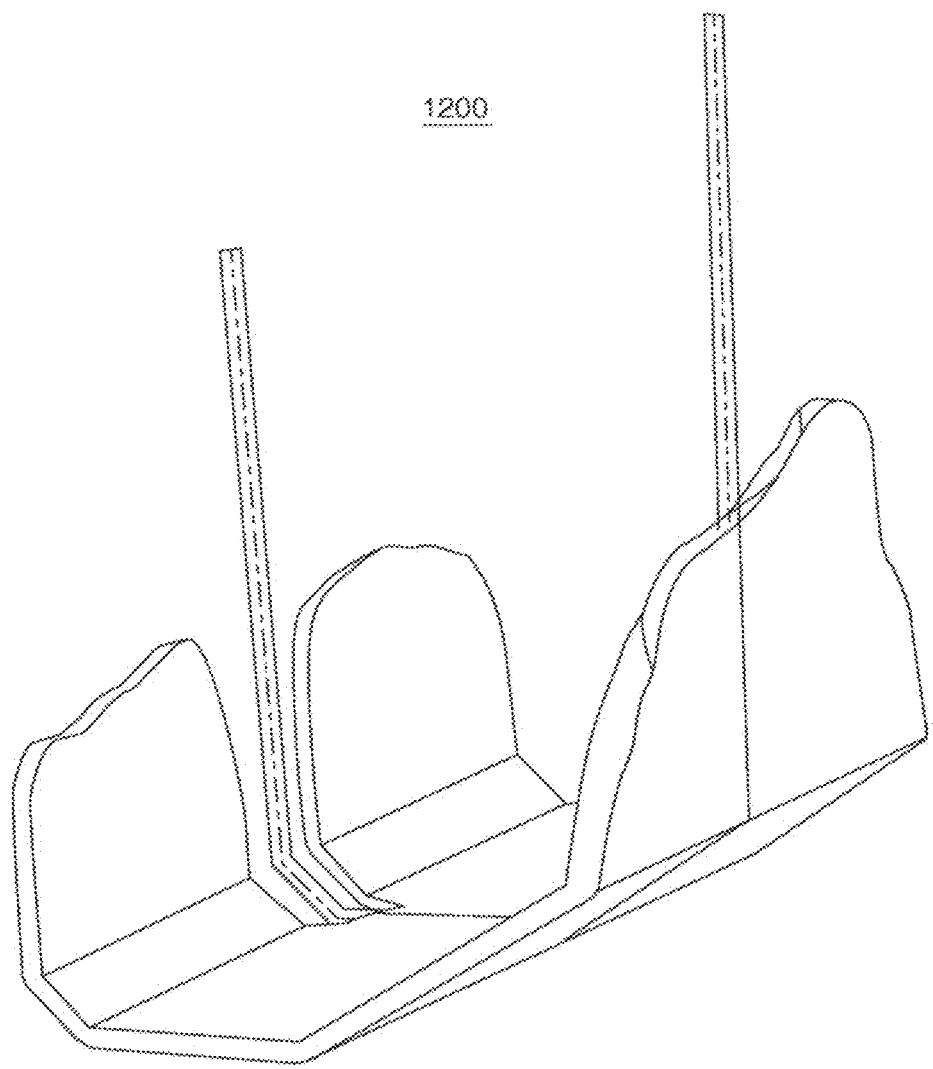

FIG. 12 illustrates an example interface 1200 that shows a three-dimensional representation of an adjusted bone volume. In the example shown in FIG. 12, the three-dimensional adjusted bone volume shows a bone volume adjusted in accordance with the composite bone volume described above with respect to FIG. 11. In this example, the system 200 removed portions of the composite bone volume that did not meet the implant tolerance zone and added portions to the composite bone volume where the composite bone volume did not meet the acceptable zone.

Referring again to FIG. 3, the system 200 determines an outline representation of at least a portion of an outer surface of a periphery of the resultant bone volume (360). For example, the system 200 may analyze the resultant bone volume (e.g., the adjusted bone volume described above) and identify an outer surface of a periphery of the resultant bone volume. In this example, the system 200 may extract, from the resultant bone volume, the outer surface of the periphery of the resultant bone volume to create a bone surface ribbon that models the outer surface of the periphery of the resultant bone volume. The bone surface ribbon may be represented in three dimensions and may represent an outer surface of an implant that best matches the portion of the bone being evaluated while accounting for the tolerances and rules described throughout this disclosure. The bone surface ribbon may be used as the outline representation.

Figure 13:
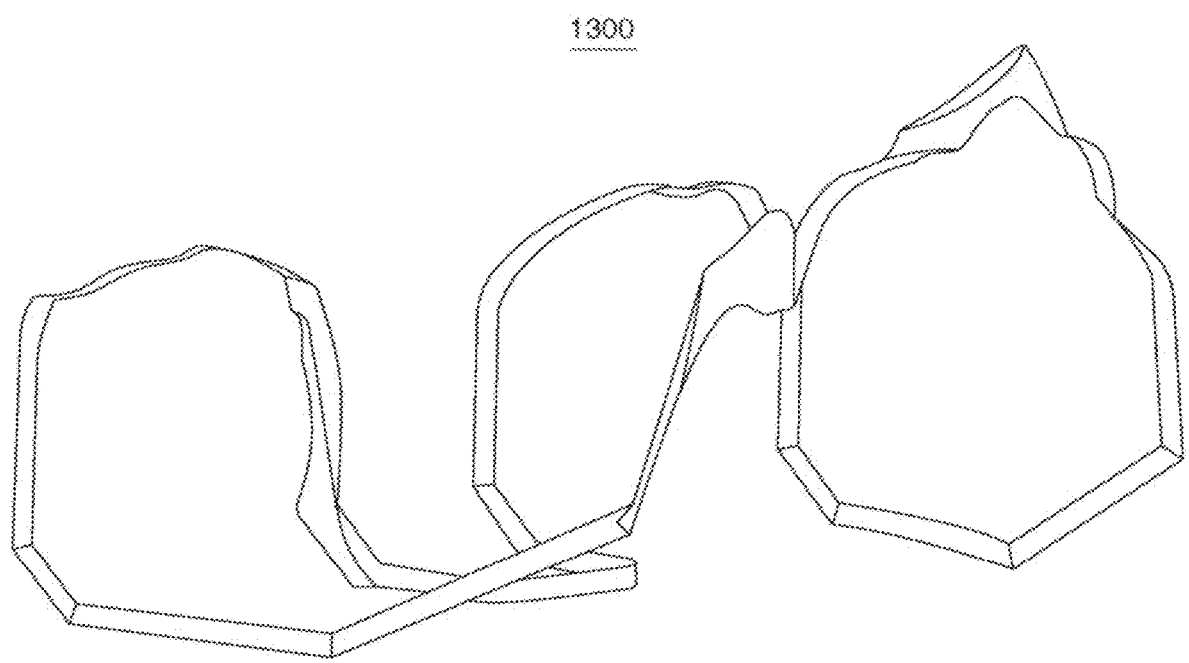

FIG. 13 illustrates an example interface 1300 that shows a bone surface ribbon. In the example shown in FIG. 13, the bone surface ribbon is a three-dimensional representation of an outer surface of a periphery of the adjusted bone volume shown in FIG. 12. In this example, the system 200 has extracted the bone surface ribbon from the adjusted bone volume shown in FIG. 12 to model a perimeter of an implant that best matches the adjusted bone volume shown in FIG. 12 while accounting for the tolerances and rules described throughout this disclosure.

In some implementations, the system 200 fits a curve to the bone surface ribbon to define the outline representation. In these implementations, the system 200 may use statistics or other appropriate techniques to select a shape for an implant to fit the bone surface ribbon and may fit a curve to the selected shape. For instance, the system 200 may create a curve that follows a sheet or tolerance volume represented by the bone surface ribbon. The system 200 may define the curve in three dimensions.

In some examples, the system 200 may fit a curve to the bone surface ribbon without limiting the curve to the surface of the ribbon. In these examples, the system 200 may allow the curve to extend inside and/or outside the bone surface ribbon within a tolerance value (e.g., two millimeters) and derive a curve that best matches the bone surface ribbon within the tolerance value. The system 200 may define the tolerance to a side of the bone surface ribbon that limits a potential for overhang of an implant created using the derived curve. For instance, to avoid overhang, the system 200 may only place the curve inside the bone surface ribbon, rather than outside the bone ribbon.

To fit a curve to the bone surface ribbon, the system 200 may overlay a BSpline (or other type of spline) on the bone surface ribbon. For instance, the system 200 may analyze the bone surface ribbon and, based on the analysis, identify locations on the bone surface ribbon appropriate for nodes of a spline. The system 200 then may create the spline by defining curves that model the bone surface ribbon between the identified nodes.

Figure 14:
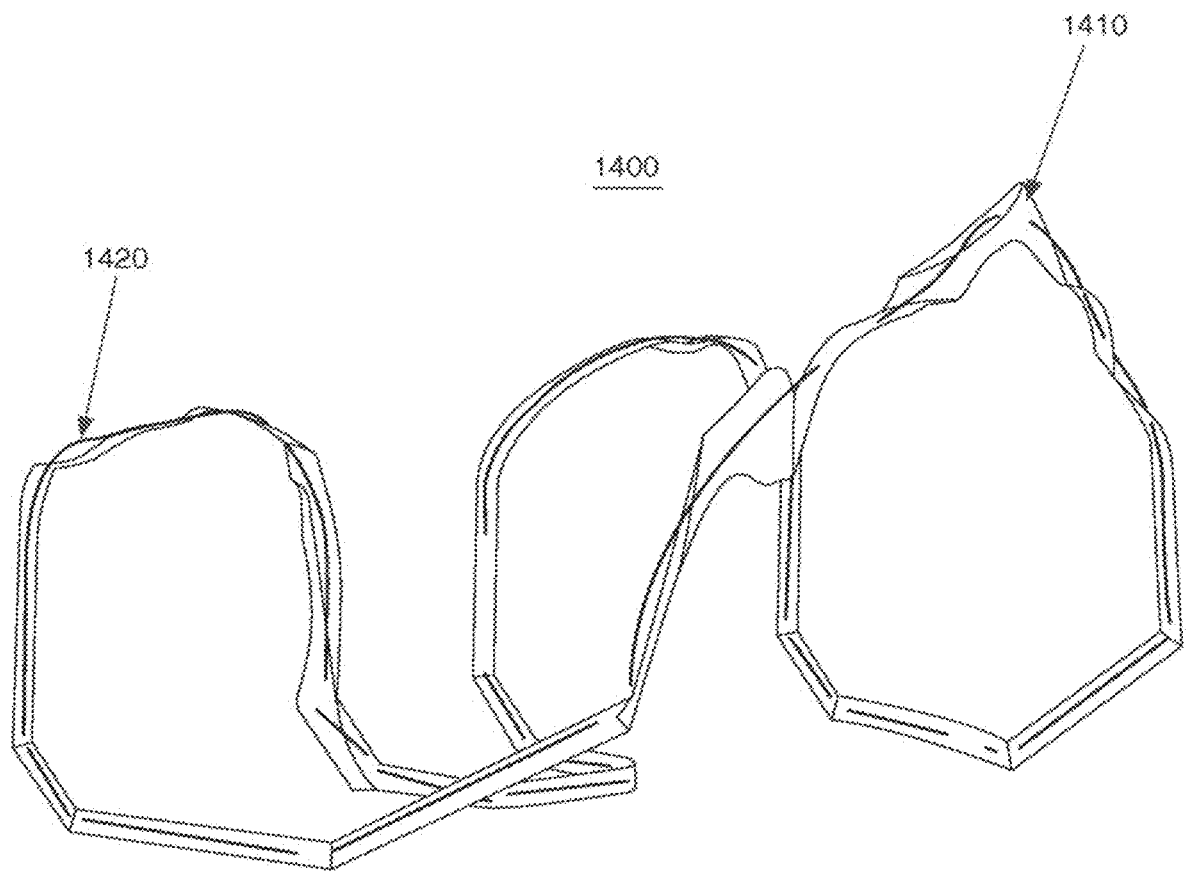

FIG. 14 illustrates an example interface 1400 that shows a bone surface ribbon 1410 with a curve 1420 overlaid on the bone surface ribbon 1410. The curve 1420 represents a three-dimensional fit to the bone surface ribbon 1410 and includes portions that extend outside and inside of the bone surface ribbon 1410 within a tolerance zone. The curve 1420 is a BSpline overlaid on the bone surface ribbon 1410.

In some implementations, the system 200 determines the outline representation for only a portion of the outer surface of the periphery of the resultant bone volume. In these implementations, the system 200 may create a partial bone surface ribbon for the portion of the outer surface of the periphery of the resultant bone volume and may fit a curve to the partial bone surface ribbon. The system 200 also may create a complete bone surface ribbon for the entire outer surface of the periphery of the resultant bone volume and fit a curve to only a portion of the complete bone surface ribbon. The system 200 further may create a complete bone surface ribbon for the entire outer surface of the periphery of the resultant bone volume, fit a curve to an entirety of the complete bone surface ribbon, and then select a portion of the curve that corresponds to the portion of the outer surface of the periphery of the resultant bone volume.

The system 200 may select the portion of the outer surface of the periphery of the resultant bone volume based on user input that defines a portion of the resultant bone volume of interest to a user. For example, the system 200 may receive user input that defines a part of the outer surface of the periphery of the resultant bone volume of interest. In this example, the part may correspond to a part of the outer surface of the periphery where variation occurs and the benefits of fitting an implant at the part of the outer surface of the periphery outweigh the risks of doing so, such as risking overhang by attempting a close fit or disrupting an articulating surface of the implant. In this regard, the system 200 may select non-articulating surfaces or edges of the resultant bone volume and/or portions of the resultant bone volume where a risk of tissue damage due to overhang is lower.

In implementations in which the techniques described throughout this disclosure are used in knee implants (e.g., TKA), the system 200 may select a portion of the outer surface of the periphery of a femur that corresponds to the anterior flange. The portion of the outer surface of the periphery of the femur that corresponds to the anterior flange may be of interest because significant variation of the anterior flange exists among different patients and the downside of fitting an implant to the anterior flange is limited since the portion of the implant fitted to the anterior flange is not an articulating surface.

Figure 15:
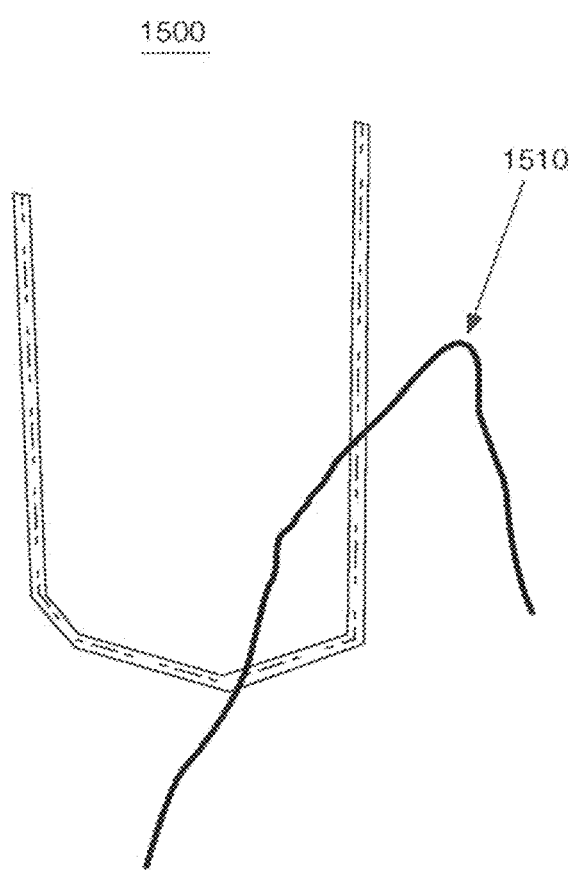

FIG. 15 illustrates an example interface 1500 that shows a portion of a curve 1510 created to model a portion of a bone surface ribbon. The curve 1510 represents a three-dimensional fit to a portion of a bone surface ribbon located at an anterior flange of a femur bone. The curve 1510 is a BSpline overlaid on a portion of a bone surface ribbon located at an anterior flange of a femur bone.

Referring again to FIG. 3, the system 200 uses the outline representation in one or more operations related to implant matching (370). For instance, the system 200 may design a custom implant based on the outline representation, use the outline representation in generating a library of implants, and/or use the outline representation to select, from a library of implants, an implant to use in an implant procedure. In designing a custom implant, the system 200 may input the outline representation to an implant manufacturing application and the implant manufacturing application may generate a design of an implant that corresponds to the outline representation. In this regard, the system 200 may input a spline that defines the outline representation and the implant manufacturing application may generate additional splines used to develop the custom implant.

In some examples, the outline representation may represent an entire outer surface of a periphery of a resultant bone volume. In these examples, the system 200 generates a design of a custom implant in which an entire periphery of the custom implant corresponds to the outline representation. In other examples, the outline representation may represent a portion of an outer surface of a periphery of a resultant bone volume. In these examples, the system 200 generates a design of a custom implant in which a portion of the periphery of the custom implant corresponds to the outline representation and the remaining portion of the periphery of the custom implant corresponds to a standard implant design.

In some implementations, the system 200 offsets the outline representation in designing an implant. In these implementations, the system 200 may slightly reduce how far the outer surface of the outline representation extends (e.g., slightly shrinks the outline representation) and may use the reduced version of the outline representation as a basis for designing the implant. The system 200 may define the amount of reduction in accordance with implant manufacturing tolerances to reduce the risk of manufacturing variations causing the implant to overhang at one or more portions of the bone. For example, the system 200 may offset a bone surface ribbon (or a curve fitted to a bone surface ribbon) by two millimeters prior to using the bone surface ribbon (or the curve fitted to the bone surface ribbon) to generate an implant design. Offsetting the bone surface ribbon may be necessary to account for differences between the source data and the actual size of patient bones versus the CAD models. In offsetting the bone surface ribbon, the system 200 may offset the implant model perimeter approximately 3.5 mm inside the bone model perimeter.

Figure 16:
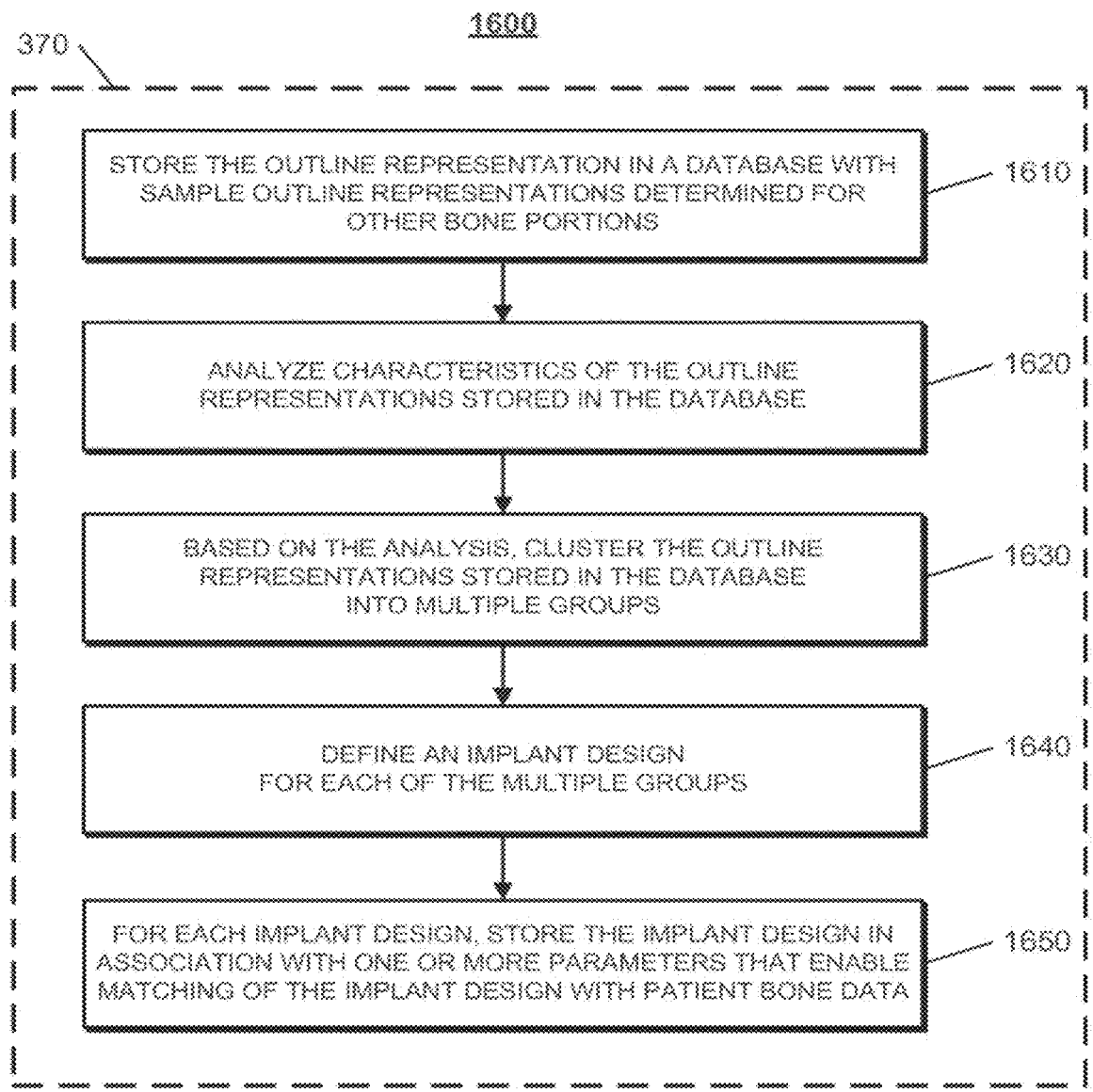

FIG. 16 illustrates a process 1600 for generating a library of implant designs. The process 1600 may be used in using the outline representation in one or more operations related to implant matching referenced above with respect to reference numeral 370. The operations of the process 1600 are described generally as being performed by the system 200. In some implementations, operations of the process 1600 may be performed by one or more processors included in one or more electronic devices.

The system 200 stores the outline representation in a database with sample outline representations determined for other bone portions that correspond to the portion of the bone (1610). For instance, the system 200 maintains a database of sample outline representations for a particular bone, or subgroup or cluster of bones (e.g., a femur or a distal end of a femur) and adds the determined outline representation to the database. The sample outline representations may include outline representations determined for many different patients, including outline representations determined for bones of cadavers analyzed during a cadaver study. The sample outline representations may be complete outline representations for the particular bone or partial outline representations for the particular bone (e.g., an anterior flange profile of a distal end of femur). The system 200 also may store, in the database, other patient information related to the patient (e.g., age, gender, ethnicity, weight, height, etc.) and/or information related to the particular bone (e.g., size measurements of the particular bone). The system 200 may use the other patient information to assist in grouping the sample outline representations and matching a new patient to a grouping of the sample outline representations.

The system 200 analyzes characteristics of the outline representations stored in the database (1620). For example, the system 200 determines size and/or shape characteristics of the sample outline representations stored in the database and compares the determined size and/or shape characteristics of the sample outline representations to one another. In this example, the system 200 determines a level of similarity between sample outline representations based on the comparison.

In some implementations, the system 200 uses size and/or shape characteristics of entire sample outline representations in performing the analysis. In other implementations, the system 200 uses size and/or shape characteristics of portions of sample outline representations in performing the analysis. For instance, the system 200 may select a subset of positions along the sample outline representations and use size and/or shape characteristics of each of the subset of positions in the analysis. In implementations in which the techniques described throughout this disclosure are used in knee implants (e.g., TKA), the system 200 may select several points along a representation of an anterior flange, determine location information of each of the several points, and use the location information in the analysis.

Based on the analysis, the system 200 clusters the outline representations stored in the database into multiple groups that each includes outline representations having similar characteristics (1630). For instance, the system 200 uses a clustering process to group the sample outline representations into multiple, different groups of sample outline representations that have similar size and/or shape characteristics. The system 200 may perform the clustering based on the comparison of size and/or shape characteristics of the sample outline representations. The system 200 may perform clustering by assigning a set of sample outline representations into groups (called clusters), so that the sample outline representations in the same cluster are more similar (in some sense or another) to each other than to those in other clusters.

Any type of one or more clustering processes may be used to arrange the sample outline representations into groups having similar size and/or shape characteristics. For instance, the system 200 may use a machine learning process to group sample outline representations with similar characteristics together. Example clustering processes the system 200 may use include one or more of connectivity-based clustering processes (e.g., hierarchical clustering processes), such as single-linkage clustering, complete linkage clustering, and average linkage clustering, centroid-based clustering processes, such as k-means clustering, k-medians clustering, and Fuzzy c-means clustering, distribution-based clustering processes, such as expectation-maximization (EM) clustering and mixture of Gaussians clustering, and density-based clustering processes, such as density-based spatial clustering of applications with noise (DBSCAN) and ordering points to identify the clustering structure (OPTICS).

The system 200 defines an implant design for each of the multiple groups (1640). For example, after the sample outline representations have been clustered into multiple groups with similar characteristics, the system 200 determines an implant design for a particular group using the sample outline representations included in the particular group. In this example, the system 200 may analyze characteristics of the sample outline representations included in the particular group and determine a best fit outline representation for the sample outline representations included in the particular group. The system 200 then may use the best fit outline representation to define an implant design for the particular group using the techniques described above with respect to defining a custom implant using an outline representation. After defining the implant design for the particular group, the system 200 continues processing other groups of outline representations until an implant design has been defined for each of the groups.

In some implementations, to define an implant design for a group of outline representations, the system 200 may compute an average outline representation by averaging the outline representations included in the group. In these implementations, the system 200 may use the average outline representation to define an implant design for the particular group using the techniques described above with respect to defining a custom implant using an outline representation.

In addition, to define an implant design for a group of outline representations, the system 200 may use minimum and maximum criteria of the outline representations included in the group. For instance, the system 200 may define a combined outline representation based on minimum and maximum points of each of the outline representations included in the group such that all of the outline representations included in the group fit within the combined outline representation.

In some examples, the rules applied to generate a particular implant design include user needs constraints specifying where around the implant boundary or perimeter that implant overhang beyond bone cut perimeters and bone underhang beyond the implant boundary or perimeter by boundary zone are specified. These boundary constraints address risks including soft tissue risk, load transmission from implant to cortical (more dense outer bone), minimizing blood loss, and other known risks. Design team surgeons may evaluate and validate the designs and the system 200 may adapt the designs based on user input specifying recommendations of the design team surgeons.

After defining an implant design for each of the multiple groups, the system 200 may evaluate the defined implant designs for each group. For example, after the system 200 has defined an implant design for a particular group, the system 200 may compare the implant design to each of the outline representations included in the particular group and, based on the comparison, determine how closely the implant design matches each of the outline representations included in the particular group. Based on the determinations of how closely the implant design matches each of the outline representations included in the particular group, the system 200 may determine whether the implant design matches each of the outline representations included in the particular group within a threshold degree, Based on a determination that the implant design matches each of the outline representations included in the particular group within the threshold degree, the system 200 determines that the implant design is sufficient for the particular group and assigns the implant design to the particular group.

However, based on a determination that the implant design does not match one or more of the outline representations included in the particular group within the threshold degree, the system 200 may reject the implant design and provide an alert indicating the implant design is insufficient for the particular group. After rejecting the implant design, the system 200 may attempt to use another technique to generate a new implant design based on the outline representations included in the particular group. The system 200 may evaluate the new implant design to determine whether the new design matches each of the outline representations included in the particular group within the threshold degree. The system 200 may continue to attempt new implant designs for the particular group until the system 200 determines that an implant design matches each of the outline representations included in the particular group within the threshold degree or that all techniques for generating an implant design based on the outline representations included in the particular group have been attempted without success.

In some examples, after rejecting the implant design or after determining that all techniques for generating an implant design based on the outline representations included in the particular group have been attempted without success, the system 200 determines to perform additional clustering on the outline representations included in the particular group to divide the particular group into smaller groups of outline representations. In these examples, the system 200 repeats the clustering operations described above with parameters that result in a closer degree of similarity between the outline representations in the groups. After reclustering, the system 200 repeats the operations described above with respect to generating an implant design for each group and evaluating implant designs until an acceptable implant design has been defined for each group.

In some implementations, after rejecting the implant design or after determining that all techniques for generating an implant design based on the outline representations included in the particular group have been attempted without success, the system 200 may remove problematic outline representations from the particular group such that the implant design matches each of the remaining outline representations included in the particular group within the threshold degree. In these implementations, the system 200 may attempt to cluster removed outline representations into other groups (e.g., new groups) or may determine to leave the removed outline representations without a corresponding implant design in the library. For example, the system 200 may determine to stop clustering and defining new implant designs when the library of available implant designs covers a threshold percentage (e.g., eighty percent) of sample outline representations within a threshold degree. In this example, the system 200 may determine that a custom implant is needed for patients having similar outline representations to the removed outline representations that do not have a corresponding implant design in the library.

In some examples, the system 200 may receive new sample outline representations from new patients and/or may receive feedback on fits of implants selected from the library of implants. In these examples, the system 200 may use the new sample outline representations from new patients and/or the feedback on fits of implants selected from the library of implants to update the clustering of sample outline representations in the database and define (or redefine) implant designs to expand the coverage of the library of implant designs.

The system 200, for each implant design, stores the implant design in association with one or more parameters that enable matching of the implant design with patient bone data (1650). For instance, the system 200 may store, in association with data identifying the implant design, a best fit outline representation or an average outline representation for the outline representations included in the group corresponding to the implant design. The system 200 also may store, in association with data identifying the implant design, a range of outline representation data that covers outline representations that fit within the group corresponding to the implant design. The system 200 further may store, in association with data identifying the implant design, bone size measurements and other patient data (e.g., age, gender, ethnicity, weight, height, etc.) that may be useful in determining whether or not a patient matches the implant design. The system 200 may store any type of data that enables matching of patient bone data to an implant in the library of implants.

Although the process 1600 described above with respect to FIG. 16 addresses clustering using outline representations, similar techniques may be used with other types of data that is descriptive of bone shape and size. For example, the system 200 may perform clustering using landmark sets. In this example, the system 200 uses landmarks in lieu of outline representations (e.g., BSplines) at the first stage where characterizing the bone cut shapes before the system 200 cluster cases of similar size and shape. After clustering based on landmarks, the system 200 creates corresponding "High Resolution" outline representations (e.g., BSplines), making one "High Resolution" outline representation (e.g., BSpline) that fits each bone in a cluster of cases. The system 200 then applies known tolerances (e.g., manufacturing tolerances, surgeon variability, inspection tolerances, imaging tolerances, etc.) to the "High Resolution" outline representation (e.g., BSpline), and creates a corresponding "Low Resolution" outline representation (e.g., BSpline) that accounts for the tolerances.

From the "Low-Resolution" outline representation (e.g., BSpline), the system 200 creates an implant design. For instance, the system 200 creates a new boundary or perimeter trim sheet that cuts away or adds to the existing femoral implant model to make a new patient or cluster specific femoral implant that satisfies the rules for the particular cluster. Each cluster then has: (1) a High Resolution outline representation (e.g., BSpline), (2) Low Resolution outline representation (e.g., BSpline), and (3) Femoral Implant Model. The outline representation (e.g., BSpline) may be defined using a UniGraphics (UG) Expression List that can be generated using programming code, such as a MatLab or Visual Basic program implemented on a computer system. The UG Expression List generation may be done using an automated process as described above.

In some examples of clustering the bones, the system 200 may cluster by bone (e.g., lining up similarly shaped bones) or the system 200 may cluster the features themselves relative to some global reference frame. For example, the system 200 may line up all of the bones according to existing surgical protocols and extract the radius of the posterior condyles from a set of multiple clusters (e.g., fifty clusters). The system 200 may use more resolution on the anterior flange since the anterior flange has a higher degree of variation in the population. Accordingly, the system 200 may use more clusters for the anterior flange feature (e.g., four hundred clusters of that feature). In feature-based clustering, the features used may correspond to a feature found in the CAD model to model the implant (or instrument) or a feature in the manufacturing process (e.g., second operation grinding operation).

Along those same lines, the system 200 may include a minimum included tool radius to prevent the solution spline from having wrinkles or divots that are not manufacturable. This may be one of the driving factors behind why the curve 1420 is depicted as not following the "ribbon" exactly.

Figure 17:
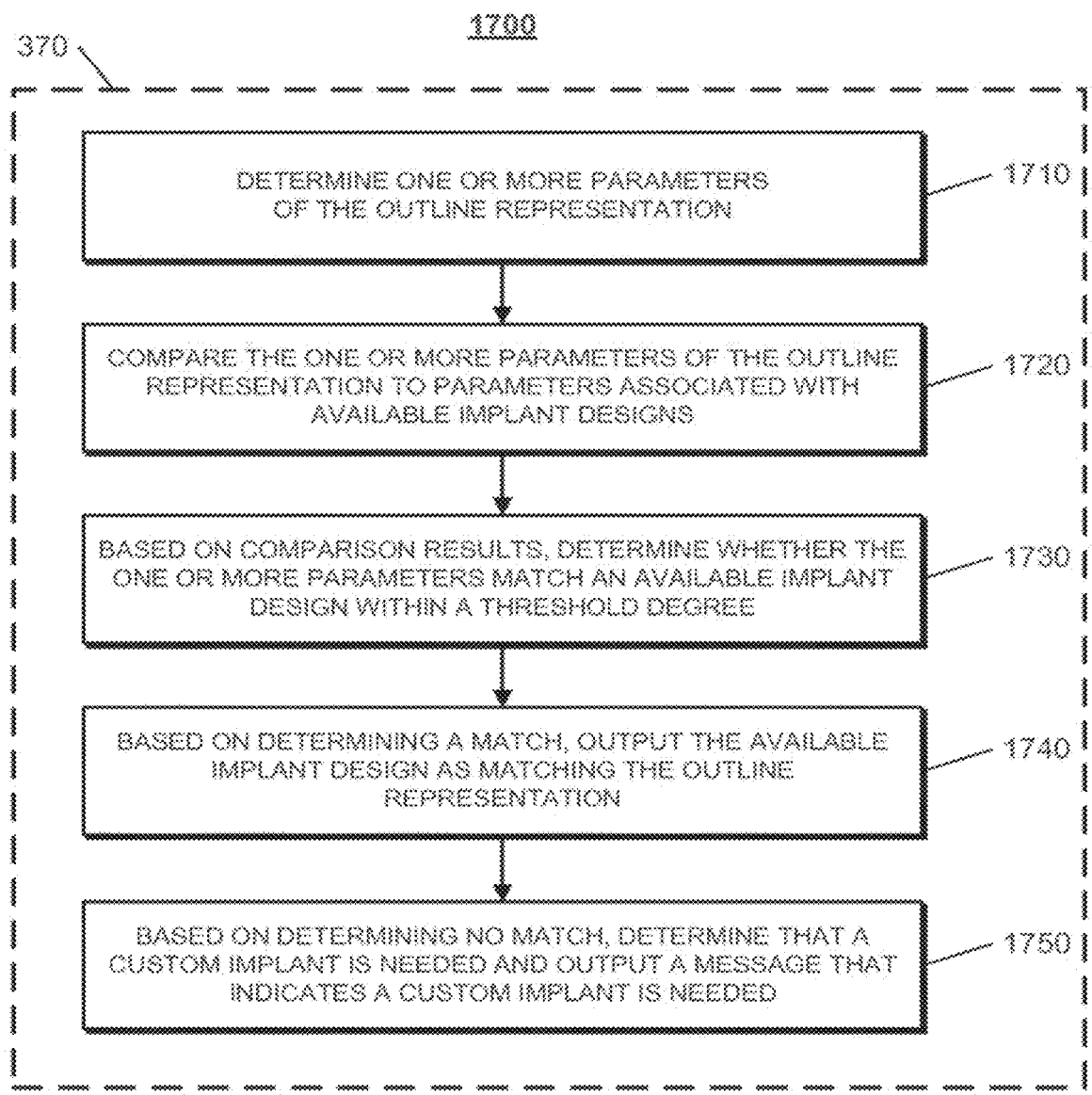

FIG. 17 illustrates a process 1700 for matching patient data to an implant. The process 1700 may be used in using the outline representation in one or more operations related to implant matching referenced above with respect to reference numeral 370. The operations of the process 1700 are described generally as being performed by the system 200. In some implementations, operations of the process 1700 may be performed by one or more processors included in one or more electronic devices.

The system 200 determines one or more parameters of the outline representation (1710). For instance, the system 200 may determine size and/or shape characteristics of the outline representation. The system 200 also may determine position data for portions of the outline representation that enables matching to implants in the library. The system 200 may determine any type of parameters that enable matching of the outline representation to an implant in the library of implants, including the parameters stored in association with implant designs in the process 1600. The system 200 may use the outline representation itself as the one or more parameters of the outline representation.

The system 200 compares the one or more parameters of the outline representation to parameters associated with available implant designs (1720) and, based on comparison results, determines whether the one or more parameters of the outline representation match an available implant design within a threshold degree (1730). For instance, the system 200 may access parameters stored in association with implant designs in the library of implant designs and compare the one or more parameters of the outline representation to the accessed parameters. Based on the comparison of the one or more parameters of the outline representation to the accessed parameters, the system 200 determines whether the one or more parameters of the outline representation match the accessed parameters within a threshold degree.

In some examples, the system 200 may compare a shape of the outline representation to shapes of outer perimeters of implant designs stored in the library of implant designs. In these examples, based on the comparison of the shape of the outline representation to shapes of outer perimeters of implant designs stored in the library of implant designs, the system 200 determines whether the shape of the outline representation exactly matches a shape of an outer perimeter of an implant design stored in the library or matches a shape of an outer perimeter of an implant design stored in the library within a threshold tolerance zone (e.g., matches the outer perimeter within two millimeters at all locations).

In some implementations, the system 200 may determine size measurements of the portion of the bone and first compare the determined size measurements to sizes of implant designs stored in the library. In these implementations, the system 200 may, based on the comparison, select a subset of implant designs within the library that are acceptable for the determined size measurements. Although each of the subset of implant designs is acceptable for the size of the portion of the bone, each of the subset of implant designs has a different shape for an outer perimeter of the implant design. Accordingly, after selecting the subset, the system 200 performs a second comparison to select the implant design that best matches a shape of the portion of the bone. In this regard, the system 200 compares the one or more parameters of the outline representation to parameters associated with each of the subset of implant designs to assess whether a shape of the outline representation matches a shape of any of the subset of implant designs.

Based on a determination that the one or more parameters of the outline representation match the available implant design within the threshold degree, the system 200 outputs the available implant design as matching the outline representation (1740). For instance, the system 200 may display the matching implant design to a surgeon (or other medical care provider) for use in an implant procedure. If the system 200 determines that multiple implant designs match the outline representation within the threshold degree, the system 200 may display each of the multiple implant designs to enable a surgeon to select the preferred implant design for the implant procedure.

Based on a determination that the one or more parameters of the outline representation do not match an available implant design within the threshold degree, the system 200 determines that a custom implant is needed and outputs a message that indicates a custom implant is needed (1750). For instance, the system 200 may display a message indicating that no match was found in the library of implants. The system 200 also may initiate a process to define a custom implant for the portion of the bone based on the determination that the one or more parameters of the outline representation do not match an available implant design within the threshold degree.

Figure 18:
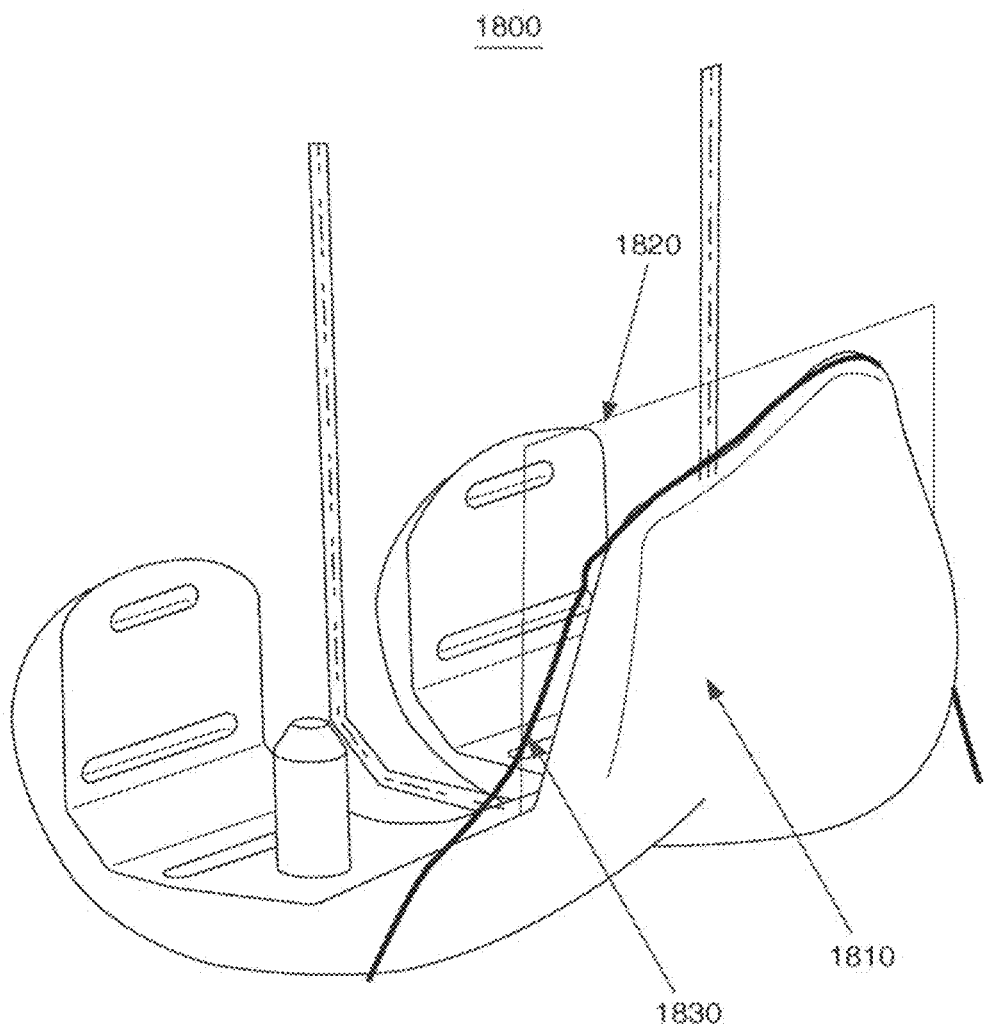

FIG. 18 illustrates an example interface 1800 that shows a three-dimensional implant design 1810, a plane 1820 that corresponds to a face of the implant design 1810, and a curve 1830 that has been projected onto the face of the implant design 1810. The curve 1830 is a three-dimensional outline representation of an anterior flange of a distal end of a femur. As shown, the curve 1830 does not match the outer periphery of the implant design 1810 at the plane 1820 that corresponds to the face of the implant design 1810. Accordingly, the system 200 updates the implant design 1810 to have a shape that matches the curve 1830. The system 200 may use the updated implant design to define a custom implant that has an outer periphery that matches the curve 1830.

Figure 19:
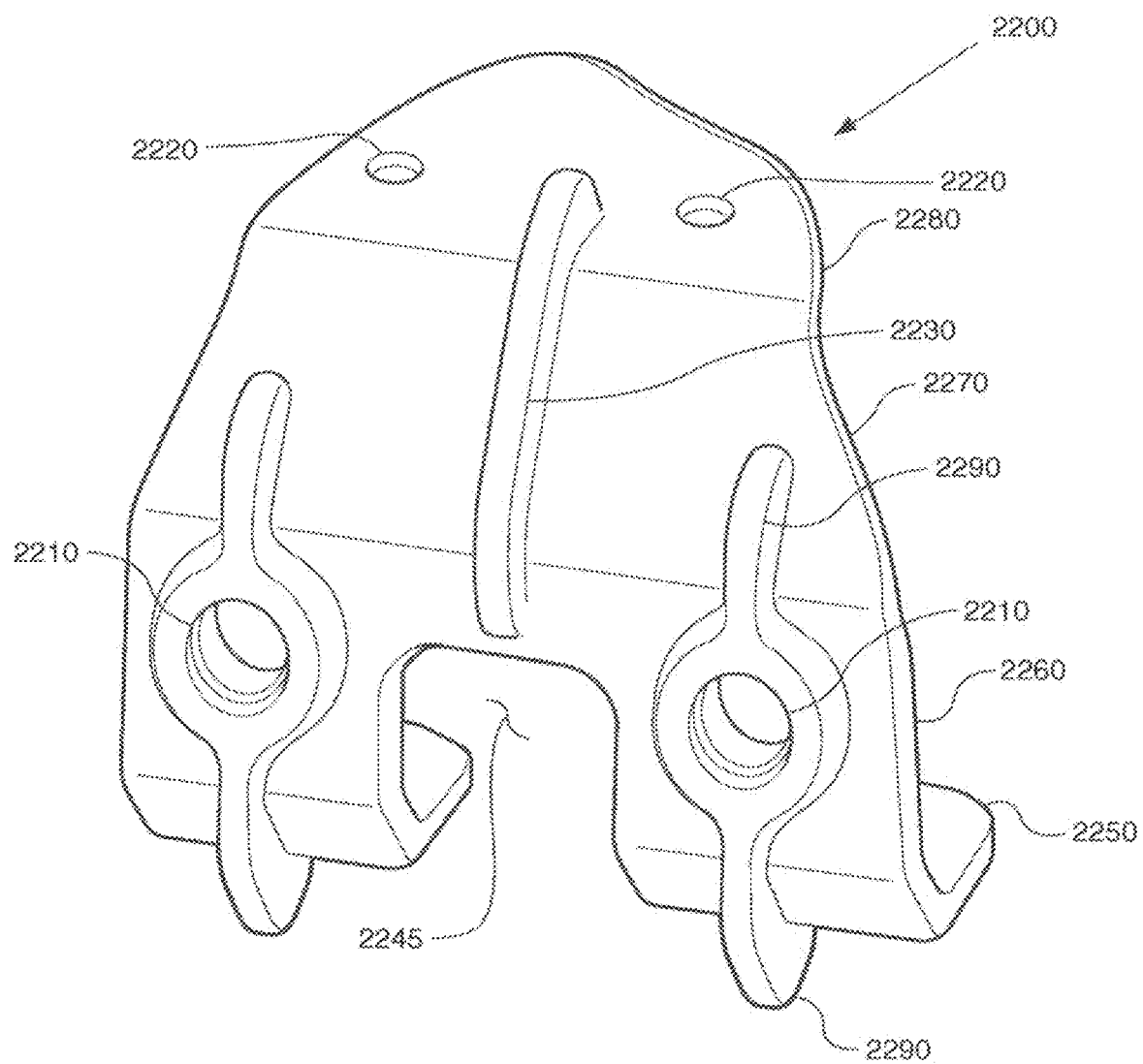
FIG. 19 illustrates a knee box cut shape and size of the prior art.

FIG. 19 illustrates a medial-lateral (ML) positioning template 2200. The ML positioning template 2200 is also known as an ML positioner. The ML positioning template 2200 is used to locate the custom implant or an implant design from a library of many discrete sizes on the distal end of a femur in a medial-lateral position. The perimeter shape of the ML positioner 2200 is determined using the same methodology as described above for the implant. The shape of the ML positioner perimeter can be defined using a BSpline or some other 3-dimensional curve definition convention. In one example, a BSpline defines one new 3D solution curve that can be extracted from the implant model template to create a new implant perimeter size and a new ML positioner. Both the implant and the ML positioner can be designed in a single CAD model or in separate CAD models with perimeter shape(s) defined by the same BSpline. In the preferred embodiment, the ML positioner perimeter shape matches that of the implant, but in some embodiments, the ML positioner could have an offset inward or outward relative to the implant perimeter. As examples, the offset may be 1-4 mm, more narrowly 1-2 mm, or about 2 mm. In some embodiments, the ML Positioner includes articular surfaces, thus combining the ML centering function and the ligament balancing into one instrument. In some embodiments, only a portion of the ML positioner matches the shape of the implant. For example, only the medial and lateral perimeter match in shape and as such each of the medial and lateral perimeters have a patient specific shape.

Figure 23:
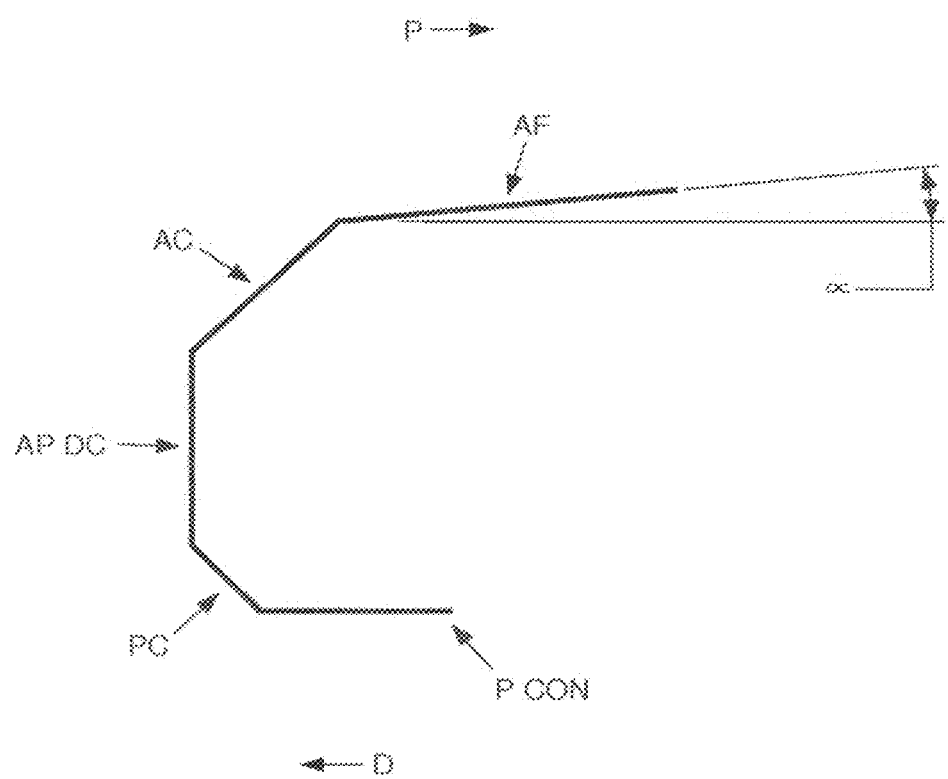
Figure 25:
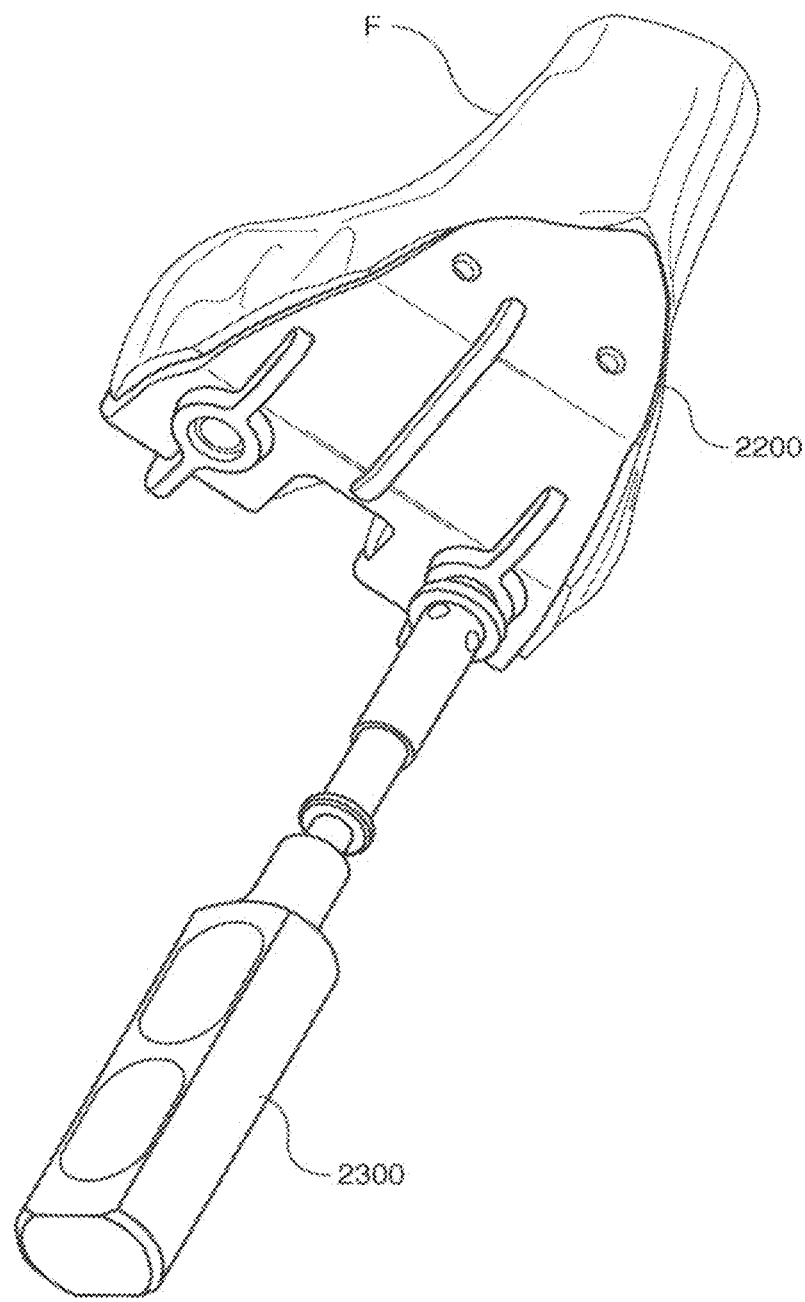

The bone facing side of the ML positioner has a standard box cut shape and size. A typical box cut shape and size is shown in FIG. 23. The typical box cut shape includes an anterior-posterior distal cut surface APDC, a posterior chamfer surface PC, an anterior chamfer surface AC, posterior condyle surfaces PCON, and an anterior flange surface AF. AF extends anteriorly relative to the coronal plane at an angle α. The proximal P and distal D directions are also illustrated. The dimensions of the box cut shape and size for the ML Positioner depends upon the particular knee system selected.

Figure 20:
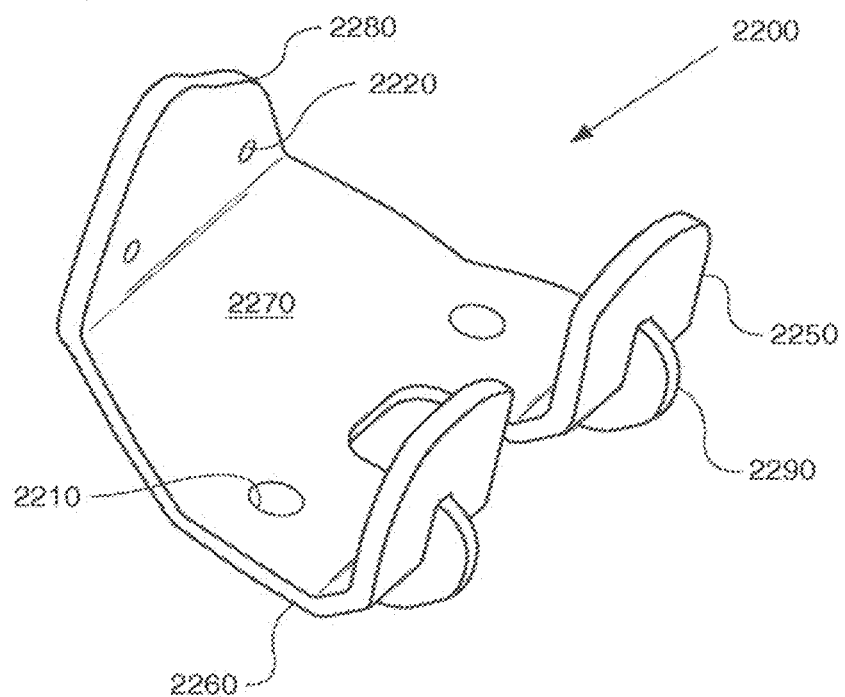
FIGS. 20-27 illustrate an implant positioning template.
Figure 21:
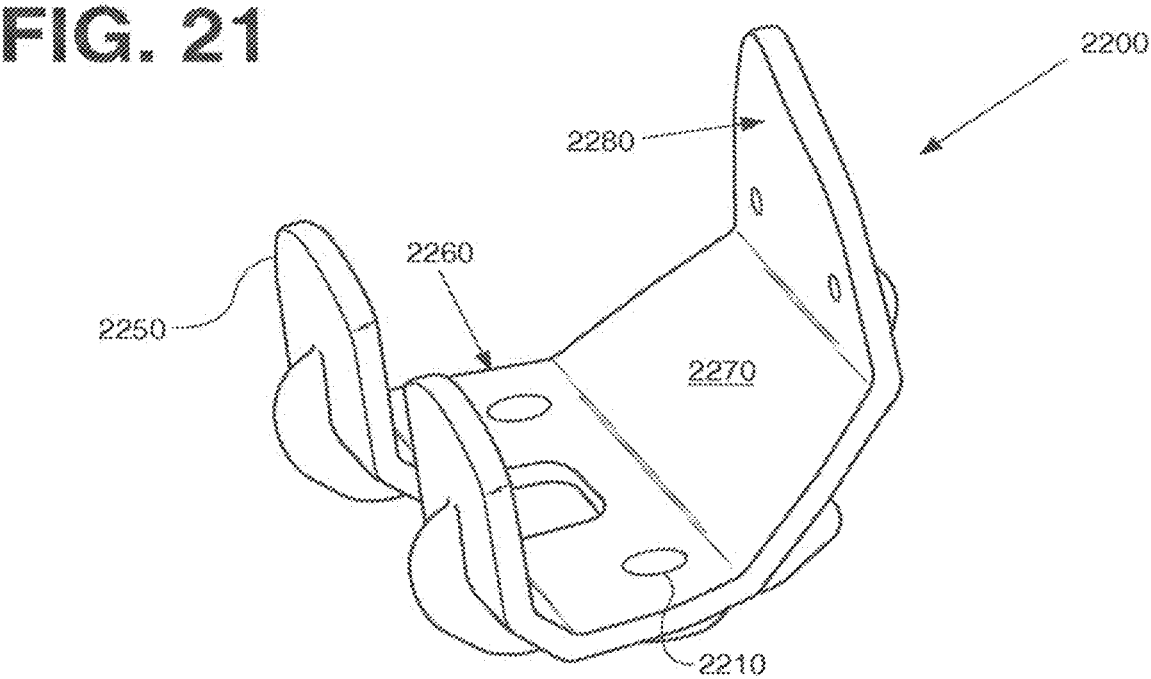
Figure 22:
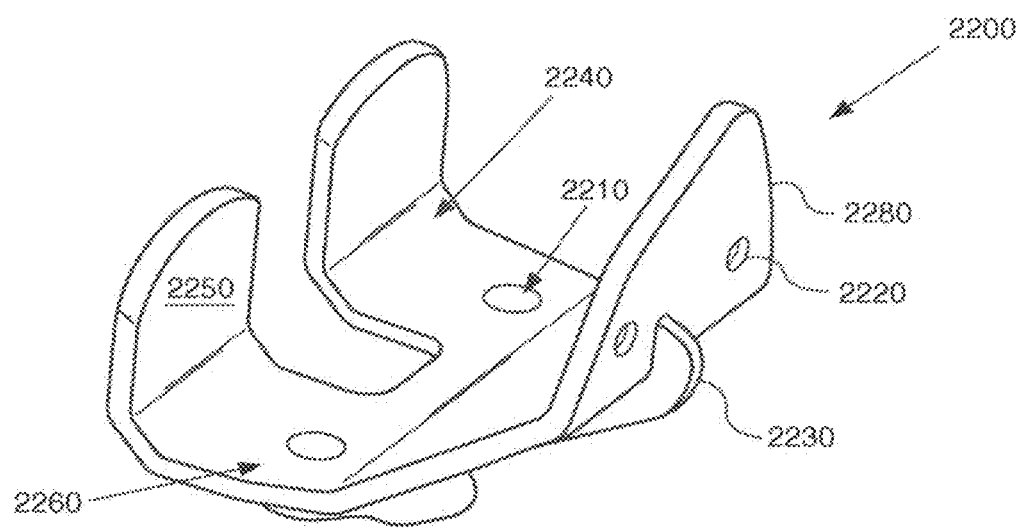
Figure 24:
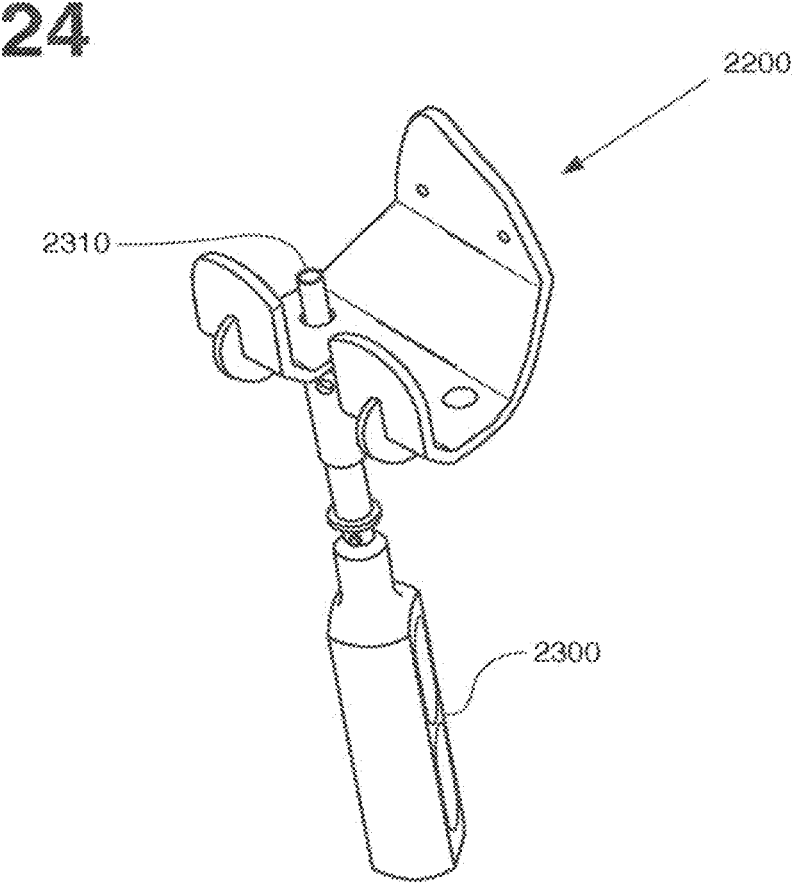
Figure 26:
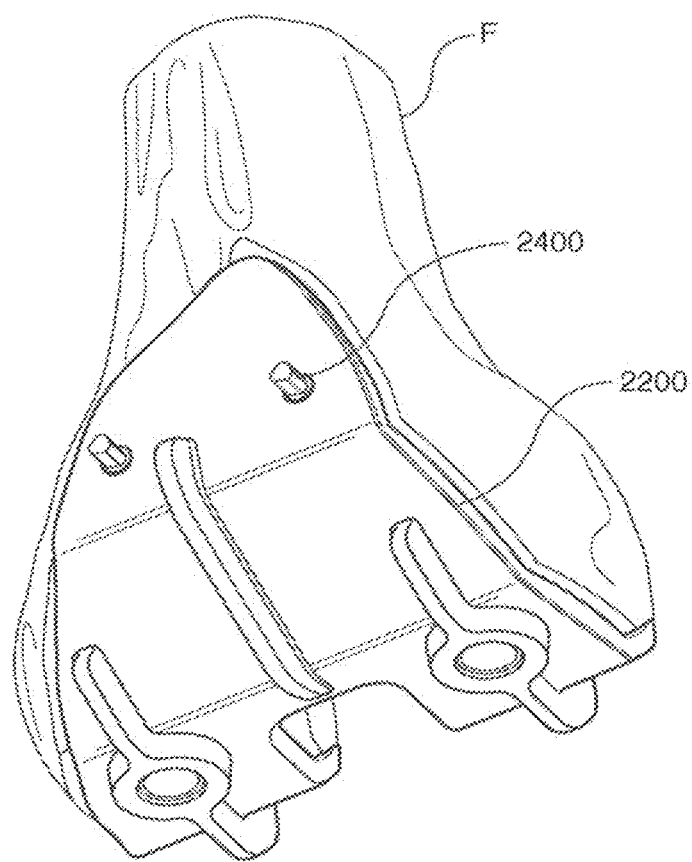
Figure 27:
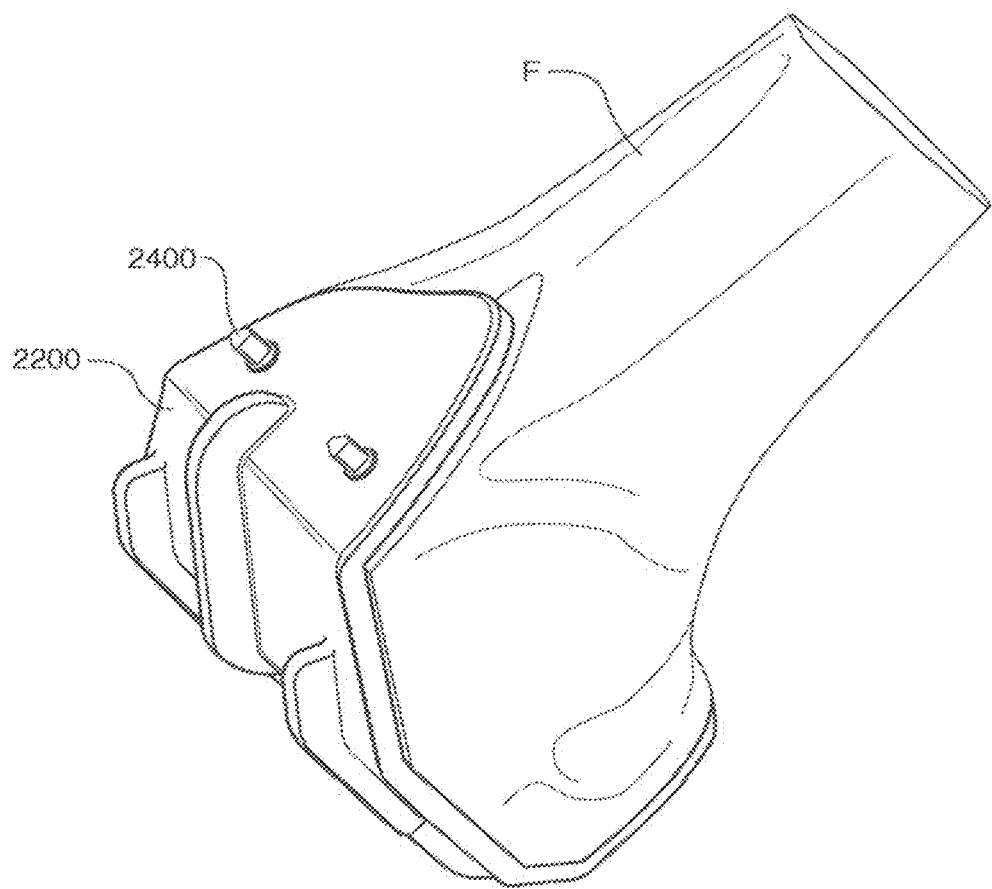

Referring once again to FIG. 19 and also to FIGS. 20-22, the ML positioner 2200 has locating openings 2210. The locating openings 2210 are used to create holes in the distal end of the femur such that the patient specific knee implant is centered on the distal femur. The locating openings 2210 may take the form of holes, slots, overlapping holes, or combination slots that allow for variance in the medial-lateral and anterior-posterior directions. In the depicted embodiment, the locating openings 2210 are shown as holes. In some embodiments, the ML positioner has pin holes 2220. Although pin holes 2220 are depicted as circular holes, they may have some other shape, such as a slot. In some embodiments, the ML positioner includes a rib stiffener 2230. The ML positioner includes at least one paddle 2250, posterior chamfer portion 2240, distal cut surface portion 2260, anterior chamfer portion 2270, and anterior flange portion 2280. In some embodiments, stiffeners 2290 extend around lug openings 2210 and extend across the anterior chamfer portion 2270, the distal cut surface portion 2260, the posterior chamfer portion 2240, and the at least one paddle 2250. In some embodiments, the ML positioner includes notch 2245, and in such embodiments, the posterior chamfer portion includes a posterior lateral chamfer and a posterior medial chamfer, and the at least one paddle includes a posterior medial condyle and a posterior lateral condyle Referring to FIGS. 24-27, the ML positioner is placed on the prepared distal femur, and the locating holes 2210 are used to create lug holes in the distal femur. In some embodiments, the ML positioner is placed such that the perimeter of the ML positioner matches the perimeter of the distal femur. In some embodiments, the ML positioner perimeter is offset inwardly relative to the perimeter of the distal femur. In other embodiments, only portions of the ML positioner perimeter match portions of the distal femur perimeter. In yet other embodiments, the distal cut portion of the ML positioner is centered relative to the overall width of the distal portion of the femur. A distal tip 2310 of a punch 2300 is inserted into the locating holes 2210 of the ML positioner 2200 to create holes in the distal femur that receive the implant. Alternatively, the holes in the distal femur may be drilled or reamed. In some embodiments, the ML positioner may be pinned in place using holes 2220 and pins 2400 (as best seen in FIGS. 26 and 27). As best seen in FIG. 27, the ML positioner also can serve as a first check of box cut shape and size for verifying the AP dimension and oblique length of chamfer cuts. By using the ML Positioner to locate the femoral implant lug holes, a centered fit of the implant is achieved.

Once the femoral implant lug holes are drilled, reamed, and/or punched through the use of the ML Positioner and into the distal face of the resected femur, the ML positioner is removed and the femoral articular trial is placed on the femur to evaluate ligament balance and range of motion. Following ligament balancing, the patient specific femoral implant is secured in placed on the distal femur using bone cement or an alternative fixation method.

Figure 28:
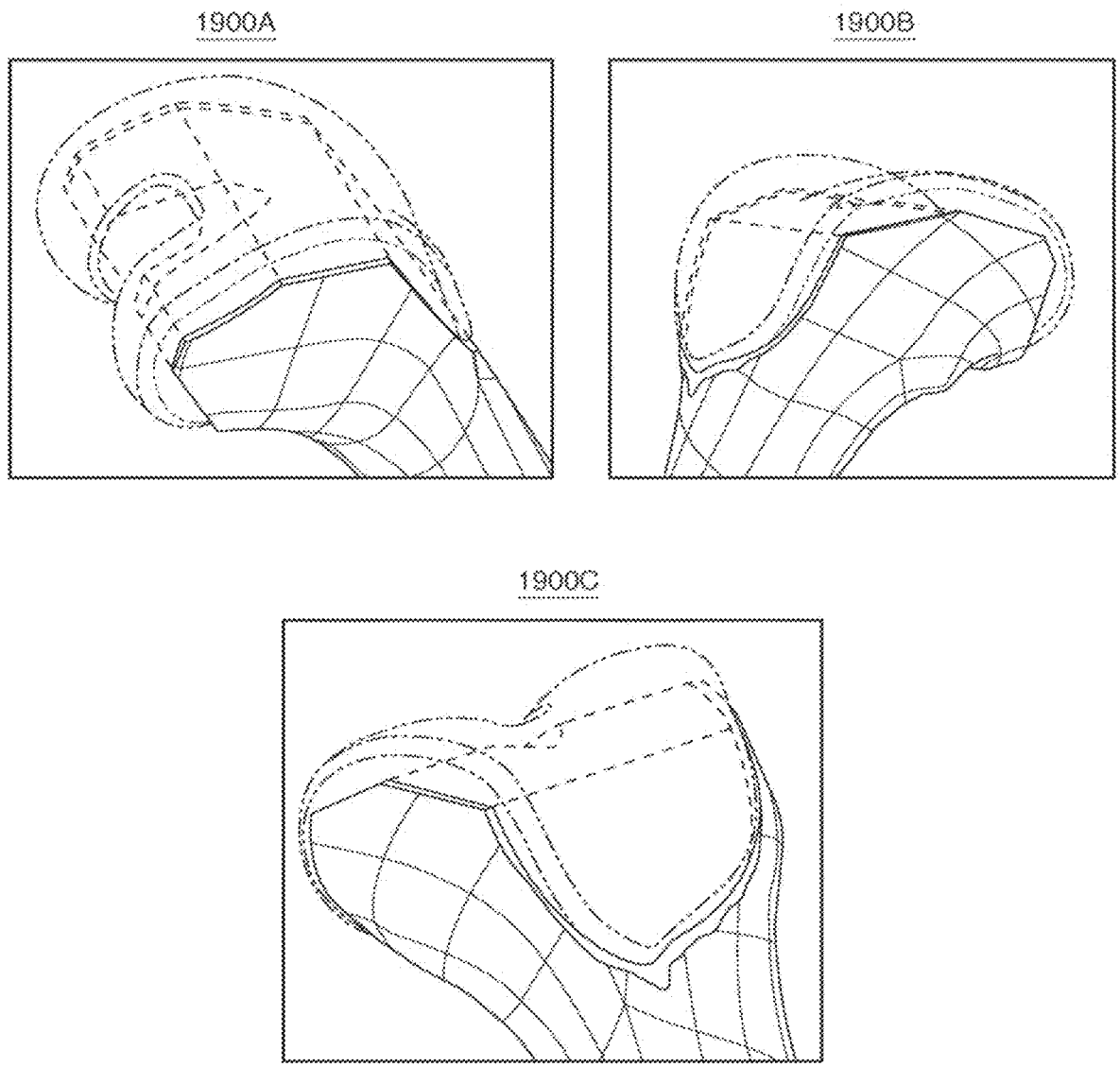
Figure 28:
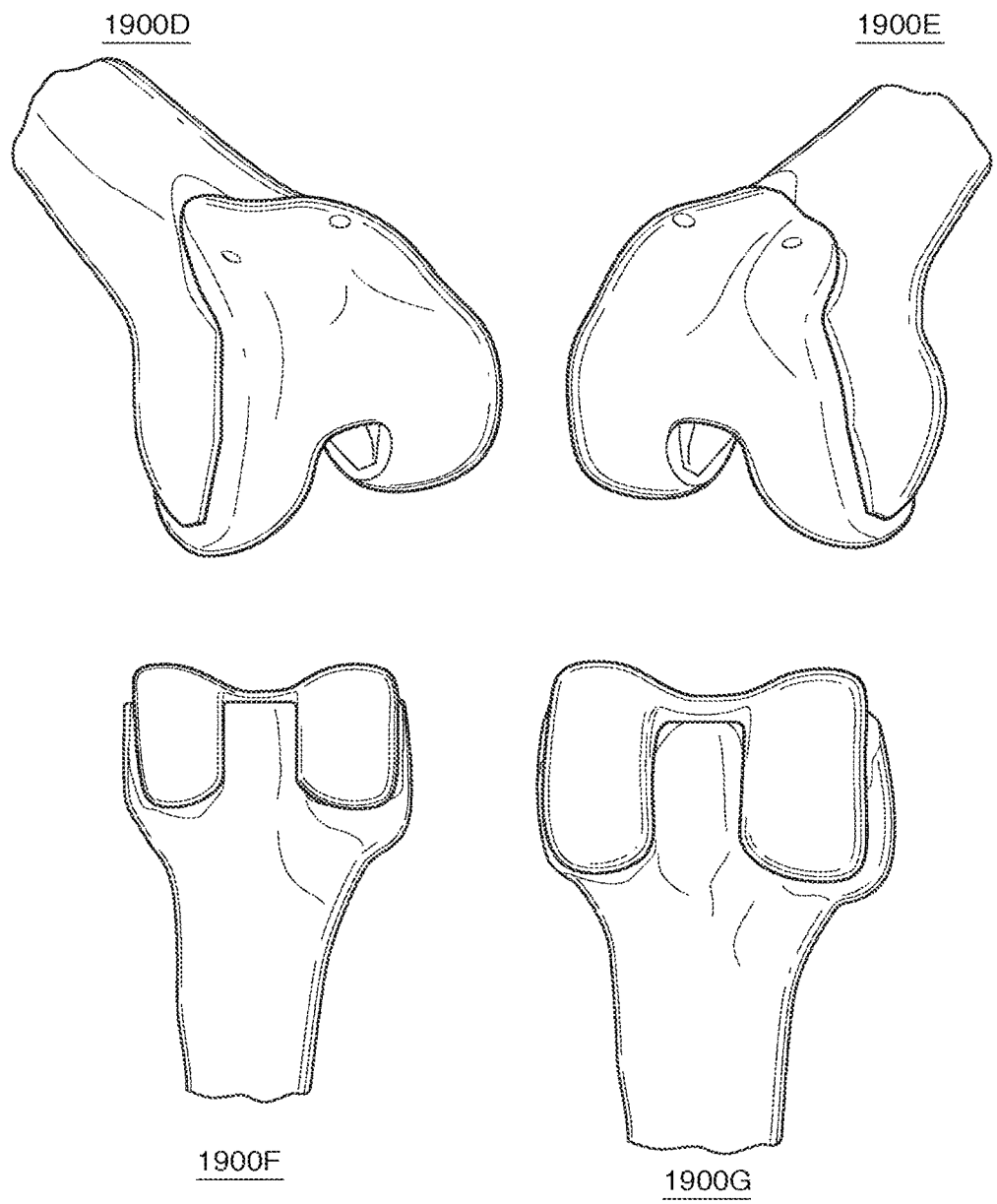

FIG. 28 illustrates an example interface 1900 that shows three views 1900A, 1900B, 1900C, 1900D, 1900E, 1900F and 1900G of a patient specific implant placed on a distal end of a femur. The patient specific implant may be a custom implant designed using the techniques described throughout this disclosure or an implant matched from a library of implants using the techniques described above with respect to FIG. 17. The patient specific implant is a femoral component placed on the distal end of a femur in TKA. As shown, the patient specific implant closely matches the bone resection around the perimeter of the implant/bone interface.

Although the examples described throughout this disclosure largely apply to knee implants and TKA, the techniques described throughout this disclosure may be applied to other implant procedures and joints, such as hips, ankles, shoulders, and spine. Although the example cuts have been portrayed as sawblade cuts, the cuts may be accomplished by a shaver, reamer, or burr and similar techniques may be used. The solution zone also may be flat as depicted in the examples or some other shape. For example, the zone might be in the shape of a hollow sphere for the head of the hip joint.

Further, in some implementations, a technique is described for creating patient specific implant shapes that closely match the boundaries of bone resections. The technique creates the boundaries by assembling discrete curves, splines, or segments of the bone resection boundaries into a complete bone resection boundary corresponding to the patient specific implant perimeter shape and size. Assembling the discrete curves, splines, or segments of the bone resection boundaries into the complete bone resection boundary may reduce or eliminate implant overhang beyond the bone resection boundaries and/or underhang of bone beyond the boundaries of the patient specific implant shape and size with a specified minimum underhang to allow for bone cut variations.

In some examples, the modular approach of assembling discrete segments of the bone resection boundaries into a complete implant perimeter shape and size allows for a broader set of discrete implant sizes that will fit a broader population of patients. By reducing the individual boundary segments into localized groupings of spline segments, the quantity of computer numerical control (CNC) programs required to manufacture implants also may be reduced, making the storage of spline segment libraries more manageable while offering more discrete sizes to the surgeon and patient.

In addition, the modular patient specific implant sizing methodology and technique may include clustering of data and assembling selected cluster modules or "buckets" into a complete implant boundary curve or Expression List. Any clustering or assembling technology may be used. And, the technique may be a structured technique for organization of bone cut data and the structured output of 3D CAD model Expression Lists that define the implant perimeter/boundary shapes and sizes specific to patient specific implant designs.

Figure 29:
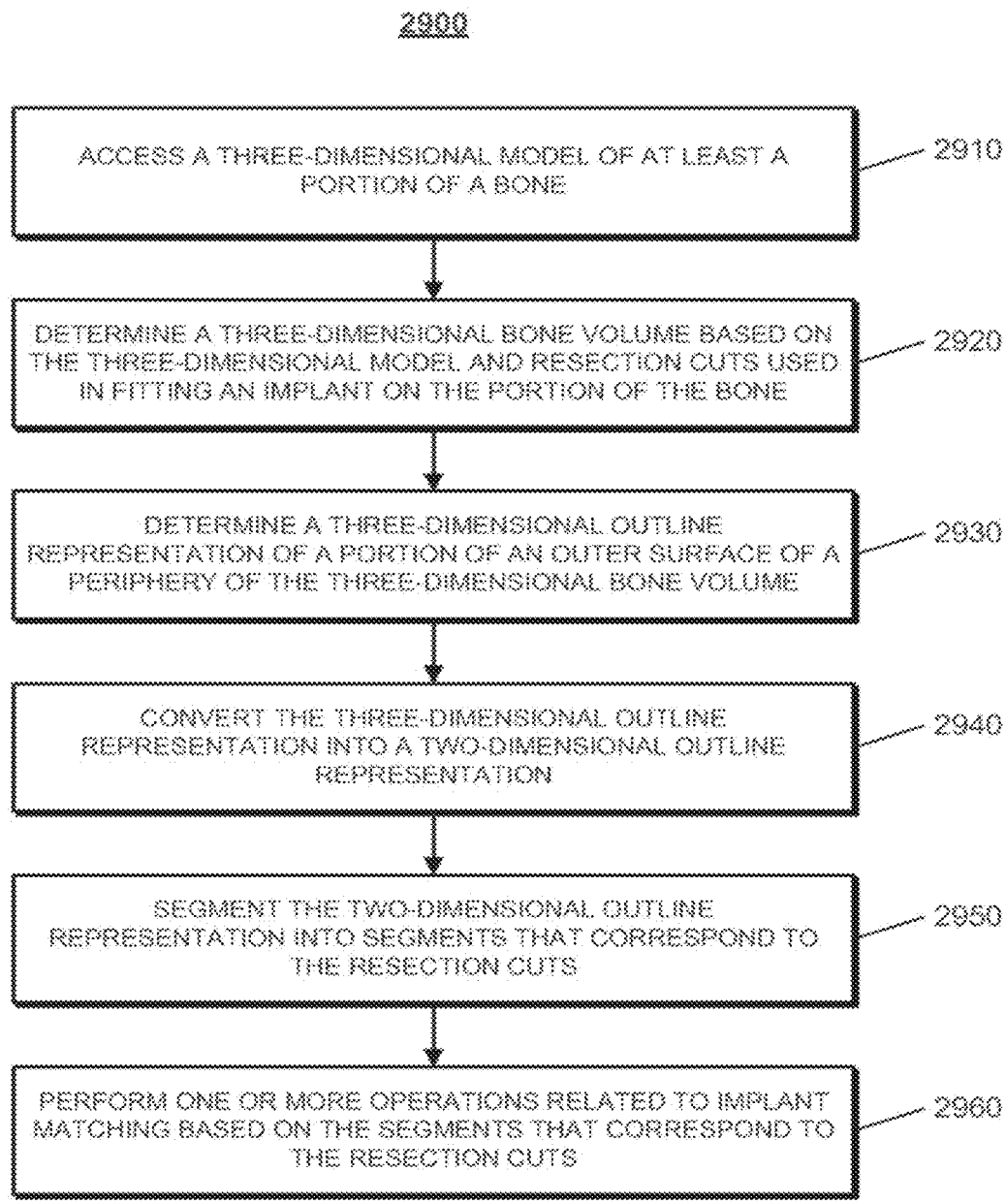

FIG. 29 illustrates a process 2900 used in implant matching. The operations of the process 2900 are described generally as being performed by the system 200. In some implementations, operations of the process 2900 may be performed by one or more processors included in one or more electronic devices.

The system 200 accesses a three-dimensional model of at least a portion of a bone (2910). For example, the system 200 may access a three-dimensional model of an entire bone or a portion of a bone that was generated based on medical measuring of a bone of a patient. In this example, the system 200 may receive the three-dimensional model from another system that generates the three-dimensional model by processing medical measurements taken of the bone or the portion of the bone. The medical measurements may be determined based on medical imaging of the bone or other physical measuring of the bone using medical instrumentation.

In some examples, the system 200 generates the three-dimensional model of an entire bone or a portion of a bone based on medical measuring of the bone of the patient. In these examples, the system 200 may access one or more images of the portion of the bone and generate the three-dimensional model of the portion of the bone based on the one or more images of the portion of the bone. The one or more images of the portion of the bone may be captured using MRI, CT, X-ray, Ultra-sound, or other medical imaging technology. The system 200 may access the one or more images of the portion of the bone from another system or may capture the one or more images of the portion of the bone through control of an imaging device.

In some implementations, the system 200 may access MRI images that depict multiple slices of the portion of the bone. In these implementations, the system 200 may digitally create a mask of the MRI slices and stitch the MRI slices together to create a solid model. Further, in these implementations, the system 200 may remove errors and smooth the data representing the solid model of the portion of the bone. In smoothing the data, the system 200 may select a minimum tool radius to eliminate all smaller internal radii along the surface, including divots and wrinkles. The system 200 may use the smoothed version of the solid model of the portion of the bone as the three-dimensional model of the portion of the bone.

In implementations in which the techniques described throughout this disclosure are used in knee implants (e.g., TKA), the system 200 accesses a three-dimensional model of at least a portion of a femur and/or a tibia. For instance, the system 200 may access a three-dimensional model of an entire femur or tibia, or may access a three-dimensional model of a portion of the femur or tibia located at the knee joint (e.g., the portion of the femur or tibia that receives an implant during TKA). In addition, the techniques described throughout this disclosure may be applied to other types of implant procedures (e.g., hip replacement, shoulder replacement, etc.). For other types of implant procedures, the system 200 may access a three-dimensional model of a portion of the bone that receives the implant, such as a portion of the bone located at a joint associated with the implant procedure.

The system 200 determines a three-dimensional bone volume based on the three-dimensional model of the portion of the bone and resection cuts used in fitting an implant on the portion of the bone (2920). For example, the system 200 analyzes the three-dimensional model of the portion of the bone and identifies locations on the three-dimensional model where resection cuts would be made in fitting an implant on the portion of the bone. In this example, the system 200 determines the three-dimensional bone volume as the portion of the three-dimensional model that corresponds to the locations of the resection cuts. The system 200 may account for tolerances and variations involved in fitting an implant on the portion of the bone in determining the three-dimensional bone volume. For instance, the system 200 may account for the tolerances and variations by defining a range of locations for the resection cuts that fit within the tolerances and variations. Then, the system 200 may determine the three-dimensional bone volume as the portion of the three-dimensional model that corresponds to the ranges of locations for the resection cuts. In some implementations, techniques similar to those described above with respect to reference numerals 320 to 350 in FIG. 3 and FIGS. 4-12 may be used in determining the three-dimensional bone volume based on the three-dimensional model of the portion of the bone and resection cuts used in fitting an implant on the portion of the bone.

The system 200 determines a three-dimensional outline representation of at least a portion of an outer surface of a periphery of the three-dimensional bone volume (2930). For example, the system 200 may analyze the three-dimensional bone volume and identify an outer surface of a periphery of the three-dimensional bone volume. In this example, the system 200 may extract, from the three-dimensional bone volume, the outer surface of the periphery of the three-dimensional bone volume to create a bone surface ribbon that models the outer surface of the periphery of the three-dimensional bone volume. The bone surface ribbon may be represented in three dimensions and may represent an outer surface of an implant that best matches the portion of the bone being evaluated while accounting for the tolerances and rules described throughout this disclosure. The bone surface ribbon may be used as the outline representation. In some implementations, techniques similar to those described above with respect to reference numeral 360 in FIG. 3 and FIGS. 13-15 may be used in determining the three-dimensional outline representation of the portion of the outer surface of the periphery of the three-dimensional bone volume.

Figure 30:
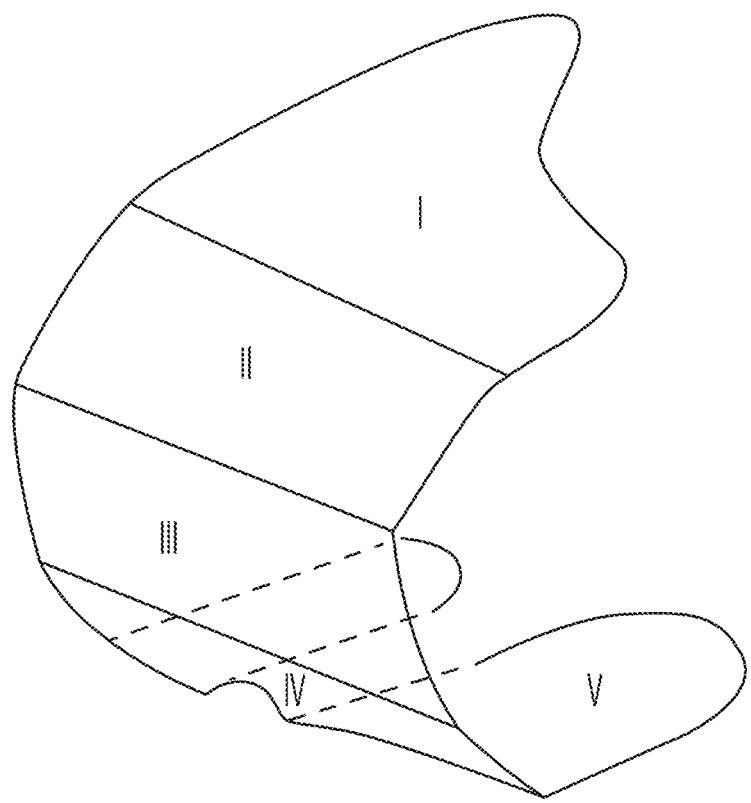
FIG. 30 illustrates an example three-dimensional outline representation of at least a portion of an outer surface of a periphery of a three-dimensional bone volume.

FIG. 30 illustrates an example three-dimensional outline representation 3000 of at least a portion of an outer surface of a periphery of a three-dimensional bone volume. In this example, the portion of the bone corresponds to a distal end of a femur. As shown, FIG. 30 provides an isometric view of a three-dimensional box cut on a distal end of a femur. The three-dimensional box cut has been labelled in five segments that correspond to the resection cuts used in determining the three-dimensional box cut. For instance, a first segment, "I," corresponds to an anterior flange cut segment, a second segment, "II," corresponds to an anterior chamfer cut segment, a third segment, "III," corresponds to a distal cut segment, a fourth segment, "IV," corresponds to a posterior chamfer cut segment, and a fifth segment, "V," corresponds to a posterior condyles cut segment. In this example, to assemble the complete bone cut boundary shape for a femoral implant, a modular approach is taken to characterize bone resection boundary shape and size.

Referring again to FIG. 29, the system 200 converts the three-dimensional outline representation into a two-dimensional outline representation of the portion of the outer surface of the periphery of the three-dimensional bone volume (2940). For instance, the system 200 processes the three-dimensional outline representation to flatten or project the three-dimensional outline representation onto a two-dimensional plane. In flattening or projecting the three-dimensional outline representation onto a two-dimensional plane, the system 200 orients each segment of the three-dimensional outline representation to be parallel to one another with edges of adjacent segments aligned.

In some examples, the system 200 converts the three-dimensional outline representation into a two-dimensional outline representation that has a thickness to account for one or more tolerances for one or more variations related to an implant procedure for placing the implant on the portion of the bone. In these examples, the system 200 determines a thickness needed to account for the one or more tolerances for the one or more variations and defines the two-dimensional outline representation to have the determined thickness. The thickness may vary across the two-dimensional outline representation as the tolerances for variations may be different at different portions of the two-dimensional outline representation.

In some implementations, the system 200 offsets the two-dimensional outline representation to reduce the likelihood of overhang of the implant on the portion of the bone. In these implementations, the system 200 offsets the two-dimensional outline representation away from edges of the bone to reduce the likelihood of overhang. The system 200 may use an offset of two millimeters to reduce the likelihood of overhang while providing a suitable fit.

Figure 31:
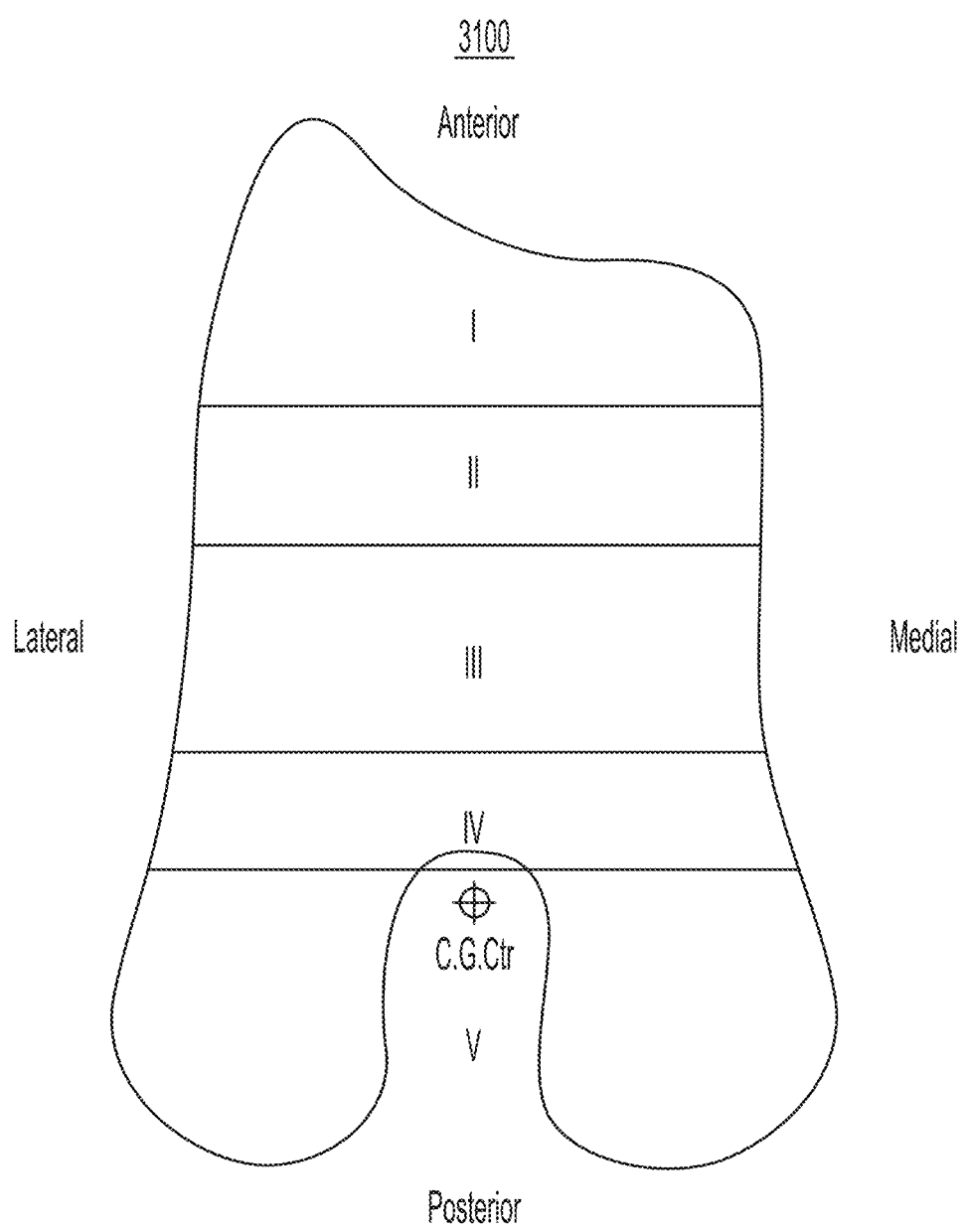
FIG. 31 illustrates an example two-dimensional outline representation of a portion of an outer surface of a periphery of a three-dimensional bone volume.

FIG. 31 illustrates an example two-dimensional outline representation 3100 of a portion of an outer surface of a periphery of a three-dimensional bone volume. In this example, the portion of the bone corresponds to a distal end of a femur. As shown, FIG. 31 shows the three-dimensional box cut from FIG. 30 converted to two dimensions on a single plane. The plane may have a thickness making it a three-dimensional composite volume to account for variation in bone resections. The two-dimensional box cut (with potential thickness) has been labelled in five segments that correspond to the resection cuts used in determining the two-dimensional box cut. For instance, a first segment, "I," corresponds to an anterior flange cut segment, a second segment, "II," corresponds to an anterior chamfer cut segment, a third segment, "III," corresponds to a distal cut segment, a fourth segment, "IV," corresponds to a posterior chamfer cut segment, and a fifth segment, "V," corresponds to a posterior condyles cut segment. In addition, a location of the cruciate gap center on the two-dimensional box cut has been illustrated.

Referring again to FIG. 29, the system 200 segments the two-dimensional outline representation into segments that correspond to the resection cuts used in fitting the implant on the portion of the bone (2950). For example, the system 200 identifies locations of edges of adjacent resections cuts on the two-dimensional outline and separates the two-dimensional outline at the located edges. In this example, each segment corresponds to a particular resection cut and includes data representing an outline of the bone at the particular resection cut. The outline data for a resection cut may be a continuous line or may be broken up into multiple different lines. For instance, for each resection cut, the outline data may represent a first outline of the bone at a lateral side and a second outline of the bone at a medial side. Data representing the resection cut boundaries may or may not be stored as part of the segments of the two-dimensional outline representation.

In implementations in which the portion of the bone is a distal end of a femur, the system 200 segments the two-dimensional outline representation into five different segments. In this regard, the system 200 segments the two-dimensional outline representation into a first segment that corresponds to a distal face of the distal end of the femur, a second segment that corresponds to an anterior chamfer of the distal end of the femur, a third segment that corresponds to a posterior chamfer of the distal end of the femur, a fourth segment that corresponds to an anterior flange of the distal end of the femur, and a fifth segment that corresponds to posterior condyles of the distal end of the femur.

Figure 32:
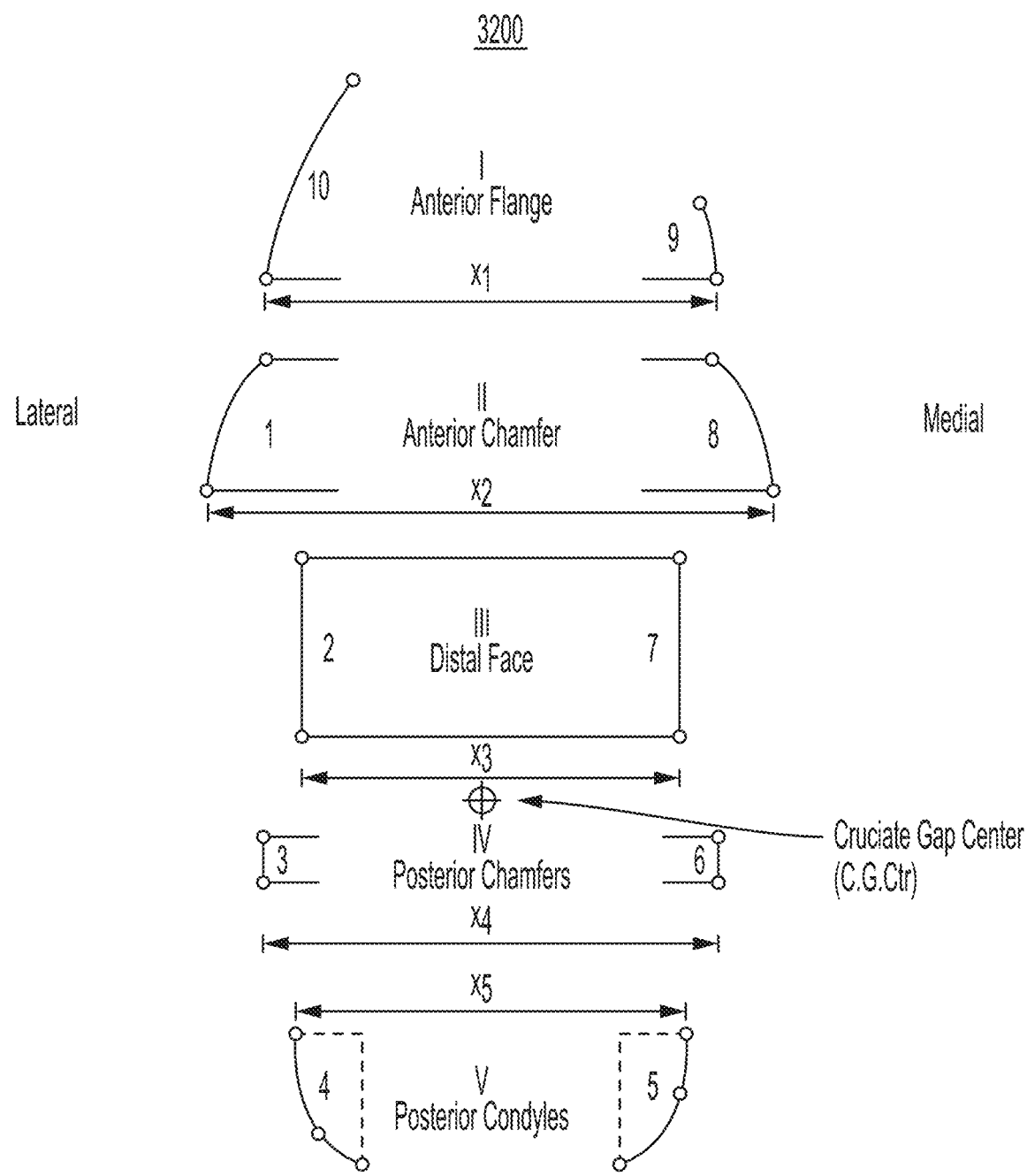
FIG. 32 illustrates an example of a segmented two-dimensional outline representation.

FIG. 32 illustrates an example of a segmented two-dimensional outline representation 3200. In this example, the portion of the bone corresponds to a distal end of a femur. As shown, FIG. 32 shows the two-dimensional box cut from FIG. 31 separated into five "buckets" of spline cut segments; namely, one group for each face of the box cut.

The segmented two-dimensional box cut (with potential thickness) has been labelled in five segments that have been separated. For instance, a first segment, "I," corresponds to an anterior flange cut segment, a second segment, "II," corresponds to an anterior chamfer cut segment, a third segment, "III," corresponds to a distal cut segment, a fourth segment, "IV," corresponds to a posterior chamfer cut segment, and a fifth segment, "V," corresponds to a posterior condyles cut segment. In addition, a location of the cruciate gap center on the segmented two-dimensional box cut has been illustrated.

Referring again to FIG. 29, the system 200 performs one or more operations related to implant matching based on the segments that correspond to the resection cuts used in fitting the implant on the portion of the bone (2960). For instance, the system 200 may design a custom implant based on the segments, use the segments in generating a library of implants, and/or use the segments to select, from a library of implants, an implant to use in an implant procedure. In designing a custom implant, the system 200 may input outline data for each of the segments to an implant manufacturing application and the implant manufacturing application may generate a design of an implant that corresponds to the outline data. In this regard, the system 200 may input multiple spline segments that define the outline data and the implant manufacturing application may generate additional splines used to develop the custom implant. The implant manufacturing application may start with the segment that requires the best fit to obtain an implant with the best fit on that segment and then work outward to segments that do not require as good a fit or whose fit is dependent on the segment that requires the best fit. For instance, in designing a custom femoral component of a knee implant, the system 200 may start within the segment corresponding to the distal face, define the portion of the implant for the distal face, then define the portion of the implant for the anterior and posterior chamfers, and finally define the portion of the implant for the anterior flange and posterior condyles.

In some implementations, the system 200 offsets the segments in designing an implant. In these implementations, the system 200 may slightly reduce how far the outer surface of outline data for the segments extends (e.g., slightly shrinks the outline data) and may use the reduced version of the outline data as a basis for designing the implant. The system 200 may define the amount of reduction in accordance with implant manufacturing tolerances to reduce the risk of manufacturing variations causing the implant to overhang at one or more portions of the bone. For example, the system 200 may offset outline data by two millimeters prior to using the outline data to generate an implant design. Offsetting the outline data may be necessary to account for differences between the source data and the actual size of patient bones versus the CAD models. In offsetting the outline data, the system 200 may offset the implant model perimeter approximately 3.5 mm inside the bone model perimeter.

In implementations in which the portion of the bone is a distal end of a femur, each of the five buckets or segments is clustered into groups of similar shape and size or shape independent of size. To fit a new patient, the complete implant bone cut boundary is then reassembled starting with the best matching distal face (bucket III), and then adding the best matching anterior chamfer and posterior chamfer to the distal face, and finally adding the anterior flange and posterior condyles. To achieve a best possible fit all around the bone cut boundary, the medial-lateral width, "x", for each bucket, e.g. x1 for bucket "I", x2 for bucket "II", x3 for bucket "III", x4 for bucket "IV", x5 for bucket "V", can be changed to best match the patient's distal femur medial-lateral size. To align the cruciate gap of the implant with the cruciate gap of the femur, a "cruciate gap center" (C.G. Ctr) is landmarked. After the complete bone cut boundary is assembled, it is analytically verified to meet underhang and overhang constraints specified for the patient specific knee implant system. Once verified, the CNC code for the total bone cut boundary is compiled with a standard library of CNC code for articular surfaces, box cut features, lugs, and other geometric features, and the implant is machined using CNC machine tools, much the same as a standard Legion® femoral implant would be machined. Medial-Lateral positioning instruments, e.g. a ML Positioner, can be made using the same bone cut boundary shapes and sizes as the femoral implant.

In some examples, by reducing the total number of "pre-programmed" CNC files to a smaller set, e.g., ten to twenty programs per bucket per box cut size, management of programs may be more efficient, and the total number of possible discrete implant sizes is significantly larger, improving the fit for a larger population of patients, e.g. twenty spline pairs per bucket*five buckets*five box cut sizes*two hands (left and right)*two implant families (CR & PS)=total two thousand sizes, and five hundred CNC programs. This example assumes programs can include a "mirror" feature for doing left and right hand sizes from the same base program.

Figure 33:
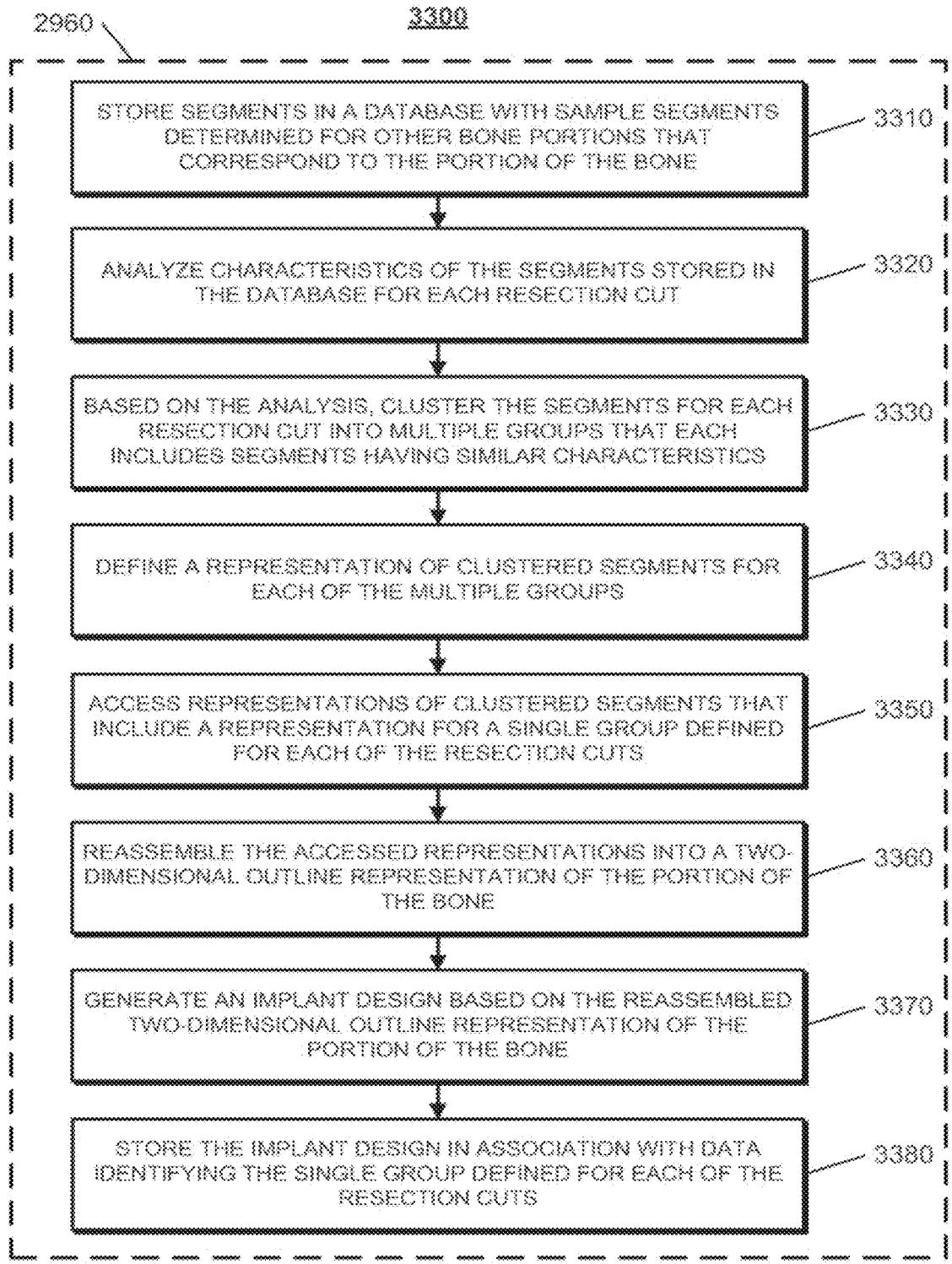

FIG. 33 illustrates a process 3300 for generating a library of implant designs. The process 3300 may be used in performing one or more operations related to implant matching based on the segments that correspond to the resection cuts used in fitting the implant on the portion of the bone referenced above with respect to reference numeral 2960. The operations of the process 3300 are described generally as being performed by the system 200. In some implementations, operations of the process 3300 may be performed by one or more processors included in one or more electronic devices.

The system 200 stores each segment in a database with sample segments determined for the particular resection cut on other bone portions that correspond to the portion of the bone associated with the segment (3310). For instance, the system 200 maintains a database of sample outline data for segments corresponding to a particular resection cut for a particular bone (e.g., a first bucket of segments for an anterior flange of a distal end of a femur, a second bucket of segments for an anterior chamfer of a distal end of a femur, a third bucket of segments for a distal face of a distal end of a femur, a fourth bucket of segments for a posterior chamfer of a distal end of a femur, and a fifth bucket of segments for posterior condyles of a distal end of a femur) and adds each segment to the appropriate portion of the database (e.g., the appropriate bucket). The sample outline data may include outline data determined for many different patients, including outline data determined for bones of cadavers analyzed during a cadaver study. The sample outline data may correspond to segments of the particular bone (e.g., an anterior flange profile of a distal end of femur). The system 200 also may store, in the database, other patient information related to the patient (e.g., age, gender, ethnicity, weight, height, etc.) and/or information related to the particular bone (e.g., size measurements of the particular bone). The system 200 may use the other patient information to assist in grouping the sample outline data for each resection cut and matching a new patient to a grouping of the sample segments.

The system 200, for each resection cut, analyzes characteristics of the segments stored in the database for the resection cut (3320). For example, the system 200 determines size and/or shape characteristics of the sample segments stored in the database and compares the determined size and/or shape characteristics of the sample segments to one another. In this example, the system 200 determines a level of similarity between sample segments based on the comparison.

In some implementations, the system 200 uses size and/or shape characteristics of entire sample segments in performing the analysis. In other implementations, the system 200 uses size and/or shape characteristics of portions of sample segments in performing the analysis. For instance, the system 200 may select a subset of positions along the sample segments and use size and/or shape characteristics of each of the subset of positions in the analysis. In implementations in which the techniques described throughout this disclosure are used in knee implants (e.g., TKA), the system 200 may select several points along a representation of an anterior flange, determine location information of each of the several points, and use the location information in the analysis.

The system 200, based on the analysis, clusters the segments stored in the database for the resection cut into multiple groups that each includes segments having similar characteristics (3330). For instance, the system 200 uses a clustering process to group the sample segments into multiple, different groups of sample segments that have similar size and/or shape characteristics. The system 200 may perform the clustering based on the comparison of size and/or shape characteristics of the sample segments. The system 200 may perform clustering by assigning a set of sample segments into groups (called clusters), so that the sample segments in the same cluster are more similar (in some sense or another) to each other than to those in other clusters.

Any type of one or more clustering processes may be used to arrange the sample segments into groups having similar size and/or shape characteristics. For instance, the system 200 may use a machine learning process to group sample segments with similar characteristics together. Example clustering processes the system 200 may use include one or more of connectivity-based clustering processes (e.g., hierarchical clustering processes), such as single-linkage clustering, complete linkage clustering, and average linkage clustering, centroid-based clustering processes, such as k-means clustering, k-medians clustering, and Fuzzy c-means clustering, distribution-based clustering processes, such as expectation-maximization (EM) clustering and mixture of Gaussians clustering, and density-based clustering processes, such as density-based spatial clustering of applications with noise (DBSCAN) and ordering points to identify the clustering structure (OPTICS).

After clustering, each bucket of segments for each resection cut has multiple groups of segments arranged in the bucket. For instance, in implementations in which the portion of the bone is a distal end of a femur, the segments in a first bucket corresponding to the anterior flange are clustered into multiple groups, the segments in a second bucket corresponding to the anterior chamfer are clustered into multiple groups, the segments in a third bucket corresponding to the distal face are clustered into multiple groups, the segments in a fourth bucket corresponding to the posterior chamfer are clustered into multiple groups, and the segments in a fifth bucket corresponding to the posterior condyles are clustered into multiple groups.

The system 200 defines, for each resection cut, a representation of clustered segments for each of the multiple groups (3340). For example, after the sample segments have been clustered into multiple groups with similar characteristics, the system 200 determines a representation of clustered segments for each group. In this example, the system 200 may analyze characteristics of each group and determine a best fit representation for the sample segments included in the particular group. After defining the representation for the particular group, the system 200 continues processing other groups of segments until a representation has been defined for each of the groups for each of the resection cuts.

In some implementations, to define a representation for a group of segments, the system 200 may compute an average representation by averaging data descriptive of the segments included in the group. In addition, to define a representation for a group of segments, the system 200 may use minimum and maximum criteria of the segments included in the group. For instance, the system 200 may define a combined representation based on minimum and maximum points of each of the segments included in the group such that all of the segments included in the group fit within the combined representation.

After defining a representation for each of the multiple groups, the system 200 may evaluate the defined representation for each group. For example, after the system 200 has defined a representation for a particular group, the system 200 may compare the implant design to each of the segments included in the particular group and, based on the comparison, determine how closely the representation matches each of the segments included in the particular group. Based on the determinations of how closely the representation matches each of the segments included in the particular group, the system 200 may determine whether the representation matches each of the segments included in the particular group within a threshold degree. Based on a determination that the representation matches each of the segments included in the particular group within the threshold degree, the system 200 determines that the representation is sufficient for the particular group and assigns the representation to the particular group.

However, based on a determination that the representation does not match one or more of the segments included in the particular group within the threshold degree, the system 200 may reject the representation and provide an alert indicating the representation is insufficient for the particular group. After rejecting the representation, the system 200 may attempt to use another technique to generate a new representation based on the segments included in the particular group. The system 200 may evaluate the new representation to determine whether the new representation matches each of the segments included in the particular group within the threshold degree. The system 200 may continue to attempt new representations for the particular group until the system 200 determines that a representation matches each of the segments included in the particular group within the threshold degree or that all techniques for generating a representation based on the segments included in the particular group have been attempted without success.

In some examples, after rejecting the representation or after determining that all techniques for generating a representation based on the segments included in the particular group have been attempted without success, the system 200 determines to perform additional clustering on the segments included in the particular group to divide the particular group into smaller groups of segments. In these examples, the system 200 repeats the clustering operations described above with parameters that result in a closer degree of similarity between the segments in the groups. After reclustering, the system 200 repeats the operations described above with respect to generating a representation for each group and evaluating representations until an acceptable representation has been defined for each group.

In some implementations, after rejecting the representation or after determining that all techniques for generating a representation based on the segments included in the particular group have been attempted without success, the system 200 may remove problematic segments from the particular group such that the implant design matches each of the remaining segments included in the particular group within the threshold degree. In these implementations, the system 200 may attempt to cluster removed segments into other groups (e.g., new groups) or may determine to leave the removed segments without a corresponding representation in the library. For example, the system 200 may determine to stop clustering and defining new representations when the library covers a threshold percentage (e.g., eighty percent) of sample segments within a threshold degree.

In some examples, the system 200 may receive new sample segments from new patients. In these examples, the system 200 may use the new sample segments from new patients to update the clustering of sample segments in the database and define (or redefine) representations to expand the coverage of the library.

The system 200 accesses representations of clustered segments that include a representation of clustered segments for a single group defined for each of the resection cuts (3350). For example, the system 200 accesses one representation for each resection cut such that the system 200 accesses a set of representations that corresponds to all segments needed for an implant. The system 200 may access every combination of the groups of clustered segments in designing implant designs or may access a subset of the potential combinations. In accessing a subset of the potential combinations, the system 200 may consider characteristics of the representations of the clustered segments and only uses representations that are similar enough to generate a reasonably useful implant design. For instance, the system 200 may consider the medial-lateral width of the representations and use combination in which all representations have a medial-lateral width that is within a threshold degree.

The system 200 reassembles the accessed representations into a two-dimensional outline representation of the portion of the bone (3360). For instance, the system 200 reverses the process used to segment the two-dimensional outline representation of the portion of the bone and regenerates a two-dimensional outline representation based on the accessed representations. In some examples, the system 200 identifies locations of edges of segments corresponding to adjacent resections cuts and joins the segments at the located edges. In these examples, the system 200 may align the widths of the adjacent segment as best as possible and may smooth the resulting two-dimensional outline representation at points of discontinuity caused by slight differences in widths of the segments. The system 200 may determine a reassembled two-dimensional outline representation that represents a best fit of the accessed representations.

In some implementations, the two-dimensional outline representation referenced in the present application may refer to discrete landmark points, rather than a complete outline. In these implementations, three-dimensional bone surface ribbons and discrete landmark points may be reduced to a two-dimensional dataset by, for example, ignoring the Z-coordinate. The reduced two-dimensional (x,y) data from the three-dimensional bone surface ribbons may be applied to the approaches to modular clustering and implant matching described throughout this disclosure.

The system 200 generates an implant design based on the reassembled two-dimensional outline representation of the portion of the bone (3370). For example, after the sample segments have been clustered into multiple groups with similar characteristics for each resection cut, the system 200 determines an implant design for a particular set of groups using the reassembled two-dimensional outline representation for the particular set of groups. The system 200 then may use the reassembled two-dimensional outline representation to define an implant design for the particular set of groups using the techniques described above with respect to defining a custom implant using an outline representation. After defining the implant design for the particular set of groups, the system 200 continues processing other sets of groups of segments until an implant design has been defined for each potential combination of groups or for each potential combination of groups that are similar enough to generate a reasonably useful implant design.

In some examples, the rules applied to generate a particular implant design include user needs constraints specifying where around the implant boundary or perimeter that implant overhang beyond bone cut perimeters and bone underhang beyond the implant boundary or perimeter by boundary zone are specified. These boundary constraints address risks including soft tissue risk, load transmission from implant to cortical (more dense outer bone), minimizing blood loss, and other known risks. Design team surgeons may evaluate and validate the designs and the system 200 may adapt the designs based on user input specifying recommendations of the design team surgeons.

The system 200 stores the implant design in association with data identifying the single group defined for each of the resection cuts (3380). For instance, the system 200 may store, in association with data identifying the implant design, data identifying the combination of groups corresponding to the implant design. The system 200 further may store, in association with data identifying the implant design, bone size measurements and other patient data (e.g., age, gender, ethnicity, weight, height, etc.) that may be useful in determining whether or not a patient matches the implant design. The system 200 may store any type of data that enables matching of patient bone data to an implant in the library of implants.

In some implementations, the system 200 may use the clustering techniques described throughout this disclosure (e.g., the process 3300) to cluster combined edges. For example, the system 200 may cluster the sides of the implant (e.g., distal, and chamfer cuts) as one group of clustered segments and then cluster the posterior and anterior tips as separate entities. Similarly, the system 200 may cluster the sides medial and lateral separately, but with each side as an independent member of the library of "sizes." The clustered segments of combined edges then may be matched and generally used in the same manner as the individual clustered segments described throughout this disclosure.

Figure 34:
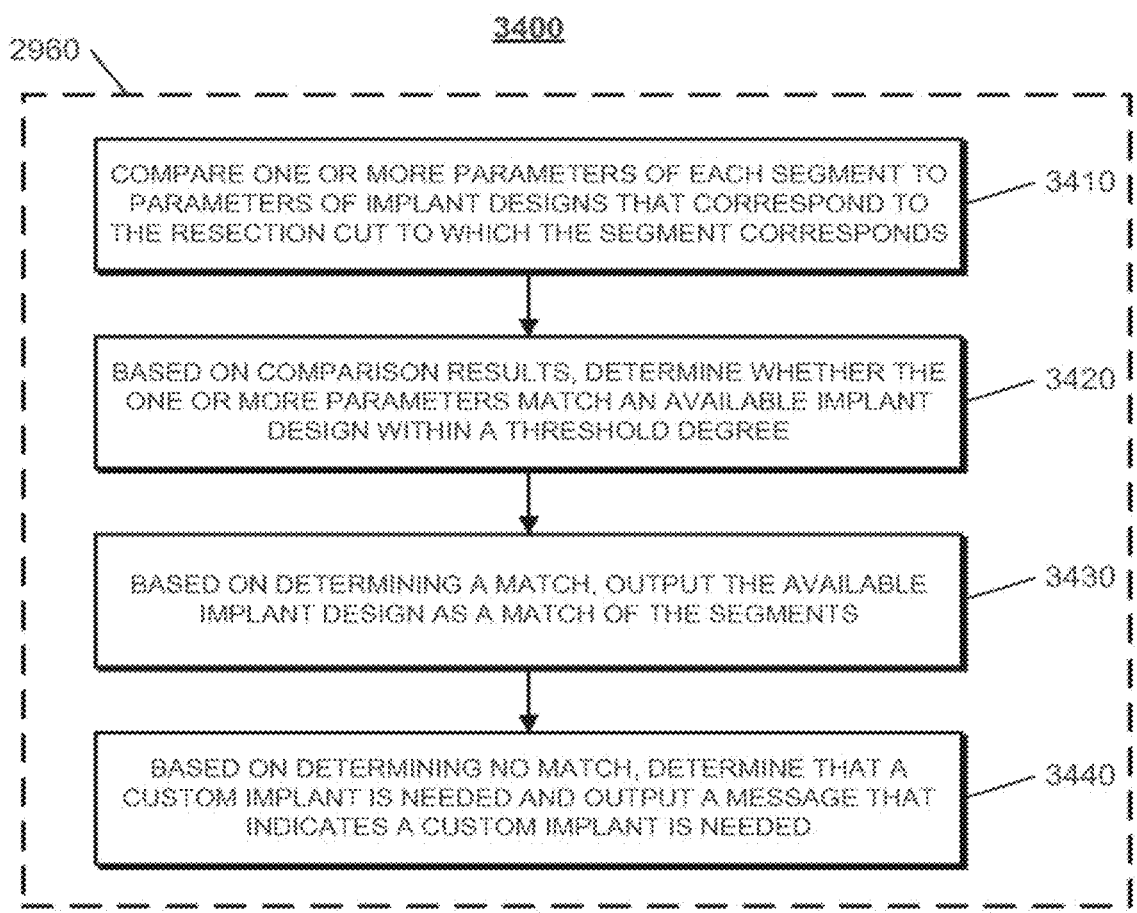

FIG. 34 illustrates a process 3400 for matching patient data to an implant. The process 3400 may be used in performing one or more operations related to implant matching based on the segments that correspond to the resection cuts used in fitting the implant on the portion of the bone referenced above with respect to reference numeral 2960. The operations of the process 3400 are described generally as being performed by the system 200. In some implementations, operations of the process 3400 may be performed by one or more processors included in one or more electronic devices.

The system 200, for each segment, compares one or more parameters of the segment to parameters that are associated with available implant designs and that correspond to the particular resection cut to which the segment corresponds (3410) and, based on comparison results, determines whether the one or more parameters match an available implant design within a threshold degree (3420). For instance, for a particular resection cut, the system 200 may access parameters stored in association with groups of clustered segments stored in the library for the particular resection cut and compare the one or more parameters of a segment for the particular resection cut to the accessed parameters. Based on the comparison of the one or more parameters of the segment for the particular resection cut to the accessed parameters, the system 200 determines whether the one or more parameters of a segment for the particular resection cut match the accessed parameters within a threshold degree.

In some examples, the system 200 may compare a shape of the segment to shapes of outer perimeters of representations stored in the library of implant designs. In these examples, based on the comparison of the shape of the segment to shapes of outer perimeters of representations stored in the library, the system 200 determines whether the shape of the segment exactly matches a shape of an outer perimeter of a representation stored in the library or matches a shape of an outer perimeter of a representation stored in the library within a threshold tolerance zone (e.g., matches the outer perimeter within two millimeters at all locations).

In some implementations, the system 200 may determine size measurements of the segment and first compare the determined size measurements to sizes of representations stored in the library. In these implementations, the system 200 may, based on the comparison, select a subset of representations within the library that are acceptable for the determined size measurements. Although each of the subset of representations is acceptable for the size of the segment, each of the subset of representations has a different shape for an outer perimeter of the representation. Accordingly, after selecting the subset, the system 200 performs a second comparison to select the representation that best matches a shape of the segment. In this regard, the system 200 compares the one or more parameters of the segment to parameters associated with each of the subset of representations to assess whether a shape of the segment matches a shape of any of the subset of representations.

For instance, the system 200 may determine size and/or shape characteristics of the segment. The system 200 also may determine position data for portions of the segment that enables matching to representations in the library. The system 200 may determine any type of parameters that enable matching of the segment to a representation in the library of implants, including the parameters stored in association with representations in the process 3300. The system 200 may use the segment itself as the one or more parameters.

In some implementations, the system 200 may process each segment and determine a matching group of clustered segments for each segment. In these implementations, the system 200 may process the segments in parallel, in serial, or in a serial and parallel manner. For instance, in implementations in which the portion of the bone is a distal end of a femur, the system 200 may start with a first segment corresponding to the distal face of the femur and determine, for the first segment, a matching group of clustered segments that correspond to the distal face. After determining the match for the distal face, the system 200 proceeds to analyze a second segment corresponding to the anterior chamfer of the femur and a third segment corresponding to the posterior chamfer of the femur. In analyzing the second segment and the third segment, the system 200 only considers groups that are compatible with the matching group of clustered segments that correspond to the distal face. The system 200 determines, for the second segment, a matching group of clustered segments that correspond to the anterior chamfer and determines, for the third segment, a matching group of clustered segments that correspond to the posterior chamfer, or determines that a match cannot be found. To the extent matches for the second and third segments are found, the system 200 proceeds to analyze a fourth segment corresponding to the anterior flange of the femur and a fifth segment corresponding to the posterior condyles of the femur. In analyzing the fourth segment and the fifth segment, the system 200 only considers groups that are compatible with the matching group of clustered segments that correspond to the distal face, the matching group of clustered segments that correspond to the anterior chamfer, and the matching group of clustered segments that correspond to the posterior chamfer. The system 200 determines, for the fourth segment, a matching group of clustered segments that correspond to the anterior flange and determines, for the fifth segment, a matching group of clustered segments that correspond to the posterior condyles, or determines that a match cannot be found. The system 200 then determines whether an available implant design matches the segments based on whether all five segments were matched or not. If all five segments were matched, the system 200 identifies an available implant design designed for the combination of groups matched. If all five segments were not matched, the system 200 determines that no available implant design matches within a threshold degree.

In implementations in which the segments are processed in parallel, the system 200 first determines whether a matching group of clustered segments was found for each segment. If a matching group of clustered segments was not found for each segment, the system 200 determines that no available implant design matches within a threshold degree. If a matching group of clustered segments was found for each segment, the system 200 determines whether an available implant design has been defined for the combination of matching groups. For instance, a particular combination of groups may be rare and, therefore, an implant design may not be defined in the library for the particular combination and, thus, an implant design in the library is not available, even though a matching group of clustered segments was found for each segment. If an available implant design has been defined for the combination of matching groups, the system 200 identifies the available implant design designed for the combination of groups matched. If an available implant design has not been defined for the combination of matching groups, the system 200 determines that no available implant design matches within a threshold degree.

The system 200, based on determining a match, outputs the available implant design as a match of the segments (3430). For instance, the system 200 may display the matching implant design to a surgeon (or other medical care provider) for use in an implant procedure. If the system 200 determines that multiple implant designs match the segments within the threshold degree, the system 200 may display each of the multiple implant designs to enable a surgeon to select the preferred implant design for the implant procedure.

In determining a match, the system 200 locates a "best" match that is not necessarily a "perfect" match, e.g. the system 200 may pick a size or several sizes from the implant library that fit "best" while not meeting all the constraints required to be considered a "perfect" match. Accordingly, the system 200 selects the best match of a discrete size from a pre-existing library matched to fit new patients. The system 200 may use the best match as long as the best match fits the new patient within a threshold degree.

The system 200, based on determining no match within a threshold degree, determines that a custom implant is needed and outputs a message that indicates a custom implant is needed (3440). For instance, the system 200 may display a message indicating that no match was found in the library of implants. The system 200 also may initiate a process to define a custom implant for the portion of the bone based on the determination that no match exists within the threshold degree.

In some examples, the system 200 constructs clusters of bones in addition or as an alternative to clusters of contours. In these examples, the system 200 may combine the solids of the bones into minimum and maximum bones after the bones have been grouped in clusters. The system 200 then may place the seed implant spline on the contour of the ribbon from that composite bone.

Figure 35:
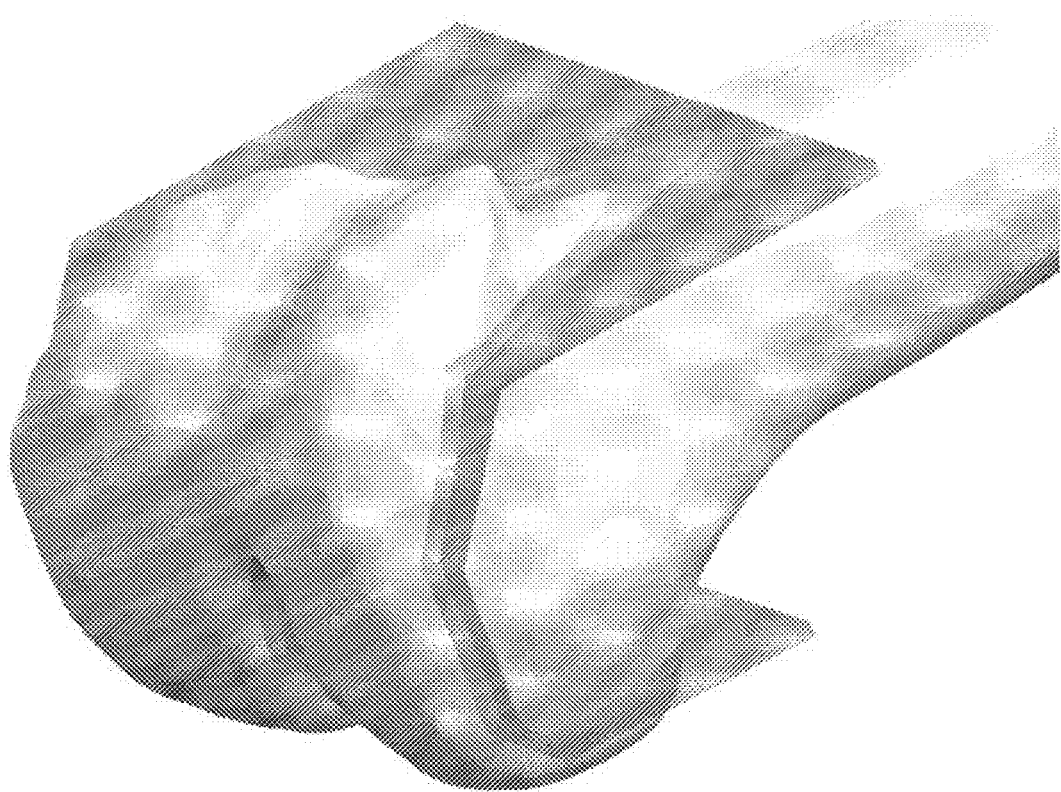
Figure 36:
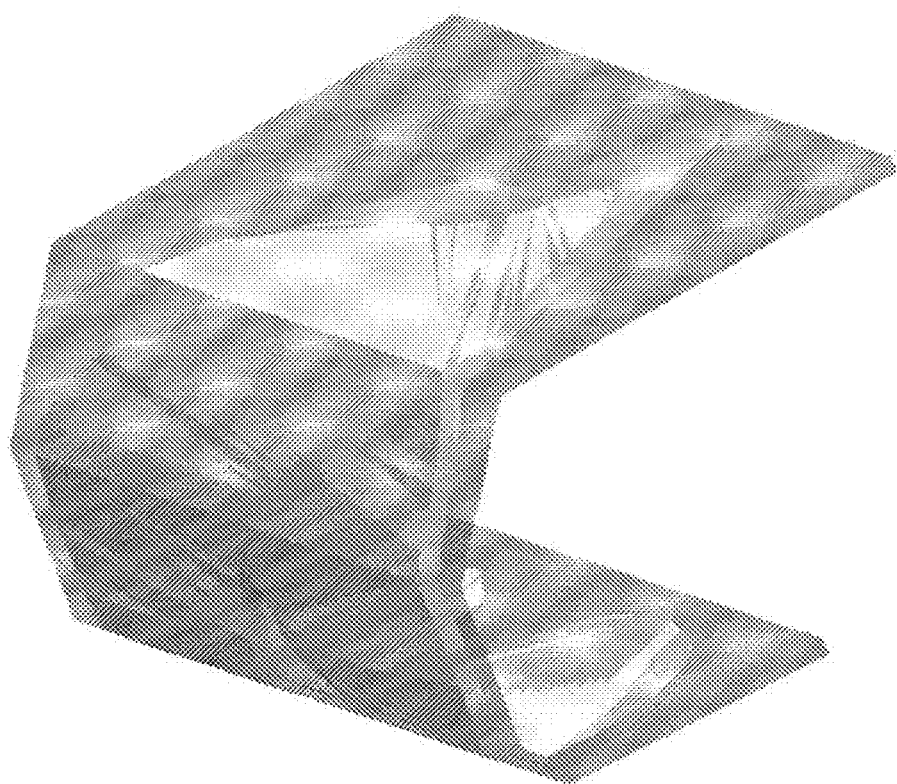
Figure 37:
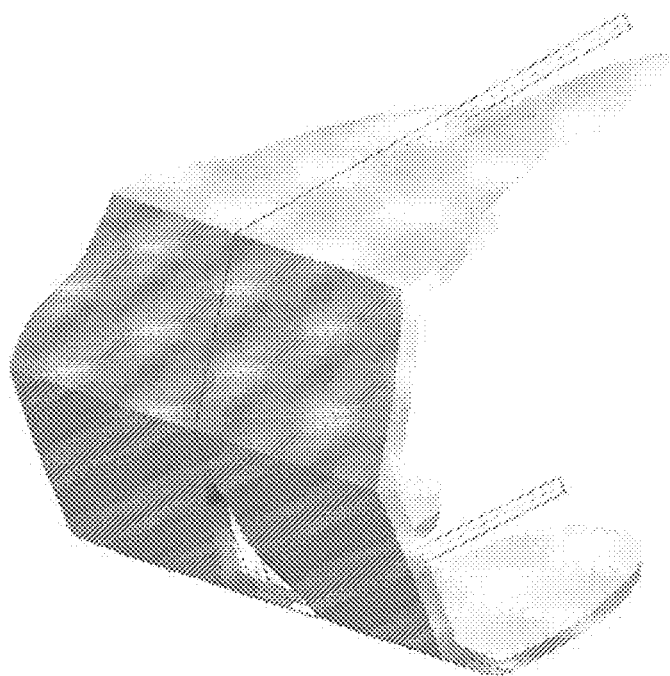
Figure 38:
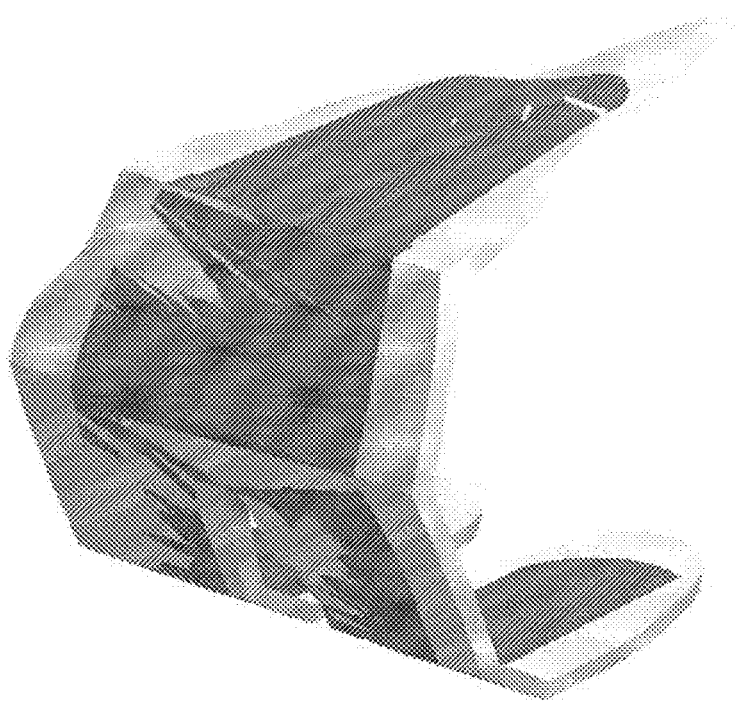
Figure 39:
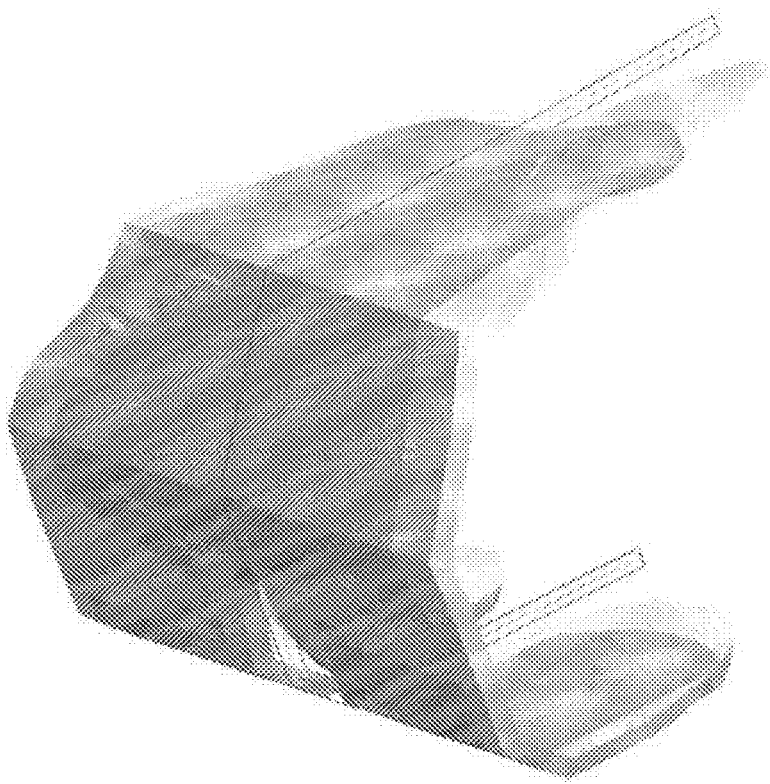
Figure 40:
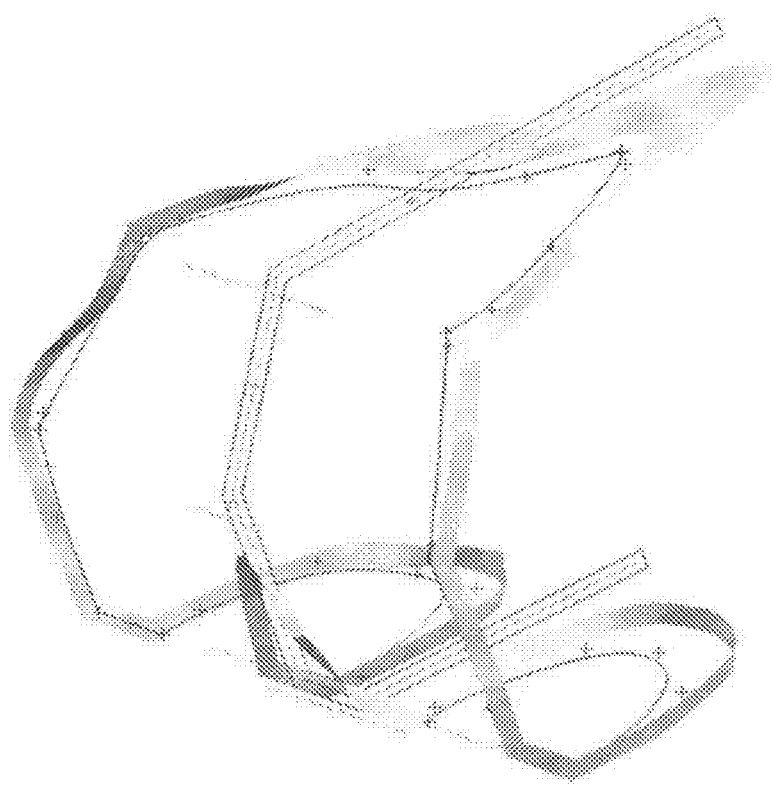

FIGS. 35-49 are example interfaces that illustrate an example of using a modular process to select or create a patient specific knee implant. The example interfaces may be generated and used in performing the process 2900 described above with respect to FIG. 29. FIG. 35 shows a representation 3500 of a three-dimensional bone volume intersected with a three-dimensional tolerance volume based on locations of resections cuts used in fitting an implant on the three-dimensional bone volume. FIG. 36 shows a representation 3600 of the three-dimensional bone volume and the three-dimensional tolerance volume from FIG. 35 with portions of the three-dimensional bone volume outside of the three-dimensional tolerance volume removed. FIG. 37 shows a representation 3700 of a remaining portion of the three-dimensional bone volume from FIG. 35 after intersection with the three-dimensional tolerance volume. FIG. 38 shows a representation 3800 of the remaining portion of the three-dimensional bone volume from FIG. 37 after being modified to account for a safe zone for a periphery of an implant. FIG. 39 shows a representation 3900 of the modified portion of the three-dimensional bone volume from FIG. 38 after being modified to account for an implant tolerance zone defined based on sizing of the implant and one or more tolerances for one or more variations related to an implant procedure. FIG. 40 shows a representation 4000 of a bone surface ribbon generated from the volume shown in FIG. 39 and control points for a spline fitted to the bone surface ribbon.

Figure 41:
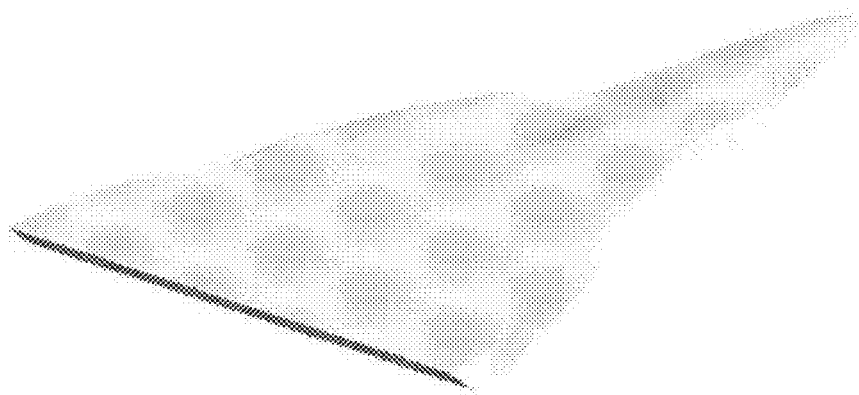
Figure 42:
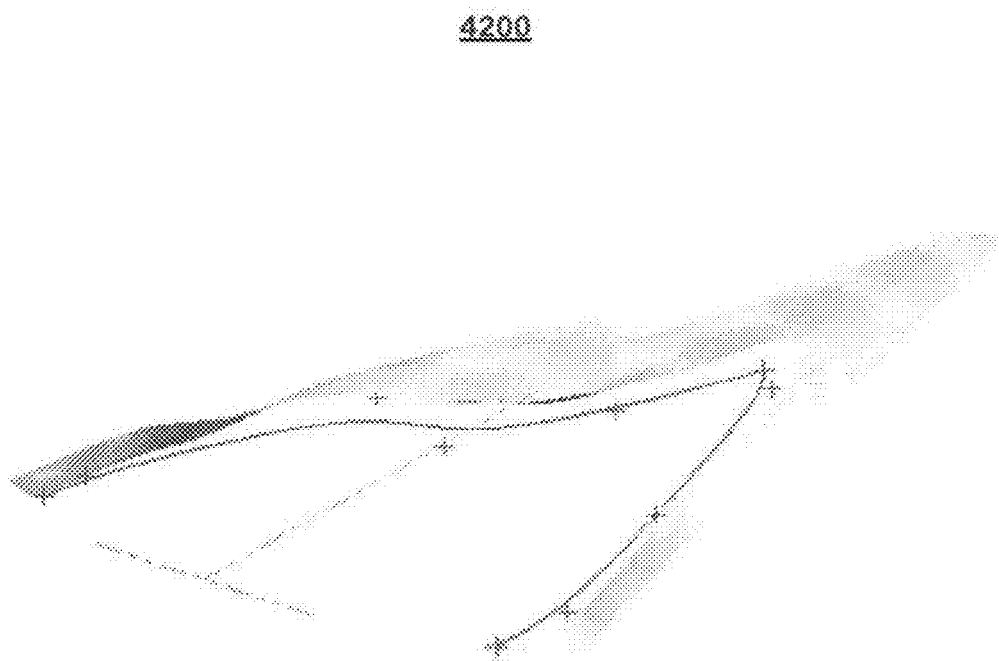
Figure 43:
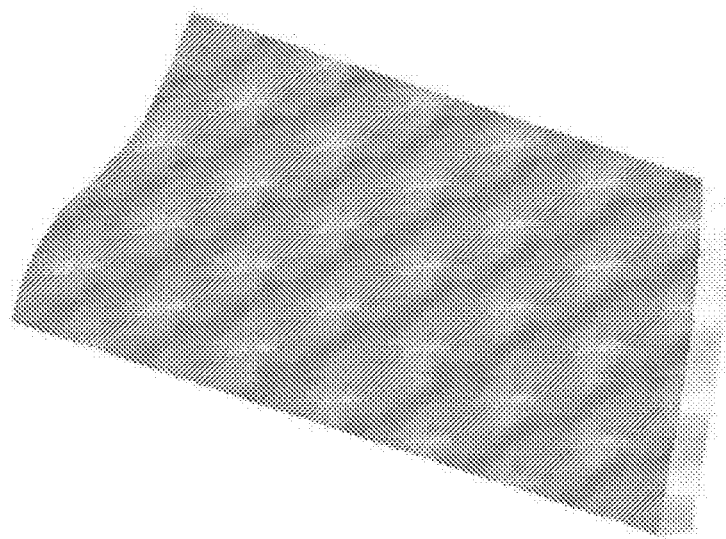
Figure 44:
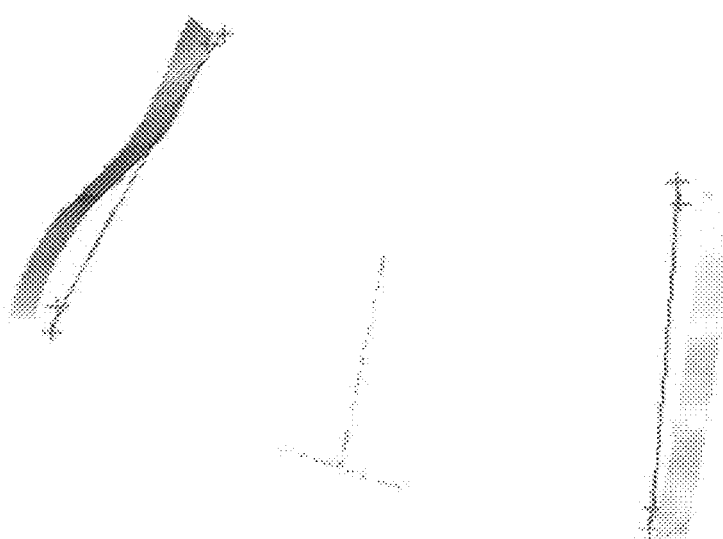
Figure 45:
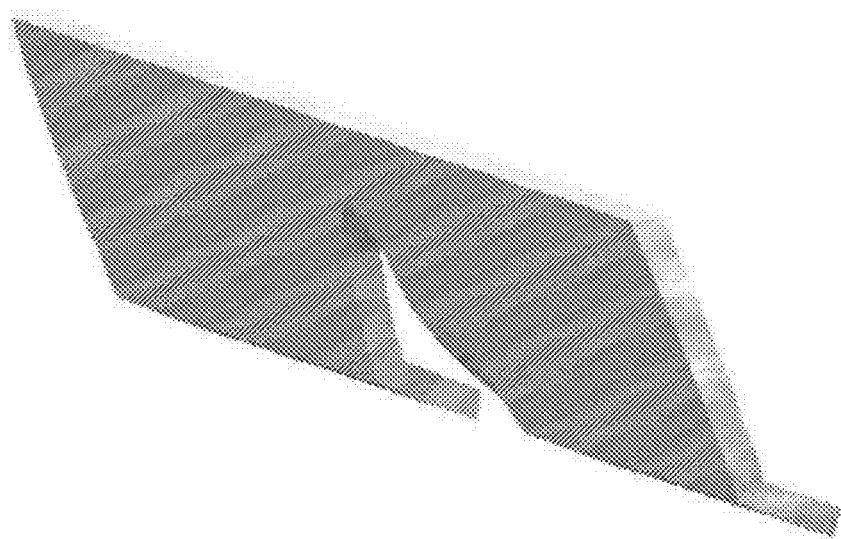
Figure 46:
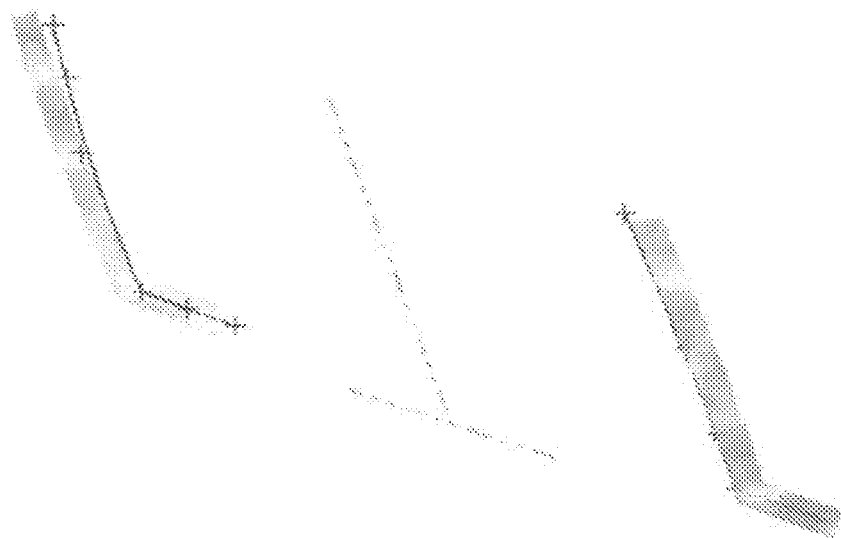
Figure 47:
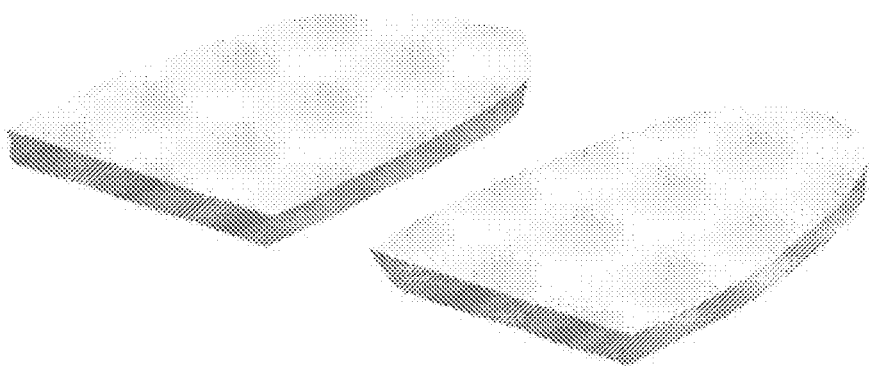
Figure 48:
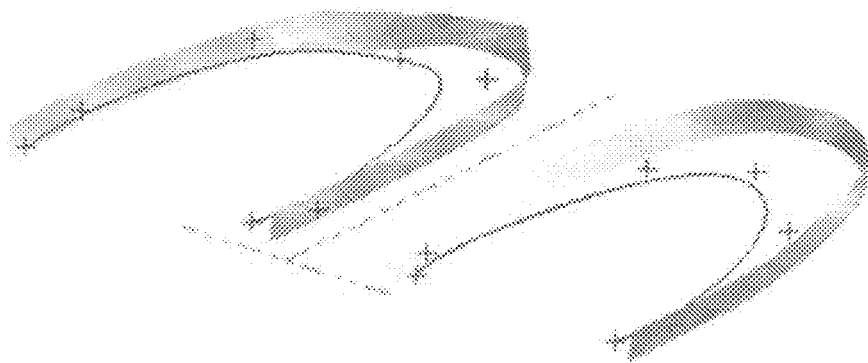

FIGS. 41-48 illustrate segments of bone data generated from the bone data shown in FIGS. 39 and 40. FIG. 41 shows a representation 4100 of the portion of the bone data shown in FIG. 39 that corresponds to the anterior flange. FIG. 42 shows a representation 4200 of the portion of the bone surface ribbon and control points shown in FIG. 40 that corresponds to the anterior flange. FIG. 43 shows a representation 4300 of the portion of the bone data shown in FIG. 39 that corresponds to the anterior chamfer cut. FIG. 44 shows a representation 4400 of the portion of the bone surface ribbon and control points shown in FIG. 40 that corresponds to the anterior chamfer cut. FIG. 45 shows a representation 4500 of the portion of the bone data shown in FIG. 39 that corresponds to the distal and posterior chamfer cuts. FIG. 46 shows a representation 4600 of the portion of the bone surface ribbon and control points shown in FIG. 40 that corresponds to the distal and posterior chamfer cuts. FIG. 47 shows a representation 4700 of the portion of the bone data shown in FIG. 39 that corresponds to the posterior condyles. FIG. 48 shows a representation 4800 of the portion of the bone surface ribbon and control points shown in FIG. 40 that corresponds to the posterior condyles.

Figure 49:
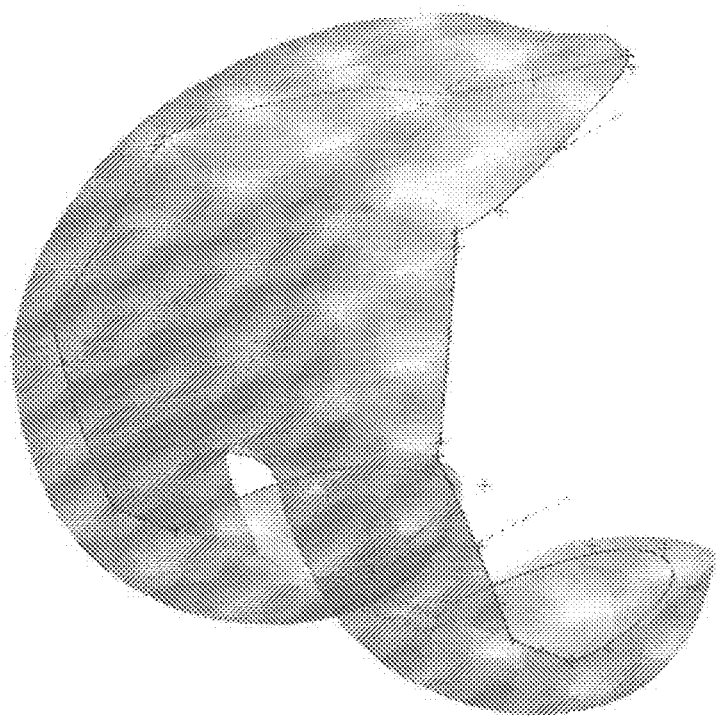

FIG. 49 shows a representation 4900 of a patient specific implant based on the bone sections shown in FIGS. 41-48. The patient specific implant may be an implant selected from a library of available implant designs using the techniques described above with respect to FIG. 34. The patient specific implant may be a custom implant designed based on the bone sections shown in FIGS. 41-48.

FIG. 50 illustrates an example of a generic computer system 2000. The system 2000 can be used for the operations described in association with the approach 100 and the processes 300, 400, 700, 1600, 1700, 2900, 3300, and 3400, according to some implementations. The system 2000 may be included in the system 200.

The system 2000 includes a processor 2010, a memory 2020, a storage device 2030, and an input/output device 2040. Each of the components 2010, 2020, 2030, and 2040 are interconnected using a system bus 2050. The processor 2010 is capable of processing instructions for execution within the system 2000. In one implementation, the processor 2010 is a single-threaded processor. In another implementation, the processor 2010 is a multi-threaded processor. The processor 2010 is capable of processing instructions stored in the memory 2020 or on the storage device 2030 to display graphical information for a user interface on the input/output device 2040.

The memory 2020 stores information within the system 2000. In one implementation, the memory 2020 is a computer-readable medium. In one implementation, the memory 2020 is a volatile memory unit. In another implementation, the memory 2020 is a non-volatile memory unit.

The storage device 2030 is capable of providing mass storage for the system 1000. In one implementation, the storage device 2030 is a computer-readable medium. In various different implementations, the storage device 2030 may be a floppy disk device, a hard disk device, an optical disk device, or a tape device.

The input/output device 2040 provides input/output operations for the system 1000. In one implementation, the input/output device 2040 includes a keyboard and/or pointing device. In another implementation, the input/output device 2040 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The tangible computer-readable mediums described throughout this disclosure may be referred to as non-transitory computer-readable mediums. Non-transitory computer-readable mediums may include any type of hardware storage device and the term non-transitory may be used to distinguish from intangible information carriers, such as propagating signals.

There is also provided a method for locating an implant. The method includes the steps of: preparing a distal end of a femur; locating a maximum distal width of the distal end; placing an instrument on the prepared femur, moving the instrument in a medial-lateral direction to obtain equal perimeter offsets; pinning the instrument; and creating at least one lug hole in the distal end of the femur using the instrument. The instrument includes a distal cut surface portion; an anterior chamfer portion connected to the distal cut surface portion; anterior flange portion connected to the anterior chamfer portion; a posterior chamfer portion connected to the distal cut surface portion; and at least one paddle connected to the posterior chamfer portion. The step of creating at least one lug uses a drill, a reamer or a punch. In some embodiments, the method includes the steps of removing the instrument and implanting a knee prosthesis.

There is provided a method for manufacturing a positioner instrument. The method includes the steps of: obtaining image data; generating a ribbon using the image data; generating a spline using the ribbon; generating offset distances for at least one lug location; importing the spline into an instrument CAD model; placing the offset distances in the instrument CAD model; and outputting the instrument CAD model to a SLA file.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A method for optimizing autonomous implant matching, the method comprising:
    segmenting, by an implant matching computing device, two-dimensional outline representations of outer surfaces of peripheries of three-dimensional bone volumes generated from three-dimensional models of portions of bones and corresponding to resection cuts used in fitting an implant on the portions of the bones to generate a plurality of segments, the segmenting comprising:
        identifying, by the implant matching computing device, edge locations of adjacent resection cuts on the two-dimensional outline representation; and
        separating, by the implant matching computing device, the two-dimensional outline at the identified edge locations into non-contiguous sections to form the segments;
    storing, by the implant matching computing device, the plurality of segments in a database, each of the plurality of segments corresponding to a particular resection cut and including data representing an outline of the bone at the particular resection cut;
    analyzing, by the implant matching computing device, characteristics of the plurality of segments stored in the database for each of the resection cuts;
    clustering, by the implant matching computing device, the plurality of segments stored in the database for each of the resection cuts into a plurality of groups, each group comprising segments of the plurality of segments having similar physical characteristics; and
    defining, by the implant matching computing device, an average outline representation of the clustered segments for each of the plurality of groups.

2. The method of claim 1 further comprising:
    comparing, by the implant matching computing device, each of the plurality of segments to the representations of clustered segments for each of the plurality of groups that correspond to the particular resection cut to which the segments correspond;

determining, by the implant matching computing device, matching groups that include a group for each resection cut based on the comparison; and selecting, by the implant matching computing device, an implant design based on the matching groups.

3. The method of claim 1 further comprising:

accessing, by the implant matching computing device, representations of clustered segments that include a representation of clustered segments for a single group defined for each of the resection cuts;

reassembling, by the implant matching computing device, the accessed representations into a two-dimensional outline representation of the portion of the bone;

generating, by the implant matching computing device, an implant design based on the reassembled two-dimensional outline representation of the portion of the bone; and storing, by the implant matching computing device, the implant design in association with data identifying the single group defined for each of the resection cuts.

4. The method of claim 1 further comprising:

comparing, by the implant matching computing device, one or more parameters of each of the plurality of segments to parameters that are associated with available implant designs and that correspond to the particular resection cut to which each of the plurality of segments corresponds;

determining, by the implant matching computing device, a match for an available implant design based on the comparison; and outputting, by the implant matching computing device, the available implant design based on the determination of the match for the available implant design.

5. The method of claim 1 further comprising:

generating, by the implant matching computing device, a custom implant based on one or more segments of the plurality of segments that correspond to the resection cuts used in fitting the implant on the portion of the bone.

6. The method of claim 1, wherein the portion of the bone comprises a distal end of a femur and the plurality of segments comprises:

a first segment that corresponds to a distal face of the distal end of the femur;

a second segment that corresponds to an anterior chamfer of the distal end of the femur;

a third segment that corresponds to a posterior chamfer of the distal end of the femur;

a fourth segment that corresponds to an anterior flange of the distal end of the femur; and a fifth segment that corresponds to posterior condyles of the distal end of the femur.

7. The method of claim 6 further comprising:

determining, by the implant matching computing device, a first match for the first segment to a representation of clustered segments for a distal face resection cut;

determining, by the implant matching computing device, a second match for the second segment to a representation of clustered segments for an anterior chamfer resection cut;

determining, by the implant matching computing device, a third match for the third segment to a representation of clustered segments for a posterior chamfer resection cut;

determining, by the implant matching computing device, a fourth match for the fourth segment to a representation of clustered segments for an anterior flange resection cut;

determining, by the implant matching computing device, a fifth match for the fifth segment to a representation of clustered segments for a posterior condyles resection cut; and selecting, by the implant matching computing device, an available implant design based on the first match for the first segment, the second match for the second segment, the third match for the third segment, the fourth match for the fourth segment, and the fifth match for the fifth segment.

8. A system for optimizing autonomous implant matching, the system comprising:

at least one processor; and at least one computer-readable medium coupled to the at least one processor having stored thereon instructions that, when executed by the at least one processor, causes the at least one processor to perform operations comprising:

segmenting two-dimensional outline representations of outer surfaces of peripheries of three-dimensional bone volumes generated from three-dimensional models of portions of bones and corresponding to resection cuts used in fitting an implant on the portions of the bones to generate a plurality of segments, the segmenting comprising:

identifying, by the implant matching computing device, edge locations of adjacent resection cuts on the two-dimensional outline representation; and separating, by the implant matching computing device, the two-dimensional outline at the identified edge locations into non-contiguous sections to form the segments;

storing the plurality of segments in a database, each of the plurality of segments corresponding to a particular resection cut and including data representing an outline of the bone at the particular resection cut;

analyzing characteristics of the plurality of segments stored in the database for each of the resection cuts;

clustering the plurality of segments stored in the database for each of the resection cuts into a plurality of groups, each group comprising segments of the plurality of segments having similar physical characteristics; and defining an average outline representation of the clustered segments for each of the plurality of groups.

9. The system of claim 8, wherein the at least one computer-readable medium has stored thereon at least one additional instruction that, when executed by the at least one processor, causes the at least one processor to perform operations comprising:

comparing each of the plurality of segments to the representations of clustered segments for each of the plurality of groups that correspond to the particular resection cut to which the segments correspond;

determining matching groups that include a group for each resection cut based on the comparison; and selecting an implant design based on the matching groups.

10. The system of claim 8, wherein the at least one computer-readable medium has stored thereon at least one additional instruction that, when executed by the at least one processor, causes the at least one processor to perform operations comprising:

accessing representations of clustered segments that include a representation of clustered segments for a single group defined for each of the resection cuts;

reassembling the accessed representations into a two-dimensional outline representation of the portion of the bone;

generating an implant design based on the reassembled two-dimensional outline representation of the portion of the bone; and storing the implant design in association with data identifying the single group defined for each of the resection cuts.

11. The system of claim 8, wherein the at least one computer-readable medium has stored thereon at least one additional instruction that, when executed by the at least one processor, causes the at least one processor to perform operations comprising:

comparing one or more parameters of each of the plurality of segments to parameters that are associated with available implant designs and that correspond to the particular resection cut to which each of the plurality of segments corresponds;

determining a match for an available implant design based on the comparison; and outputting the available implant design based on the determination of the match for the available implant design.

12. The system of claim 8, wherein the at least one computer-readable medium has stored thereon at least one additional instruction that, when executed by the at least one processor, causes the at least one processor to perform operations comprising:

generating a custom implant based on one or more segments of the plurality of segments that correspond to the resection cuts used in fitting the implant on the portion of the bone.

13. The system of claim 8, wherein the portion of the bone comprises a distal end of a femur and the plurality of segments comprises:

a first segment that corresponds to a distal face of the distal end of the femur;

a second segment that corresponds to an anterior chamfer of the distal end of the femur;

a third segment that corresponds to a posterior chamfer of the distal end of the femur;

a fourth segment that corresponds to an anterior flange of the distal end of the femur; and a fifth segment that corresponds to posterior condyles of the distal end of the femur.

14. The system of claim 13, wherein the at least one computer-readable medium has stored thereon at least one additional instruction that, when executed by the at least one processor, causes the at least one processor to perform operations comprising:

determining a first match for the first segment to a representation of clustered segments for a distal face resection cut;

determining a second match for the second segment to a representation of clustered segments for an anterior chamfer resection cut;

determining a third match for the third segment to a representation of clustered segments for a posterior chamfer resection cut;

determining a fourth match for the fourth segment to a representation of clustered segments for an anterior flange resection cut;

determining a fifth match for the fifth segment to a representation of clustered segments for a posterior condyles resection cut; and selecting an available implant design based on the first match for the first segment, the second match for the second segment, the third match for the third segment, the fourth match for the fourth segment, and the fifth match for the fifth segment.

15. A non-transitory computer-readable storage medium encoded with executable instructions that, when executed by at least one processor, cause the at least one processor to perform operations comprising:

segmenting two-dimensional outline representations of outer surfaces of peripheries of three-dimensional bone volumes generated from three-dimensional models of portions of bones and corresponding to resection cuts used in fitting an implant on the portions of the bones to generate a plurality of segments, the segmenting comprising:

identifying, by the implant matching computing device, edge locations of adjacent resection cuts on the two-dimensional outline representation; and separating, by the implant matching computing device, the two-dimensional outline at the identified edge locations into non-contiguous sections to form the segments;

storing the plurality of segments in a database, each of the plurality of segments corresponding to a particular resection cut and including data representing an outline of the bone at the particular resection cut;

analyzing characteristics of the plurality of segments stored in the database for each of the resection cuts;

clustering the plurality of segments stored in the database for each of the resection cuts into a plurality of groups, each group comprising segments of the plurality of segments having similar physical characteristics; and defining an average outline representation of the clustered segments for each of the plurality of groups.

16. The medium of claim 15 having stored thereon at least one additional instruction that, when executed by the at least one processor, causes the at least one processor to perform operations comprising:

comparing each of the plurality of segments to the representations of clustered segments for each of the plurality of groups that correspond to the particular resection cut to which the segments correspond;

determining matching groups that include a group for each resection cut based on the comparison; and selecting an implant design based on the matching groups.

17. The medium of claim 15 having stored thereon at least one additional instruction that, when executed by the at least one processor, causes the at least one processor to perform operations comprising:

accessing representations of clustered segments that include a representation of clustered segments for a single group defined for each of the resection cuts;

reassembling the accessed representations into a two-dimensional outline representation of the portion of the bone;

generating an implant design based on the reassembled two-dimensional outline representation of the portion of the bone; and storing the implant design in association with data identifying the single group defined for each of the resection cuts.

18. The medium of claim 15 having stored thereon at least one additional instruction that, when executed by the at least one processor, causes the at least one processor to perform operations comprising:
- comparing one or more parameters of each of the plurality of segments to parameters that are associated with available implant designs and that correspond to the particular resection cut to which each of the plurality of segments corresponds; and
- determining a match for an available implant design based on the comparison; and
- outputting the available implant design based on the determination of the match for the available implant design.

19. The medium of claim 15 having stored thereon at least one additional instruction that, when executed by the at least one processor, causes the at least one processor to perform operations comprising:
- generating a custom implant based on one or more segments of the plurality of segments that correspond to the resection cuts used in fitting the implant on the portion of the bone.

20. The medium of claim 15, wherein the portion of the bone comprises a distal end of a femur and the plurality of segments comprises:
- a first segment that corresponds to a distal face of the distal end of the femur;
- a second segment that corresponds to an anterior chamfer of the distal end of the femur;
- a third segment that corresponds to a posterior chamfer of the distal end of the femur;
- a fourth segment that corresponds to an anterior flange of the distal end of the femur; and
- a fifth segment that corresponds to posterior condyles of the distal end of the femur.

21. The medium of claim 20 having stored thereon at least one additional instruction that, when executed by the at least one processor, causes the at least one processor to perform operations comprising:
- determining a first match for the first segment to a representation of clustered segments for a distal face resection cut;
- determining a second match for the second segment to a representation of clustered segments for an anterior chamfer resection cut;
- determining a third match for the third segment to a representation of clustered segments for a posterior chamfer resection cut;
- determining a fourth match for the fourth segment to a representation of clustered segments for an anterior flange resection cut;
- determining a fifth match for the fifth segment to a representation of clustered segments for a posterior condyles resection cut; and
- selecting an available implant design based on the first match for the first segment, the second match for the second segment, the third match for the third segment, the fourth match for the fourth segment, and the fifth match for the fifth segment.

* * * * *